US009180151B2

(12) United States Patent
Kirn et al.

(10) Patent No.: US 9,180,151 B2
(45) Date of Patent: *Nov. 10, 2015

(54) ONCOLYTIC VACCINIA VIRUS COMBINATION CANCER THERAPY

(71) Applicant: SillaJen Biotherapeutics, Inc., San Francisco, CA (US)

(72) Inventors: David Kirn, Mill Valley, CA (US); Caroline Breitbach, San Francisco, CA (US)

(73) Assignee: SillaJen Biotherapeutics, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/273,476

(22) Filed: May 8, 2014

(65) Prior Publication Data

US 2014/0322173 A1 Oct. 30, 2014

Related U.S. Application Data

(63) Continuation of application No. 13/395,929, filed as application No. PCT/US2010/048829 on Sep. 14, 2010, now Pat. No. 8,747,837.

(60) Provisional application No. 61/244,250, filed on Sep. 21, 2009, provisional application No. 61/242,238, filed on Sep. 14, 2009.

(51) Int. Cl.
*A61K 35/76* (2015.01)
*A61K 31/44* (2006.01)
*A61K 35/768* (2015.01)
*A61K 31/4412* (2006.01)
*A61K 38/19* (2006.01)

(52) U.S. Cl.
CPC .............. *A61K 35/768* (2013.01); *A61K 31/44* (2013.01); *A61K 31/4412* (2013.01); *A61K 38/193* (2013.01); *C12N 2710/24132* (2013.01)

(58) Field of Classification Search
CPC ................... A61K 35/768; C12N 2710/24132
See application file for complete search history.

(56) References Cited

U.S. PATENT DOCUMENTS

| 4,554,101 | A | 11/1985 | Hopp |
|---|---|---|---|
| 4,683,195 | A | 7/1987 | Mullis et al. |
| 4,683,202 | A | 7/1987 | Mullis |
| 4,684,611 | A | 8/1987 | Schilperoort et al. |
| 4,800,159 | A | 1/1989 | Mullis et al. |
| 4,879,236 | A | 11/1989 | Smith et al. |
| 4,883,750 | A | 11/1989 | Whiteley et al. |
| 4,946,773 | A | 8/1990 | Maniatis et al. |
| 4,952,500 | A | 8/1990 | Finnerty et al. |
| 5,073,627 | A | 12/1991 | Curtis et al. |
| 5,151,509 | A | 9/1992 | Kotwal et al. |
| 5,220,007 | A | 6/1993 | Pederson et al. |
| 5,279,721 | A | 1/1994 | Schmid |
| 5,284,760 | A | 2/1994 | Feinstone et al. |
| 5,302,523 | A | 4/1994 | Coffee et al. |
| 5,322,783 | A | 6/1994 | Tomes et al. |
| 5,354,670 | A | 10/1994 | Nickoloff et al. |
| 5,366,878 | A | 11/1994 | Pederson et al. |
| 5,384,253 | A | 1/1995 | Krzyzek et al. |
| 5,389,514 | A | 2/1995 | Taylor |
| 5,399,363 | A | 3/1995 | Liversidge et al. |
| 5,464,765 | A | 11/1995 | Coffee et al. |
| 5,466,468 | A | 11/1995 | Schneider et al. |
| 5,538,877 | A | 7/1996 | Lundquist et al. |
| 5,538,880 | A | 7/1996 | Lundquist et al. |
| 5,543,158 | A | 8/1996 | Gref et al. |
| 5,550,318 | A | 8/1996 | Adams et al. |
| 5,563,055 | A | 10/1996 | Townsend et al. |
| 5,580,859 | A | 12/1996 | Felgner et al. |
| 5,589,466 | A | 12/1996 | Felgner et al. |
| 5,591,616 | A | 1/1997 | Hiei et al. |
| 5,610,042 | A | 3/1997 | Chang et al. |
| 5,633,016 | A | 5/1997 | Johnson |
| 5,635,377 | A | 6/1997 | Pederson et al. |
| 5,641,515 | A | 6/1997 | Ramtoola |
| 5,656,465 | A | 8/1997 | Panicali et al. |
| 5,656,610 | A | 8/1997 | Shuler et al. |
| 5,702,932 | A | 12/1997 | Hoy et al. |
| 5,719,054 | A | 2/1998 | Boursnell et al. |
| 5,736,524 | A | 4/1998 | Content et al. |
| 5,739,169 | A | 4/1998 | Ocain et al. |
| 5,762,938 | A | 6/1998 | Paoletti et al. |
| 5,780,448 | A | 7/1998 | Davis |
| 5,789,166 | A | 8/1998 | Bauer et al. |
| 5,789,215 | A | 8/1998 | Berns et al. |
| 5,798,208 | A | 8/1998 | Crea |
| 5,798,339 | A | 8/1998 | Brandes |
| 5,801,005 | A | 9/1998 | Cheever et al. |
| 5,824,311 | A | 10/1998 | Greene et al. |
| 5,824,348 | A | 10/1998 | Fujiu et al. |
| 5,830,650 | A | 11/1998 | Crea |

(Continued)

FOREIGN PATENT DOCUMENTS

| CA | 2105277 | 12/2006 |
|---|---|---|
| CA | 2375189 | 2/2010 |

(Continued)

OTHER PUBLICATIONS

Sandhu et al. (Expert Review of Gastroenterology & Hepatology, Feb. 2008, vol. 2, No. 1, pp. 81-92).*
Amato et al. (Drugs. 2006; 66(17): 2161-2171).*
Kirn et al (Nature Reviews Cancer. Jan. 2009; 9: 64-71).*
Abou-Alfa, G., et al., "Phase II Study of Sorafenib in Patients with Advanced Hepatocellular Carcinoma," J. Clin. Oncol., vol. 24, No. 26, pp. 4293-4300 (Sep. 10, 2006).
Adams, M., et al., "Clinical studies of human papilloma vaccines in pre-invasive and invasive cancer," Vaccine, vol. 19, Issues 17-19, pp. 2549-2556 (Mar. 2001).

(Continued)

Primary Examiner — Scott Long
(74) Attorney, Agent, or Firm — Morgan, Lewis & Bockius LLP

(57) ABSTRACT

Embodiments of the invention are directed methods that include a thymidine kinase deficient vaccinia virus. The methods include evaluating a tumor for reperfusion after treatment with vaccinia virus and administering an anti-angiogenic agent if reperfusion is detected.

22 Claims, 18 Drawing Sheets

(56) References Cited

U.S. PATENT DOCUMENTS

| | | | |
|---|---|---|---|
| 5,830,880 A | 11/1998 | Sedlacek et al. |
| 5,840,873 A | 11/1998 | Nelson et al. |
| 5,843,640 A | 12/1998 | Patterson et al. |
| 5,843,650 A | 12/1998 | Segev |
| 5,843,651 A | 12/1998 | Stimpson et al. |
| 5,843,663 A | 12/1998 | Stanley et al. |
| 5,846,225 A | 12/1998 | Rosengart et al. |
| 5,846,233 A | 12/1998 | Lilley et al. |
| 5,846,708 A | 12/1998 | Hollis et al. |
| 5,846,709 A | 12/1998 | Segev |
| 5,846,717 A | 12/1998 | Brow et al. |
| 5,846,726 A | 12/1998 | Nadeau et al. |
| 5,846,729 A | 12/1998 | Wu et al. |
| 5,846,783 A | 12/1998 | Wu et al. |
| 5,846,945 A | 12/1998 | McCormick |
| 5,849,481 A | 12/1998 | Urdea et al. |
| 5,849,483 A | 12/1998 | Shuber |
| 5,849,486 A | 12/1998 | Heller et al. |
| 5,849,487 A | 12/1998 | Hase et al. |
| 5,849,497 A | 12/1998 | Steinman |
| 5,849,546 A | 12/1998 | Sousa et al. |
| 5,849,547 A | 12/1998 | Cleuziat et al. |
| 5,851,770 A | 12/1998 | Babon et al. |
| 5,851,772 A | 12/1998 | Mirzabekov et al. |
| 5,853,990 A | 12/1998 | Winger et al. |
| 5,853,992 A | 12/1998 | Glazer et al. |
| 5,853,993 A | 12/1998 | Dellinger et al. |
| 5,856,092 A | 1/1999 | Dale et al. |
| 5,858,652 A | 1/1999 | Laffler et al. |
| 5,861,244 A | 1/1999 | Wang et al. |
| 5,863,732 A | 1/1999 | Richards |
| 5,863,753 A | 1/1999 | Haugland et al. |
| 5,866,331 A | 2/1999 | Singer et al. |
| 5,866,337 A | 2/1999 | Schon |
| 5,866,366 A | 2/1999 | Kallender |
| 5,871,740 A | 2/1999 | Smith |
| 5,871,986 A | 2/1999 | Boyce |
| 5,882,864 A | 3/1999 | An et al. |
| 5,900,481 A | 5/1999 | Lough et al. |
| 5,905,024 A | 5/1999 | Mirzabekov et al. |
| 5,910,407 A | 6/1999 | Vogelstein et al. |
| 5,912,124 A | 6/1999 | Kumar |
| 5,912,145 A | 6/1999 | Stanley |
| 5,912,148 A | 6/1999 | Eggerding |
| 5,916,776 A | 6/1999 | Kumar |
| 5,916,779 A | 6/1999 | Pearson et al. |
| 5,919,626 A | 7/1999 | Shi et al. |
| 5,919,630 A | 7/1999 | Nadeau et al. |
| 5,922,574 A | 7/1999 | Minter |
| 5,925,517 A | 7/1999 | Tyagi et al. |
| 5,925,525 A | 7/1999 | Fodor et al. |
| 5,925,565 A | 7/1999 | Berlioz et al. |
| 5,928,862 A | 7/1999 | Morrison |
| 5,928,869 A | 7/1999 | Nadeau et al. |
| 5,928,870 A | 7/1999 | Lapidus et al. |
| 5,928,905 A | 7/1999 | Stemmer et al. |
| 5,928,906 A | 7/1999 | Koster et al. |
| 5,929,227 A | 7/1999 | Glazer et al. |
| 5,932,413 A | 8/1999 | Celebuski |
| 5,932,451 A | 8/1999 | Wang et al. |
| 5,935,791 A | 8/1999 | Nadeau et al. |
| 5,935,819 A | 8/1999 | Eichner et al. |
| 5,935,825 A | 8/1999 | Nishimura et al. |
| 5,939,291 A | 8/1999 | Loewy et al. |
| 5,942,391 A | 8/1999 | Zhang et al. |
| 5,945,100 A | 8/1999 | Fick |
| 5,969,094 A | 10/1999 | Compans et al. |
| 5,981,274 A | 11/1999 | Tyrrell et al. |
| 5,994,624 A | 11/1999 | Trolinder et al. |
| 6,093,700 A | 7/2000 | Mastrangelo et al. |
| 6,177,076 B1 | 1/2001 | Lattime et al. |
| 6,265,189 B1 | 7/2001 | Paoletti et al. |
| 6,355,252 B1 | 3/2002 | Smith et al. |
| 6,475,999 B1 | 11/2002 | Mastrangelo et al. |
| 6,521,449 B1 | 2/2003 | Polack et al. |
| 7,208,313 B2 | 4/2007 | McCart et al. |
| 7,326,529 B2 | 2/2008 | Ali et al. |
| 7,588,767 B2 | 9/2009 | Szalay et al. |
| 7,588,771 B2 | 9/2009 | Szalay et al. |
| 8,105,578 B2 | 1/2012 | Roberts et al. |
| 8,747,837 B2 * | 6/2014 | Kirn et al. ............... 424/93.6 |
| 2002/0086022 A1 | 7/2002 | Davis |
| 2002/0146702 A1 | 10/2002 | Vielkind |
| 2003/0025141 A1 | 2/2003 | Grimm |
| 2003/0086906 A1 | 5/2003 | Mastrangelo et al. |
| 2003/0206886 A1 | 11/2003 | Lattime et al. |
| 2004/0091995 A1 | 5/2004 | Schlom et al. |
| 2005/0031617 A1 | 2/2005 | Ma et al. |
| 2005/0031643 A1 | 2/2005 | Szalay et al. |
| 2005/0207974 A1 | 9/2005 | Deng et al. |
| 2006/0051370 A1 | 3/2006 | Szalay et al. |
| 2007/0025981 A1 | 2/2007 | Szalay et al. |
| 2007/0065411 A1 | 3/2007 | Kirn |
| 2008/0286237 A1 | 11/2008 | Kirn |
| 2009/0004723 A1 | 1/2009 | Kirn et al. |
| 2009/0047307 A1 | 2/2009 | Harrop et al. |
| 2009/0053244 A1 | 2/2009 | Chen et al. |
| 2010/0303714 A1 | 12/2010 | Kirn |

FOREIGN PATENT DOCUMENTS

| | | | |
|---|---|---|---|
| CA | 2370187 | | 8/2011 |
| CA | 2305269 | | 7/2012 |
| CA | 2388807 | | 8/2013 |
| DE | WO2008/043576 | * | 4/2008 ............ A61K 35/76 |
| EP | 0329822 | | 8/1989 |
| EP | 0320308 | | 11/1993 |
| GB | 2202328 | | 9/1988 |
| WO | WO 87/06270 | | 10/1987 |
| WO | WO 88/10315 | | 12/1988 |
| WO | WO 89/06700 | | 7/1989 |
| WO | WO 89/09284 | | 10/1989 |
| WO | WO 94/09699 | | 5/1994 |
| WO | WO 95/06128 | | 3/1995 |
| WO | WO 99/29343 | | 6/1999 |
| WO | WO 00/62735 | | 10/2000 |
| WO | WO 00/73479 | | 12/2000 |
| WO | WO 2004/014314 | | 2/2004 |
| WO | WO 2008/043576 | | 4/2008 |
| WO | WO 2008/047242 | | 4/2008 |
| WO | WO 2008/113078 | | 9/2008 |

OTHER PUBLICATIONS

Aigner, F., et al., "Anal HPV infections," Wiener Klinosche Woechenschrift, vol. 120, Issues 19-20, pp. 631-641 (Oct. 2008) (Abstract).

Alcami, A., et al., "A soluble Receptor for Interleukin-1beta encoded by Vaccinia Virus: A Novel Mechanism of Virus Modulation of the Host Response to Infection," Cell, vol. 71, No. 1, pp. 153-167 (Oct. 2, 1992).

Alcami, A., et al., "The vaccinia virus soluble interferon-gamma receptor is a homodimer," J Gen Virol., vol. 83, Pt. 3. pp. 545-549 (Mar. 2002).

Alcami, A., et al., "Poxviruses: Capturing Cytokines and Chemokines," Sem Virol, vol. 8, No. 5, pp. 419-427 (Apr. 1998).

Alcami, A., et al., "The vaccinia virus soluble alpha/beta interferon (IFN) receptor binds to the cell surface and protects cells from the antiviral effect of IFN," J Virology, vol. 74, No. 23, pp. 11230-11239 (Dec. 2000).

Alcami, A., et al., "Vaccinia virus strains Lister, USSR and Evans express soluble and cell-surface tumour necrosis factor receptors," J Gen Virol, vol. 80, Pt 4, pp. 949-959 (Apr. 1999).

Alimonti, J., et al., "TAP expression provides a general method for improving the recognition of malignant cells in vivo," Nature Biotech, vol. 18, No. 5, pp. 515-520 (May 2000).

Almendro, N., et al., "Cloning of the Human Platelet Endothelial Cell Adhesion Molecule-1 Promoter and Its Tissue-Specific Expression," Immunol., vol. 157, No. 12, pp. 5411-5421 (Dec. 15, 1996).

Amato, R., et al., "Vaccination of Prostate Cancer Patients With Modified Vaccinia Ankara Delivering the Tumor Antigen 5T4 (TroVax): A Phase 2 Trial," Journal Immunother., vol. 31, No. 6, pp. 577-585 (Jul.-Aug. 2008).

(56) References Cited

OTHER PUBLICATIONS

Amato, R., et al., "Targeted Anti-Cancer Therapies for Renal Cancer," Drugs, vol. 66, No. 17, pp. 2161-2171 (Dec. 2006).
Ananvoranich, S., et al., "Duplication of a Region in the Multiple Cloning Site of a Plasmid Vector to Enhance Cloning-Mediated Addition of Restriction Sites to a DNA Fragment," Biotechniques, vol. 23, No. 5, pp. 814-816 (Nov. 1997).
Andoh, A., et al., "Sodium butyrate enhances complement-mediated cell injury via down-regulation of decay-accelerating factor expression in colonic cancer cells," Cancer Immunol Immunother, vol. 50, No. 12, pp. 663-672 (Feb. 2002).
Angel, P., et al., "Phorbol Ester-Inducible Genes Contain a Common Cis Element Recognized by a TPA-Modulated Trans-Acting Factor," Cell, vol. 49, pp. 729-739 (Jun. 19, 1987).
Angel, P., et al., "12-O-tetradecanoyl-phorbol-13-acetate Induction of the Human Collagenase Gene is Mediated by an Inducible Enhancer Element Located in the 5'-flanking Region," Mol. Cell. Biol., vol. 7, pp. 2256-2266 (Jun. 1987).
Arakawa, S., et al., "Clinical trial of attenuated vaccinia virus AS strain in the treatment of advanced adenocarcinoma," J Cancer Res Clin Oncol, vol. 113, pp. 95-98 (Feb. 1987).
Arap, W., et al., "Replacement of the p16/CDKN2 Gene Suppresses Human Glioma Cell Growth," Cancer Res., vol. 55, No. 6, pp. 1351-1354 (Mar. 15, 1995).
Arness, M., et al., "Myopericarditis Following Smallpox Vaccination," Am. J. Epidemiol., vol. 160, pp. 642-651 (Apr. 2004).
Atchinson, M., et al., "The Role of the k Enhancer and Its Binding Factor Nf-KB in the Developmental Regulation of K Gene Transcription," Cell, vol. 48, pp. 121-128 (Jan. 16, 1987).
Atchinson, P., "Tandem Kappa Immunoglobulin Promoters are Equally Active in the Presence of the Kappa Enhancer: Implications for Models of Enhancer Function," Cell, vol. 46, pp. 253-262 (Jul. 18, 1986).
Austin-Ward, E., et al., "Gene therapy and its applications," Rev Med Chil, vol. 126, No. 7, pp. 838-845 (Jul. 1998).
Bajorin, D., et al., "Comparison of Criteria for Assigning Germ Cell Tumor Patients to 'Good Risk' and 'Poor Risk' Studies," J. Clin. Oncol., vol. 6, No. 5, pp. 786-792 (May 1988).
Bakhshi, A., et al., "Cloning the Chromosomal Breakpoint of t(14;18) Human Lymphomas: Clustering around Jh on Chromosome 14 and near a Transcriptional Unit on 18," Cell, vol. 41, No. 3, pp. 899-906 (Jul. 1985).
Banerji, J., et al., "Expression of a β-Globin Gene is Enhanced by Remote SV40 DNA Sequences," Cell, vol. 27, pp. 299-308 (Dec. 1981).
Banerji, J., et al., "A Lymphocyte-Specific Cellular Enhancer is Located Downstream of the Joining Region in Immunoglobulin Heavy Chain Genes," Cell, vol. 33, No. 3, pp. 729-740 (Jul. 1983).
Baranyi, L., et al., "Membrane-Bound Complement Regulatory Activity is Decreased on Vaccinia Virus-Infected Cells," Clin Exp Immunol., vol. 98, No. 1, pp. 134-139 (Jun. 1994).
Bartlett, N., et al., "The vaccinia virus N1L protein is an intracellular homodimer that promotes virulence," J. Gen. Virol., vol. 83, pp. 1965-1976 (Aug. 2002).
Bell, J., et al., "Getting Oncolytic Virus Therapies Off the Ground," Cancer Cell, vol. 4, No. 1, pp. 7-11 (Jul. 2003).
Bellus, D., "How do Specialty Polymers Modify the Chemical and Pharmaceutical Industries," Macromol. Sci. Pure Appl. Chem., vol. A31, No. 1, pp. 1355-1376 (Oct. 1994).
Berkhout, B., et al., "Tat trans-activates the human immunodeficiency virus through a nascent RNA target," Cell, vol. 59, pp. 273-282 (Oct. 20, 1989).
Berwin, B., et al., "Virally induced lytic cell death elicits the release of immunogenic GRP94/gp96," J Biol Chem, vol. 276, No. 24, pp. 21083-21088 (Mar. 28, 2001).
Bischoff, J., et al., "An Adenovirus Mutant that Replicates Selectively in p53-deficient Human Tumor Cells," Science, vol. 274, pp. 373-376 (Oct. 18, 1996).

Blanar, M., et al., "A gamma-interferon-induced factor that binds the interferon response sequence of the MHC class I gene, H-2Kb," Embo J., vol. 8, pp. 1139-1144 (Apr. 1989).
Blanchard, T., et al., "Modified vaccinia virus Ankara undergoes limited replication in human cell and lacks several immunomodulatory proteins: implications for use as a human vaccine," J Gen Virol., vol. 79, Pt 5, pp. 1159-1167 (May 1998).
Blanchard, T., et al., "Vaccinia virus strain modified virus ankara: characterization of cytokine receptor profile, virological features, and use as an immunological reagent," Conf Adv AIDS Vaccine Dev, 108 (Poster 3): May 4-7, 1997 (Abstract).
Blasco, R., et al., "Role of cell-associated enveloped vaccinia virus in cell-to-cell spread," J Virology, vol. 66, No. 7, pp. 4170-4179 (Jul. 1992).
Blasco, R., et al., "Dissociation of progeny vaccinia virus from the cell membrane is regulated by a viral envelope glycoprotein: effect of a point mutation in the lectin homology domain of the A34R gene," J Virology, vol. 67, No. 6, pp. 3319-3325 (Jun. 1993).
Bodine, D., et al., "An enhancer element lies 3' to the human A gamma globin gene.," Embo J., vol. 6, pp. 2997-3004 (Oct. 1987).
Boshart, M., et al., "A very strong enhancer is located upstream of an immediate early gene of human cytomegalovirus," Cell, vol. 41, pp. 521-530 (Jun. 1985).
Bosze, Z., et al., "A transcriptional enhancer with specificity for erythroid cells is located in the long terminal repeat of the Friend murine leukemia virus," Embo J., vol. 5, No. 7, pp. 1615-1623 (Jul. 1986).
Bowie, A., et al., "A46R and A52R from vaccinia virus are antagonist of host IL-1 and toll-like receptor signaling," Proc Natl Acad Sci USA, vol. 97, No. 18, pp. 10162-10167, (Aug. 2000).
Boyd, J., et al., "Adenovirus E1B 19 kDa and Bcl-2 proteins interact with a common set of cellular proteins," Cell, vol. 79, Issue 2, pp. 341-351 (Oct. 1994).
Braddock, M., et al., "HIV-1 TAT 'activates' presynthesized RNA in the nucleus," Cell. vol. 58, p. 269-279 (Jul. 28, 1989).
Braisted, A., et al., "Minimizing a binding domain from protein A," Proc. Natl. Acad. Sci. USA, vol. 93, No. 12, pp. 5688-5692 (Jun. 1996).
Bretibach, C. J., et al., "Intravenous Delivery of a Multi-Mechanistic Cancer-Targeted Oncolytic Poxvirus in Humans," vol. 477, pp. 99-102 (Sep. 2011).
Bretibach, C. J., et al., "Targeted Inflammation During Oncolytic Virus Therapy Severely Compromises Tumor Blood Flow," Mol. Ther., vol. 15, No. 9, pp. 1686-1693 (Jun. 19, 2007).
Brizel, D., Radiotherapy and concurrent chemotherapy for the treatment of locally advanced head and neck squamous cell carcinoma: Semin. Radiat. Oncol., vol. 8, No. 4, pp. 237-246 (Oct. 1998).
Broyles, S., et al., "Antiviral activity of distamycin A against vaccinia virus is the result of inhibition of postreplicative mRNA synthesis," J. Virol., vol. 78, No. 4, pp. 2137-2141 (Feb. 2004).
Bukowski, R., et al., "Signal transduction abnormalities in T lymphocytes from patients with advanced renal carcinoma: clinical relevance and effects of cytokine therapy," Clin Cancer Res, vol. 4, No. 10, pp. 2337-2347 (Oct. 1998).
Bulla, G., et al., "The hepatitis B virus enhancer modulates transcription of the hepatitis B virus surface antigen gene from an internal location" Journal of Virol., vol. 62, No. 4, pp. 1437-1441 (Apr. 1988).
Buller, R., et al., "Poxvirus Pathogenesis," Microbiol Rev, vol. 55, No. 1, pp. 80-122 (Mar. 1991).
Burke, F., "Cytokines (IFNs, TNF-alpha, IL-2 and IL-12) and animal models of cancer," Cytokines Cell Mol Ther, vol. 5, No. 1, pp. 51-61 (Mar. 1999).
Burton, D., et al., "Human Antibodies from Combinatorial Libraries," Advances in Immunology, vol. 57, pp. 191-280 (Nov. 1994).
Caldas, C., et al., "Detection of K-ras Mutations in the Stool of Patients with Pancreatic Adenocarcinoma and Pancreatic Ductal Hyperplasia," Cancer Research, vol. 54, pp. 3568-3573 (Jul. 1, 1994).
Caldas, C., et al., "Frequent somatic mutations and homozygous deletions of the p16 (MTS1) gene in pancreatic adenocarcinoma," Nat. Genet., vol. 8, No. 1, pp. 27-32 (Sep. 1994).

(56) References Cited

OTHER PUBLICATIONS

Campbell, B., et al., "Functional Analysis of the Individual Enhancer Core Sequences of Polyomavirus: Cell-Specific Uncoupling of DNA Replication from Transcription," Mol. Cell Biol., vol. 8, pp. 1993-2004 (May 1988).
Camper, S., et al., "Postnatal repression of the alpha-fetoprotein gene is enhancer independent," Genes Dev., vol. 3, pp. 537-546 (Feb. 15, 1989).
Campo, M., et al., "Transcriptional control signals in the genome of bovine papillomavirus type 1," Nature, vol. 303, pp. 77-80 (May 5-11, 1983).
Cantrell, M., et al., "Cloning, sequence, and expression of a human granulocyte/macrophage colony-stimulating factor," Proc. Natl Acad. Sci. USA, vol. 82, pp. 6250-6254 (Sep. 1, 1985).
Caragine, T., et al., "A tumor-expressed inhibitor of the early but not late complement lytic pathway enhances tumor growth in a rat model of human breast cancer," Cancer Res, vol. 62, No. 4, pp. 1110-1115 (Feb. 15, 2002).
Carbonelli, D., et al., "A plasmid vector for isolation of strong promoters in Escherichia coli," Fems Microbiol. Lett, vol. 177, No. 1, pp. 75-82 (Jun. 7, 1999).
Cebon, J., et al., "The dissociation of GM-CSF efficacy from toxicity according to route of administration: a pharmacodynamic study," Br. J. Haematol., vol. 80, No. 2, pp. 144-150 (Feb. 1992).
Celander, D., et al., "Glucocorticoid regulation of murine leukemia virus transcription elements is specified by determinants within the viral enhancer region," Virology, vol. 61, pp. 269-275 (Feb. 1987).
Celander, D., et al., "Regulatory elements within the murine leukemia virus enhancer regions mediate glucocorticoid responsivene," Virology, vol. 62, pp. 1314-1322 (Apr. 1988).
Chandler, V., et al., "DNA sequences bound specifically by glucocorticoid receptor in vitro render a heterologous promoter hormone responsive in vivo," Cell., vol. 33, pp. 489-499 (Jun. 1983).
Chandler, S., et al., "RNA splicing specificity determined by the coordinated action of RNA recognition motifs in SR proteins," Proc. Natl. Acad. Sci. USA, vol. 94, No. 8, pp. 3596-3601 (Apr. 1997).
Chang, S., et al., "Glucose-regulated protein (GRP94 and GRP78) genes share common regulatory domains and are coordinately regulated by common trans-acting factors," vol. Cell. Biol., vol. 9, No. 5, pp. 2153-2162 (May 1989).
Chatterjee, V., et al., "Negative regulation of the thyroid-stimulating hormone a gene by thyroid hormone: Receptor interaction adjacent to the TATA box," Proc. Natl. Acad. Sci. USA, vol. 86, pp. 9114-9118 (Dec. 1989).
Chen, C., et al., "High-efficiency transformation of mammalian cells by plasmid DNA," Mol. Cell. Biol., vol. No. 7, No. 8, pp. 2745-2752 (Aug. 1987).
Chen, B., et al., "Low-dose vaccinia virus-mediated cytokine gene therapy of glioma," J Immunother, vol. 24, pp. 46-57 (Jan./Feb. 2001).
Cheng, A. L., Efficacy and Safety of Sorafenib in Patients in the Asia-Pacific Region with Advanced Hepatocellular Carcinoma: A Phase III Randomised, Double-Blind, Placebo-Controlled Trial., vol. 10, No. 1, pp. 25-34 (Jan. 2009).
Cheng, J., et al., "p16 Alterations and Deletion Mapping of 9p21-p22 in Malignant Mesothelioma." Cancer Res., vol. 54, No. 21, pp. 5547-5551 (Nov. 1, 1994).
Choi, K., et al., "An altered pattern of cross-resistance in multidrug-resistant human cells results from spontaneous mutations in the mdr1 (P-glycoprotein) gene," Cell, vol. 53, pp. 519-529 (May 1988).
Choi, H., et al., "Correlation of Computed Tomography and Positron Emission Tomography in Patients With Metastatic Gastrointestinal Stromal Tumor Treated at a Single Institution With Imatinib Mesylate: Proposal of New Computed Tomography Response Criteria," J. Clin. Oncol., vol. 25, No. 13, pp. 1753-1759 (May 1, 2007).
Choi, H., et al., "CT Evaluation of the Response of Gastrointestinal Stromal Tumors after Imatinib Mesylate Treatment: A Quantitative Analysis Correlated with FDG PET Findings," American Journal of Roentgenology, vol. 183, No. 6, pp. 1619-1628 (Dec. 2004).
Christodoulides, M., et al., "Immunization with recombinant class 1 outer-membrane protein from Neisseria meningitidis: influence of liposomes and adjuvants on antibody avidity, recognition of native protein and the induction of a bactericidal immune response against meningococci," Microbiology, vol. 144, Pt 11, pp. 3027-3037 (Nov. 1998).
Cleary, M., et al., "Detection of a second t(14;18) breakpoint cluster region in human follicular lymphomas," J. Exp. Med., vol. 164, No. 1, pp. 315-320 (Jul. 1986).
Cleary, M., et al., "Nucleotide sequence of a t(14;18) chromosomal breakpoint in follicular lymphoma and demonstration of a breakpoint-cluster region near a transcriptionally active locus on chromosome 18," Proc. Natl. Acad. Sci. USA, vol. 21, pp. 7435-7443 (Nov. 1985).
Cocea, L, "Duplication of a Region in the Multiple Cloning Site of a Plasmid Vector to Enhance Cloning-Mediated Addition of Restriction Sites to a DNA Fragment," Biotechniques, vol. 23, No. 5, pp. 814-816 (Nov. 1997).
Coffey, M., et al., "Reovirus Therapy of Tumors With Activated Ras Pathway," Science, vol. 282, pp. 1332-1334 (Nov. 13, 1998).
Cohen, J., et al., "A Repetitive Sequence Element 3' of the Human c-Ha-ras1 Gene Has Enhancer Activity," J Cell Physiol. Supplement, vol. 133, Issue S5, pp. 75-81 (Dec. 1987).
Coiffier, B., et al., "Safety and Efficacy of Ofatumumab, a Fully Human Monoclonal Anti-CD20 Antibody, in Patients With Relapsed or Refractory B-cell Chronic Lymphocytic Leukemia: A Phase 1-2 Study," Blood, vol. 111, No. 3, pp. 1094-1100, (Feb. 2008).
Colamonici, O., et al., "Vaccinia virus B18R gene encodes a type I interferon-binding protein that blocks interferon alpha transmembrane signaling," J Biol Chem, vol. 270, pp. 15974-15978 (Jul. 7, 1995).
Cooley, L., et al., "Insertional Mutagenesis of the Drosophila Genome with Single P Elements," Science, vol. 239, No. 4844, pp. 1121-1128 (Mar. 4, 1988).
Costa, R., et al., "The Cell-Specific Enhancer of the Mouse Transthyretin (Prealbumin) Gene Binds a Common Factor at One Site and a Liver-Specific Factor(s) at Two Other Sites, " Mol. Cell. Biol., vol. 8, pp. 81 (Jan. 1988).
Cripe, T., et al., "Transcriptional regulation of the human papillomavirus-16 E6-E7 promoter by a keratinocyte-dependent enhancer, and by viral E2 trans-activator and repressor gene products: implications for cervical carcinogenesis," Embo J. vol. 6, pp. 3745-3753 (Dec. 1987).
Culotta, V., et al., "Fine mapping of a mouse metallothionein gene metal response element," Mol. Cell Biol., vol. 9, pp. 1376-1380 (Mar. 1989).
Culver, K., et al., "In vivo gene transfer with retroviral vector-producer cells for treatment of experimental brain tumors," Science, vol. 156, No. 5603, pp. 1550-1552 (Jun. 12, 1992).
Cunningham, B., et al., "High-resolution epitope mapping of hGH-receptor interactions by alanine-scanning mutagenesis," Science, vol. 244, No. 4908, pp. 1081-1085 (Jun. 2, 1989).
Cunnion, K., "Tumor necrosis factor receptors encoded by poxviruses," Mol Genet Metab, vol. 67, No. 4, pp. 278-282 (Aug. 1999).
Curran, W., "Radiation-Induced Toxicities: The Role of Radioprotectants," Seminars Radiat. Oncol., vol. 8, Supp. 4, pp. 2-4 (Oct. 1998).
Dandolo, L., et al., "Regulation of Polyoma Virus Transcription in Murine Embryonal Carcinoma Cells," J. Virology, vol. 47, pp. 55-64 (Jul. 1983).
Davidson, J., et al., "Intralesional cytokine therapy in cancer: a pilot study of GM-CSF infusion in mesothelioma," J Immunother, vol. 21, No. 5, pp. 389-398 (Sep. 1998).
Dechant, M., et al., "Complement-Dependent Tumor Cell Lysis Triggered by Combinations of Epidermal Growth Factor Receptor Antibodies," Cancer Res., vol. 68, No. 13, pp. 4998-5003 (Jul. 1, 2008).
Demetri, G., et al., "Efficacy and Safety of Sunitinib in Patients with Advanced Gastrointestinal Stromal Tumour After Failure of Imatinib: A Randomised Controlled Trial," The Lancet, vol. 368, pp. 1329-1338 (Oct. 14, 2006).

(56) References Cited

OTHER PUBLICATIONS

Deschamps, J., et al., "Identification of a transcriptional enhancer element upstream from the proto-oncogene fos," Science, vol. 230, pp. 1174-1177 (Dec. 6, 1985).
DeVilliers, J., et al., "Polyoma virus DNA replication requires an enhancer," Nature, vol. 312, No. 5991, pp. 242-246 (Nov. 1984).
Di Gaetano, N., et al., "Complement Activation Determines the Therapeutic Activity of Rituximab In Vivo," J Immunol., vol. 171, No. 3, pp. 1581-1587 (Aug. 1, 2003).
Dillman, R., "Perceptions of Herceptin®: A Monoclonal Antibody for the Treatment of Breast Cancer," Biother. Radiopharm., vol. 14, No. 1, pp. 5-10 (Jan. 29, 2009).
Dobbelstein, M., et al., "Protection against apoptosis by the vaccinia virus SPI-2 (B13R) gene product," J Virology, vol. 70, pp. 6479-6485 (Sep. 1996).
Doehn, C., et al., "Technology evaluation: TG-1031, Transgene SA," Curr Opin Mol Ther, vol. 2, No. 1, pp. 106-111, (Feb. 2000).
Dranoff, G., et al., "Vaccination with irradiated tumor cells engineered to secrete murine granulocyte-macrophage colony-stimulating factor stimulates potent, specific, and long-lasting anti-tumor immunity," Proc. Natl. Acad. Sci. USA, vol. 90, No. 8, pp. 3539-3543 (Apr. 15, 1993).
Durrant, L., et al., "Immunization against tumor cell surface complement-regulatory proteins," Curr Opin Investig Drugs, vol. 2, No. 7, pp. 959-966 (Jul. 2001).
Edbrooke, M., et al., "Identification of cis-Acting Sequences Responsible for Phorbol Ester Induction of Human Serum Amyloid A Gene Expression via a Nuclear Factor KB-Like Transcription Factor," Mol. Cell Biol., vol. 9, pp. 1908 (May 1989).
Edlund, T., et al., "Cell-specific expression of the rat insulin gene: evidence for role of two distinct 5' flanking elements," Science, vol. 230, pp. 912-916 (Nov. 22, 1985).
Eliopoulos, A., et al., "The control of apoptosis and drug resistance in ovarian cancer: influence of p53 and Bcl-2," Oncogene, vol. 11, No. 7. pp. 1217-1228 (Oct. 5, 1995).
El-Kareh, A., "Theoretical models for drug delivery to solid tumors," Crit. Rev. Biomed. Eng., vol. 25, No. 6, pp. 503-571 (Feb. 1997).
Erlandsson, R., "Molecular Genetics of Renal Cell Carcinoma," Cancer Genet. Cytogenet., vol. 104, No. 1, pp. 1-18 (Jul. 1998).
Escudier, B., et al., "Sorafenib in Advanced Clear-Cell Renal-Cell Carcinoma," N. Engl. J. Med., vol. 356, No. 2, pp. 125-134 (Jan. 11, 2007).
Extended European Search Report issued in European Application No. 08167984.7, dated Mar. 6, 2009.
Extended European Search Report issued in European Patent Application No. 10181820.1, dated Dec. 7, 2010.
Extended European Search Report issued in European Patent Application No. 10181845.8, dated Dec. 3, 2010.
Extended European Search Report issued in European Patent Application No. 10816293.4 dated Mar. 4, 2014.
Fechheimer, M., et al., "Transfection of mammalian cells with plasmid DNA by scrape loading and sonication loading," Proc. Natl. Acad. Sci. USA, vol. 84, pp. 8463-8467 (Dec. 1987).
Feng, C., et al., "Induction of CD8+ T-lymphocyte responses to a secreted antigen of Mycobacterium tuberculosis by an attenuated vaccinia virus," Immunol Cell Biol., vol. 79, pp. 569-575 (Dec. 2001).
Feng, S., et al., "HIV-1 tat trans-activation requires the loop sequence within tar," Nature, vol. 334, pp. 165-167 (Jul. 14, 1988).
Ferguson, M., et al., "Systemic Delivery of Oncolytic Viruses: Hopes and Hurdles," Advances in Virology, vol. 2012, pp. 1-14 (Oct. 18, 2011).
Firak, T., et al., "Minimal Transcriptional Enhancer of Simian Virus 40 is a 74-Base-Pair Sequence That Has Interacting Domains," Mol. Cell. Biol., vol. 6, pp. 3667-3676 (Nov. 1986).
Foecking, M., et al., "Powerful and Versatile Enhancer-Promoter Unit for Mammalian Expression Vectors," Gene, vol. 45, No. 1, pp. 101-105 (Jun. 5, 1986).

Force, T., et al., "Cardiotoxicity of the new cancer therapeutics—mechanisms of, and approaches to, the problem," Drug Discovery Today, vol. 13, No. 17/18, pp. 778-784 (Sep. 2008).
Fraley, T., et al., "Entrapment of a bacterial plasmid in phospholipid vesicles: potential for gene transfer," Proc. Natl. Acad. Sci. USA, vol. 76, pp. 3348-3352 (Jul. 1979).
Frohman, M., "Chapter 4—Race: Rapid Amplification of cDNA Ends," PCR Protocols: A Guide to Methods and Applications, Academic Press, San Diego, pp. 28-38 and 228-236 (1990).
Fujita, T., et al., "Interferon-p Gene Regulation: Tandemly Repeated Sequences of a Synthetic 6 by Oligomer Function as a Virus-Inducible Enhancer," Cell, vol. 49, pp. 357-367 (May 8, 1987).
Gardner, J., et al., "Vaccinia virus semaphorin A39R is a 50-55 kDa secreted glycoprotein that affects the outcome of infection in a murine intradermal model," J Gen Virol., vol. 82, Pt 9, pp. 2083-2093 (Sep. 2001).
GenBank Accession No. AF216779.
GenBank Accession No. AF346406.
GenBank Accession No. AF349002.
GenBank Accession No. AF349003.
GenBank Accession No. AF349004.
GenBank Accession No. AF349005.
GenBank Accession No. AF349006.
GenBank Accession No. AF349007.
GenBank Accession No. AF349008.
GenBank Accession No. AF349009.
GenBank Accession No. AF349010.
GenBank Accession No. AF349011.
GenBank Accession No. AF349012.
GenBank Accession No. AF349013.
GenBank Accession No. AF349014.
GenBank Accession No. AF349015.
GenBank Accession No. AF349016.
GenBank Accession No. AJ269556.
GenBank Accession No. AJ309297.
GenBank Accession No. AJ312293.
GenBank Accession No. AJ314914.
GenBank Accession No. AJ314915.
GenBank Accession No. AJ314916.
GenBank Accession No. NC_001559.
Gertig, D., et al., "Genes and environment in the etiology of colorectal cancer," Semin. Cancer Biol., vol. 8, No. 4, pp. 285-298 (Aug. 1998).
Gilles, S., et al., "A tissue-specific transcription enhancer element is located in the major intron of a rearranged immunoglobulin heavy chain gene," Cell, vol. 33, pp. 717-728 (Jul. 1983).
Gloss, B., et al., "The upstream regulatory region of the human papilloma virus-16 contains an E2 protein-independent enhancer which is specific for cervical carcinoma cells and regulated by glucocorticoid hormones," Embo. J., vol. 6, pp. 3735-3743 (Dec. 1, 1987).
Gnant, M., et al., "Systemic administration of a recombinant vaccinia virus expressing the cytosine deaminase gene and subsequent treatment with 5- fluorocytosine leads to tumor-specific gene expression and prolongation of survival in mice," Cancer Res, vol. 59, No. 14, pp. 3396-3403 (Jul. 15, 1999).
Gnant, M., et al., "Regional Versus Systemic Delivery of Recombinant Vaccinia Virus as Suicide Gene Therapy for Murine Liver Metastases," Ann Surg., vol. 230, No. 3, pp. 352-360 (Sep. 1999).
Gnant, M., et al., "Tumor-Specific Gene Delivery Using Recombinant Vaccinia Virus in a Rabbit Model of Liver Metastases," J. Ntl. Cancer Inst., vol. 91, No. 20, pp. 1744-1750 (Oct. 20, 1999).
Godbout, R., et al., "Fine-Structure Mapping of the Three Mouse ox-Fetoprotein Gene Enhancers," Mol. Cell Biol., vol. 8, pp. 1169-1178 (Mar. 1988).
Goebel, et al., "The complete DNA sequence of vaccinia virus," Virology, vol. 179, No. 1, pp. 247-266 and 517-563 (Nov. 1990).
Golay, J., et al., "The Role of Complement in the Therapeutic Activity of Rituximab in a Murine B Lymphoma Model Homing in Lymph Nodes," Haematologica, vol. 91, No. 2, pp. 176-183 (Feb. 2006).
Gomella, L., et al., "Phase I study of intravesical vaccinia virus as a vector for gene therapy of bladder cancer," J Urol, vol. 166, No. 4, pp. 1291-1295 (Oct. 2001).

(56) References Cited

OTHER PUBLICATIONS

Goodbourn, S., et al., "The human β-interferon gene enhancer is under negative control," Cell, vol. 45, pp. 601-610 (May 23, 1986).
Goodbourn, S., et al., "Overlapping positive and negative regulatory domains of the human,8-interferon gene," Proc. Atl. Acad. Sci. USA, vol. 85, p. 1447-1451 (Mar. 1988).
Gopal, T., "Gene Transfer Method for Transient Gene Expression, Stable Transformation, and Cotransformation of Suspension Cell Cultures," Mol. Cell Biol,. Vol , pp. 1188-1190 (May 1985).
Graham, K., et al., "The T1/35kDa Family of Poxvirus-Secreted Proteins Bind Chemokines and Modulate Leukocyte Influx to Virus-Infected Tissues," Virology, vol. 229, No. 1, pp. 12-24 (Mar. 1997).
Graham, F. L., et al., "A new technique for the assay of infectivity of human adenovirus 5 DNA," Virology, vol. 52, No. 2, pp. 456-467 (Apr. 1973).
Greene, W., et al. "HIV-1, i1TLV-I and normal T-cell growth: transcriptional strategies and surprises," Immunology Today, vol. 10, pp. 272-278 (Aug. 1989).
Gross, A., et al., "BCL-2 family members and the mitochondria in apoptosis," Genes Dev, vol. 13, No. 15, pp. 1899-1911 (Aug. 1999).
Gross, et al., "Caspase Cleaved BID Targets Mitochondria and is Required for Cytochrome c Release, while BCL-XL Prevents This Release but Not Tumor Necrosis Factor-R1/Fas Death," J. Biol. Chem., vol. 274, No. 2, pp. 1156-1163 (Jan. 8, 1999).
Grosschedl, R., et al., "Cell-Type Specificity of Immunoglobulin Gene Expression is Regulated by at Least Three DNA Sequence Elements," Baltimore Cell, vol. 41, pp. 885-897 (Jul. 1985).
Guo, Z.S., et al., "The Enhanced Tumor Selectivity of an Oncolytic Vaccinia Lacking the Host Range and Antiapoptosis Genes SPI-1 and SPI-2," Cancer Res., vol. 65, No. 21, pp. 9991-9998, (Nov. 1, 2005).
Gulley, J., et al., "Pilot Study of Vaccination with Recombinant CEA-MUC-1-TRICOM Poxviral-Based Vaccines in Patients with Metastatic Carcinoma," Clin Cancer Res., vol. 14, No. 10, pp. 3060-3069 (May 2008).
Haanen, J., et al., "Melanoma-specific tumor-infiltrating lymphocytes but not circulating melanoma-specific T cells may predict survival in resected advanced-stage melanoma patients," Cancer Immunol. Immunother., vol. 55, No. 4, pp. 451-458 (Apr. 2006).
Hanibuchi, M., et al., "Therapeutic efficacy of mouse-human chimeric anti-ganglioside GM2 monoclonal antibody against multiple organ micrometastases of human lung cancer in NK cell-depleted SCID mice," Int J Cancer, vol. 78, No. 4, pp. 480-485 (Nov. 9, 1998).
Hanna, M.G., et al., "Histopathology of tumor regression after intralesional injection of Mycobacterium bovis., II. Comparative effects of vaccinia virus, oxazolone, and turpentine," J Natl Cancer Inst, vol. 48, Issue 6, pp. 1697-1707 (Feb. 22, 1972).
Harjunpaa, A., et al., Rituximab (anti-CD20) therapy of B-cell lymphomas: direct complement killing is superior to cellular effector mechanisms. Scand J Immunol. vol. 51, No. 6, pp. 634-641 (Jun. 5, 2000).
Harland, R., et al., "Translation of mRNA injected into Xenopus oocytes is specifically inhibited by antisense RNA," J Cell Biol., vol. 101, No. 3, pp. 1094-1099 (Sep. 1985).
Haslinger, A., et al., "Upstream promoter element of the human metallothionein-IIA gene can act like an enhancer element," Natl. Acad. Sci. USA, vol. 82, pp. 8572-8576 (Dec. 1985).
Hauber, J., et al., "Mutational Analysis of the trans-Activation-Responsive Region of the Human Immunodeficiency Virus Type I Long Terminal Repeat," J. Virology, vol. 62, No. 3, pp. 673-679 (Mar. 1988).
Hawkins, L., et al., "Oncolytic biotherapy: a novel therapeutic platform," Lancet Oncol, vol. 3. No. 1, pp. 17-26 (Jan. 2002).
He, Z., et al., "Viral recombinant vaccines to the E6 and E7 antigens of HPV-16," Virology, vol., 270, No. 1, pp. 146-161 (Apr. 25, 2000).
Heise, C., et al., "An Adenovirus E1A Mutant That Demonstrates Potent and Selective Antitumoral Efficacy," Nature Medicine, vol. 6, No. 10., pp. 1134-1139 (Oct. 2000).
Heise, C., et al, Intravenous Administration of ONYX-015, a Selectively Replicating Adenovirus, Induces Antitumoral Efficacy: Cancer Res., vol. 59, No. 11, pp. 2623-2628 (Jun. 1, 1999).
Heise, C., et al., "Efficacy of a replication-competent adenovirus (ONYX-015) following intratumoral injection: intratumoral spread and distribution effects," Cancer Gene Ther., vol. 6, No. 6, pp. 499-504 (Jun. 1, 1999).
Heise, C., et al., "ONYX-015, an E1B gene-attenuated adenovirus, causes tumor-specific cytolysis and antitumoral efficacy that can be augmented by standard chemotherapeutic agents," Nat Med, vol. 3, No. 6, pp. 639-645 (Jun. 1997).
Hellstrand, K., et al., "Histamine and Cytokine Therapy: Paper presented at the annual meeting of the Swedish Oncology Society, Stockholm, 1997," Acta Oncològica 37, No. 4, pp. 347-353 (1988).
Hen, R., et al., "A mutated polyoma virus enhancer which is active in undifferentiated embryonal carcinoma cells is not repressed by adenovirus-2 E1A products," Nature, vol. 32, pp. 249-251 (May 1986).
Hengstschlager, M., et al., Different Regulation of Thymidine Kinase During the Cell Cycle of Normal Versus DNA Tumor Virus-Transformed Cells., J. Biol. Chem., vol. 269, pp. 13836-13842 (May 13, 1994).
Hensel, G., et al., "PMA-responsive 5' flanking sequences of the human TNF gene," Llymphokine Res., vol. 8, No. 3, pp. 347-351 (Fall 1989).
Heo, J., et al., "Randomized Dose-Finding Clinical Trial of Oncolytic Immunotherapeutic Vaccina JX-594 in Liver Cancer," Nature Medicine, vol. 19, No. 3, pp. 329-336 (Mar. 2013).
Heo, J., et al., "Evaluating Antivascular Effects and Antitumoral Activity in Patients with Hepatocellular Carcinoma Treated with JX-594, a Targeted Multimechanistic Oncolytic Poxvirus, Prior to Sorafenib Therapy, ASCO Meeting Abstracts," Journal of Clinical Oncology, vol. 28, No. 15 Sup., p. e14564 (May 1, 2010).
Hermiston, T., "Gene delivery from replication-selective viruses: arming guided missiles in the war against cancer," J Clin Invest, 105:1169-1172 (May 2000).
Higano, C., et al., "Integrated data from 2 randomized, double-blind, placebo-controlled, phase 3 trials of active cellular immunotherapy with sipuleucel-T in advanced prostate cancer," Cancer, vol. 115, No. 16, pp. 3670-3679 (Aug. 15, 2009).
Ho., Y., et al., "Reduced Fertility in Female Mice Lacking Copper-Zinc Superoxide Dismutase," J. Biol. Chem., vol. 27, No. 13, pp. 7765-7769 (Mar. 27, 1998).
Holzer, G., et al., "Highly efficient induction of protective immunity by a vaccinia virus vector defective in late gene expression," Journal of Virology, vol. 73, No. 6, pp. 4536-4542 (Jun. 1999).
Homey, G., et al., "Chemokines: Agents for the Immunotherapy of Cancer?" Nature Rev Immunol, vol. 2, No. 3, pp. 175-184 (Mar. 2002).
Hui, G., et al., "Pathways for potentiation of immunogenicity during adjuvant-assisted immunizations with Plasmodium falciparum major merozoite surface protein 1," Infect Immun, vol. 66, No. 11, pp. 5329-5336 (Nov. 1998).
Hussussian, C., et al., "Germline p16 mutations in familial melanoma," Nat. Genet., vol. 8, No. 1, pp. 15-21 (Sep. 1994).
Ikeda, K., et al., "Oncolytic virus therapy of multiple tumors in the brain requires suppression of innate and elicited antiviral responses," Nat Med, vol. 5, No. 8, pp. 881-887 (Aug. 1999).
Inouye , S., et al., "Up-promoter mutations in the lpp gene of Escherichia coli," Nucleic Acids Res. vol. 13, pp. 3101-3109 (May 10, 1985).
International Preliminary Report on Patentability of PCT/US12/20173 dated Jul. 10, 2013.
International Search Report of PCT/US12/20173 dated Apr. 13, 2012.
International Search Report of PCT/US03/25141 dated Jul. 27, 2009.
International Preliminary Report on Patentability of PCT/US2006/034945 dated Mar. 11, 2008.
International Preliminary Report on Patentability of PCT/US2008/057257 dated Sep. 15, 2009.
International Preliminary Report on Patentability of PCT/US2010/48829 dated Mar. 20, 2012.
International Search Report of PCT/US2003/025141 dated Jul. 27, 2009.
International Search Report of PCT/US2006/034945 dated Mar. 23, 2007.

(56) References Cited

OTHER PUBLICATIONS

International Search Report of PCT/US2008/057257 dated Aug. 15, 2008.
International Search Report of PCT/US2010/48829 dated Dec. 16, 2010.
Irie, R., et al., "Regression of cutaneous metastatic melanoma by intralesional injection with human monoclonal antibody to ganglioside GD2," Proc. Natl. Acad. Sci, USA, vol. 83, No. 22, pp. 8694-8698 (Nov. 1986).
Irie, R., et al., "Human monoclonal antibody to ganglioside GM2 for melanoma treatment," Lancet., vol. 1, No. 8641, pp. 786-787 (Apr. 1989).
Isaacs, S., et al., "Vaccinia virus complement-control protein prevents antibody-dependent complement-enhanced neutralization of infectivity and contributes to virulence," Proc. Natl. Acad. Sci. USA, vol. 89, No. 2, p. 628-32 (Jan. 1992).
Johnson, M ., et al., "Apoptosis regulating genes in prostate cancer (review)," Oncol. Rep., vol. 5, No. 3, pp. 553-557 (May 1, 1998).
Ju, D., et al., "Interleukin-18 gene transfer increases antitumor effects of suicide gene therapy through efficient induction of antitumor immunity," Gene Ther., vol. 7, No. 19, pp. 1672-1679 (Jul. 2000).
Ju, W., et al., "Selective Neuronal Survival and Upregulation of PCNA in the Rat Inner Retina Following Transient Ischemia," J Neuropathol. Exp. Neurol., vol. 59, No. 3, pp. 241-250 (Mar. 2000).
Kaeppler, H., et al., "Silicon carbide fiber-mediated DNA delivery into plant cells," Plant Cell Reports, vol. 9, pp. 415-418 (Dec. 1990).
Kamb, A., et al., "Analysis of the p16 gene (CDKN2) as a candidate for the chromosome 9p melanoma susceptibility locus," Nat. Genet., vol. 8, No. 1, pp. 22-26 (Sep. 1994).
Kamb, A., et al., "A cell cycle regulator potentially involved in genesis of many tumor types," Science, vol. 264, No. 5157, pp. 436-440 (Apr. 15, 1994).
Kaneda, Y., et al., "Increased expression of DNA cointroduced with nuclear protein in adult rat liver," Science, vol. 243, pp. 375-378 (Jan. 1989).
Kantor, J., et al., "Antitumor activity and immune responses induced by a recombinant carcinoembryonic antigen-vaccinia virus vaccine," J Natl Cancer Inst, vol. 84, No. 14, pp. 1084-1091 (Apr. 21, 1992).
Kato, J., et al., "Cyclic GMP Down-regulates Atrial Natriuretic Peptide Receptors on Cultured Vascular Endothelial Cells," J Biol Chem., vol. 266, No. 22, pp. 3361-3364 (Aug. 5, 1991).
Kaufman, H., et al., "Local and Distant Immunity Induced by intralesional vaccination with an oncolytic herpes virus encoding GM-CSF in patients with stage IIIc and IV melanoma," Ann Surg Oncol., vol. 17, No. 3, pp. 718-730 (Mar. 2010).
Kawakita, M., et al., "Poxvirus vectors for gene transfer," Acta Urologica Japonica, vol. 43, No. 11, pp. 835-838 (Nov. 1997).
Kay, M., et al., "Transient immunomodulation with anti-CD40 ligand antibody and CTLA4lg enhances persistence and secondary adenovirus-mediated gene transfer into mouse liver," Proc Natl Acad Sci USA, vol. 97, No. 9, pp. 4686-4691 (Apr. 1997).
Kerr, J., et al., "Apoptosis: A Basic Biological Phenomenon With Wideranging Implications in Tissue Kinetics," Br. J. Cancer, vol. 26, No. 4, pp. 239-257 (Apr. 1972).
Kerr, D., "Clinical Development of Gene Therapy for Colorectal Cancer," Nat. Rev. Cancer, vol. 3, No. 8, pp. 615-622 (Aug. 2003).
Kettle, S., et al., "Vaccinia virus serpin B13R (SPI-2) inhibits interleukin 1-beta converting enzyme and protects virus-infected cells from TNF- and Fas-mediated apoptosis, but does not prevent IL-1-beta induced fever," J. Gen. Vir., vol. 78, pp. 677-685 (Mar. 1997).
Kim, J., et al., "167. Both Oncolysis and Tumor Immunity are Involved in an Antitumoral Efficacy by Intratumoral Injection of Recombinant Vaccinia Virus (TK Deleted, hGM-CSF Inserted Wyeth Strain) in a VX2 Rabbit Model," Mol. Therapy, vol. 11, Supplement 1, p. S67 (May 2005).
Kim, J., et al., Abstract No. 168: Antitumoral Efficacy of Multiple Injection of JX-594 (Thymidine Kinase (TK) Deleted, Human GM-CSF Inserted Wyeth Strain) Via Tail Vein in NNitrosomorpholine (NNM) Treated Rats), Molecular Therapy, vol. 11, Supplement 1, p. S67 (May 2005).
Kim, J., et al., "Systemic Armed Oncolytic and Immunologic Therapy for Cancer with JX-594, A Targeted Poxvirus Expressing GM-CSF," Mol. Ther., vol. 14, No. 3, pp. 361-370 (Sep. 14, 2006).
Kirn, D., et al., "Targeted and Armed Oncolytic Poxviruses: A Novel Multi-Mechanistic Therapeutic Class for Cancer," Nature, vol. 9, pp. 64-71 (Jan. 2009).
Kirn, D., et al., "Replication-selective virotherapy for cancer: biological principles, risk management and future direction," Nat Med, vol. 7, No. 7, pp. 781-787 (Jul. 2001).
Kirn, D. et al., "Targeting of Interferon-Beta to Produce a Specific, Multi-Mechanistic Oncolytic Vaccinia Virus," PLoS Med., vol. 4, No. 12, e353 (Dec. 2007).
Kirn, D., et al., "Systemic Oncolytic and Immunologic Therapy for Cancer with JX-594, a Targeted Poxvirus Expressing GM-CSF," Mol. Ther., vol. 13, Supplement 1, pp. S244-S245 (May 2006).
Kirn, D., et al., "The emerging fields of suicide gene therapy and virotherapy," Trends Mol Med, vol. 8, No. 4, pp. S68-S73 (Apr. 1, 2002).
Kolmel, H., "Cytology of neoplastic meningosis," J. Neurooncol., vol. 38, No. 2-3, pp. 121-125 (Jun. 1998).
Kraus, J., et al., "Alternative promoter usage and tissue specific expression of the mouse somatostatin receptor 2 gene," FEBS Lett., vol. 428, No. 3, pp. 165-170 (Apr. 21, 1998).
Kulesh, D., et al., "Smallpox and pan-Orthopox Virus Detection by Real-Time 3—Minor Groove Binder TaqMan Assays on the Roche LightCycler and the Cepheid Smart Cycler Platforms," J. Clin. Microbiol., vol. 42, No. 2, pp. 601-609 (Feb. 2004).
Kurata, H., et al., "Recombinant adenovirus vectors for cytokine gene therapy in mice," J. Allergy Clin. Immunol., vol. 103, Issue 5, Supplement, Pt. 2, pp. S471-S484 (May 1999).
Kyte, J., et al., "A simple method for displaying the hydropathic character of a protein," J. Mol. Biol., vol. 157, No. 1, pp. 105-132 (May 5, 1982).
Lareyre, J., et al., "A 5-Kilobase Pair Promoter Fragment of the Murine Epididymal Retinoic Acid-binding Protein Gene Drives the Tissue-specific, Cell-specific, and Androgen-regulated Expression of a Foreign Gene in the Epididymis of Transgenic Mice," J. Biol. Chem., vol. 274, No. 12, pp. 8282-8290 (Mar. 19, 1999).
Law, M., et al., "Antibody-sensitive and antibody-resistant cell-to-cell spread by vaccinia virus: role of the A33R protein in antibody-resistant spread," J Gen Virol., vol. 83, Pt 1, pp. 209-222 (Jan. 2002).
Lee, J., et al., "Oncolytic and Immunostimulatory Efficacy of a Targeted Oncolytic Poxvirus Expressing Human GM-CSF Following Intravenous Administration in a Rabbit Tumor Model," Cancer Gene Ther., vol. 17, No. 2, pp. 73-79 (Feb. 2010).
Lee, J., et al., "406. Enhanced Vaccinia-meditated Antitumor Response after Specific Inhibition of the Cellular Immune Response," Mol. Ther., vol. 1, No. 5, Part 2 of 2, pp. S156-S157 (May 2000).
Lee, J., et al., "The Highly Basic Ribosomal Protein L41 Interacts with the b Subunit of Protein Kinase CKII and Stimulates Phosphorylation of DNA Topoisomerase IIa by CKII," Biochem. Biophys. Res. Commun., vol. 238, No. 2, pp. 462-467 (Jul. 29, 1997).
Legrand, F., et al., "Vaccinia viruses with a serpin gene deletion and expressing IFN-γ induce potent immune responses without detectable replication in vivo," PNAS, vol. 102, No. 8, pp. 2940-2945, (Feb. 2005).
Le Tourneau, C., et al., "New Developments in Multitargeted Therapy for Patients with Solid Tumours," Cancer Treat Rev., vol. 34, Issue 1, pp. 3748 (Feb. 2008).
Levenson, V., et al., "Internal Ribosomal Entry Site-Containing Retroviral Vectors with Green Fluorescent Protein and Drug Resistance Markers," Hum. Gene Ther., vol. 9, No. 8, pp. 1233-1236 (May 20, 1998).
Li, C., et al., Cytokine and Immuno-Gene Therapy for Solid Tumors, Cellular & Molecular Immunology, vol. 2, No. 2, pp. 81-91 (Apr. 2005).
Li, Q.X., et al., "Oncolytic Virotherapy as a Personalized Cancer Vaccine," Int. J Cancer, vol. 123, No. 3, pp. 493-499 (Aug. 1, 2008).

(56) References Cited

OTHER PUBLICATIONS

Li, H., et al., "Induction of Strong Antitumor Immunity by an HSV-2-Based Oncolytic Virus in a Murine Mammary Tumor Model," J Gene Med., vol. 9, No. 3, pp. 161-169 (Mar. 2007).
Liebermann, D., "Normal development, oncogenesis and programmed cell death," Oncogene, vol. 17, No. 10, pp. 1189-1894 (Aug. 4, 1998).
Liu, T., et al., "The Targeted Oncolytic Poxvirus JX-594 Demonstrates Antitumoral, Antivascular, and Anti-HBV Activities in Patients with Hepatocellular Carcinoma," Molecular Therapy, vol. 16, No. 9, pp. 1637-1642 (Jul. 2008).
Liu, Z., et al., "Cytokine Enhancement of In Vitro Antibody-Dependent Cellular Cytotoxicity Mediated by Chimeric Anti-GD3 Monoclonal Antibody KM871," Cancer Immun., vol. 2, No. 13, pp. (Oct. 2002).
Liu, T., et al., "Translation of Targeted Oncolytic Virotherapeutics From the Lab into the Clinic, and Back Again: A High-Value Iterative Loop," Mol. Ther., vol. 16, No. 6, pp. 1006-1008 (Jun. 2008).
Liu, T., et al., "Clinical Trial Results with Oncolytic Virotherapy: A Century of Promise, a Decade of Progress," Nature Clinical Practice Oncology, vol. 4, No. 2, pp. 101-117, (Jan. 1, 2007).
Llovet, J., "Supplementary Appendix to Sorafenib in Advanced Hepatocellular Carcinoma (HCC)." N. Engl. J. Med., vol. 359, pp. 378 390 (Jul. 24, 2008).
Loparev, V., et al., "A third distinct tumor necrosis factor receptor of orthopoxviruses," Proc Natl Acad Sci USA, vol. 95, pp. 3789-3791 (Mar. 1998).
Macejak, D., et al., "Internal initiation of translation mediated by the 5' leader of a cellular mRNA," Nature, vol. 353, pp. 90-94 (Sep. 1991).
Magi-Galluzzi, C., et al., "Proliferation, apoptosis and cell cycle regulation in prostatic carcinogenesis," Anal. Quant. Cytol. Histol., vol. 20, No. 5, pp. 343-250 (Oct. 1998).
Mahvi, D., et al., "Phase I/IB study of immunization with autologous tumor cells transfected with the GM-CSF gene by particle-mediated transfer in patients with melanoma or sarcoma," Human Gene Therapy, vol. 5, pp. 875-891 (May 1997).
Mangray, S., et al., "Molecular Pathobiology of Pancreatic Adenocarcinoma," Front Biosci., vol. 3, pp. D1148-D1116 (Nov. 15, 1998).
Marshall, J., et al., "Phase I study in advanced cancer patients of a diversified prime-and-boost vaccination protocol using recombinant vaccinia virus and recombinant nonreplicating avipox virus to elicit anti-carcinoembryonic antigen immune responses," J Clin Oncol, vol. 18, No. 23, pp. 3964-3973 (Dec. 2000).
Marsters, S., et al., "Control of apoptosis signaling by Apo2 ligand," Recent Prog. Horm. Res., vol. 54, pp. 225-234 (Annual Publication—1999).
Mastrangelo, M., et al., "Virotherapy clinical trials for regional disease: in situ immune modulation using recombinant poxvirus vectors," Cancer Gene Ther., vol. 9, pp. 1013-1021 (Sep. 16, 2002).
Mastrangelo, M., et al., "Intralesional Vaccinia/GM-CSF Recombinant Virus in the Treatment of Metastatic Melanoma," Adv. Exp. Med. Biol., vol. 465, pp. 391-400 (Apr. 30, 2000).
Mastrangelo, M., et al., "Intratumoral recombinant GM-CSF-encoding virus as gene therapy in patients with cutaneous melanoma," Cancer Gene Ther., vol. 6, pp. 409-422 (Sep./Oct. 1998).
Mastrangelo, M., et al., "Cellular vaccine therapies for cancer," Cancer Treat Res., vol. 94, pp. 35-50 (Annual Publication—1998).
Mathew, et al., "A mutational analysis of the vaccinia virus B5R protein," J Gen Virol., vol. 82, pp. 1199-1213 (May 2001).
Mathew, E., et al., "The Extracellular Domain of Vaccinia Virus Protein B5R Affects Plaque Phenotype, Extracellular Enveloped Virus Release, and Intracellular Actin Tail Formation," J. Virol. vol. 72, No. 3, pp. 2429-2438 (Mar. 1998).
Mayer, R., et al., "CT Number Distribution and Its Association With Local Control and as a Marker of Lung Tumor Response to Radiation," Radiat. Oncol. Investig., vol. 6, No. 6, pp. 281-288 (Sep. 1998).
McCart, J., et al., "Complex interactions between the replicating oncolytic effect and the enzyme/prodrug effect of vaccinia-mediated tumor regression," Gene Ther, vol. 7, No. 14, pp. 1217-1223 (Jul. 2000).
McCart, J, et al., "Systemic cancer therapy with a tumor-selective vaccinia virus mutant lacking thymidine kinase and vaccinia growth factor genes," Cancer Res, vol. 61, pp. 8751-8757 (Dec. 2001).
McCormick, F., "Cancer Gene Therapy: Fringe or Cutting Edge?" Nature, vol. 1, pp. 130-141 (Nov. 2001).
McDonald, C., et al., "Synergistic actions of oncolytic vaccinia virus and sunitinib on pancreatic neuroendocrine tumors in RIP-Tag2 mice," American Association for Cancer Research Annual Meeting 2015—Apr. 18-22 Philadelphia—Abstract—on-line publication http://www.abstractsonline.com/plan/ViewAbstract.
aspx?mID=3682&sKey=c0f97126-ef0e-4d5f-875e-5fb8501051
b6&cKey=253ff688-75df-4eb9-8a72-d81af896c326&mKey=
19573a54-ae8f-4e00-9c23-bd6d62268424.
McFadden, G., et al., "Host-related immunomodulators encoded by poxviruses and herpesviruses," Curr Opin Microbiol, vol. 3, Issue 4, pp. 371-378 (Aug. 7, 2000).
McIntosh, A., et al., "Vaccinia virus glycoprotein A34R is required for infectivity of extracellular enveloped virus," J. Virol., vol. 70, pp. 272-228 (Jan. 1996).
Mineta, T., et al., "Attenuated Multi-Mutated Herpes Simplex Virus-1 for the Treatment of Malignant Gliomas," Nat Med., vol. 1, No. 9, pp. 938-943 (Sep. 1995).
Mineta, T., et al., "Treatment of Malignant Gliomas Using Ganciclovir-Hypersensitive, Ribonucleotide Reductase-Deficient Herpes Simplex Viral Mutant," Cancer Res., vol. 54, No. 15, pp. 3963-3966 (Aug. 1994).
Mitchell, M., et al., "Active-specific immunotherapy for melanoma," J. Clin. Oncol., vol. 8, No. 5, pp. 856-869 (May 1990).
Mitchell, M., et al., "Active Specific Immunotherapy of Melanoma with Allogeneic Cell Lysates Rationale, Results, and Possible Mechanisms of Action," Ann. NY Acad. Sci., vol. 690, pp. 153-166 (Aug. 1993).
Mori, T., et al., "Frequent Somatic Mutation of the MTS1/CDK4I (Multiple Tumor SuppressorlCyclin-dependent Kinase 4 Inhibitor) Gene in Esophageal Squamous Cell Carcinoma'," Cancer Res., vol. 54, No. 13, pp. 3396-3397 (Jul. 1994).
Morris, J., et al., "Antibody-Based Therapy of Leukaemia," Expert Rev Mol Med., vol. 11, No. e29 (Sep. 2009).
Morton, D., et al., "Technical details of intraoperative lymphatic mapping for early stage melanoma," Arch. Surg., vol. 127 pp. 392-399 (Apr. 1992).
Moss, B., Fields Virology., Fifth Edition, Lippincott-Raven Publishers: Philadelphia, pp. 2905-2945 (2007).
Moss, "Chapter 37: Poxviridae and Their Replication," Fundamental Virology, Second Edition, Fields et al. (ed.), Raven Press Publ, New York, pp. 953-985 (1996).
Mossman, K., et al., "Myxoma virus M-T7, a secreted homolog of the interferon-gamma receptor, is a critical virulence factor for the development of myxomatosis in European rabbits," Virology, vol. 215, No. 1, pp. 17-30, (Jan. 1996).
Motzer, R. J., et al., "Sunitinib in Patients with Metastatic Renal Cell Carcinoma," JAMA, vol. 295, No. 21, pp. 2516-2524 (Jun. 7, 2006).
Mougin, C., et al., "Biology of papillomavirus infections. II. Their role in cervical carcinogenesis," Ann. Bol. Clin., (Paris), vol. 56, No. 1, pp. 21-28 (Jan.-Feb. 1998).
Mukherjee, S., et al., "Replication-restricted vaccinia as a cytokine gene therapy vector in cancer: persistent transgene expression despite antibody generation," Cancer Gene Ther, vol. 7, No. 5, pp. 663-670 (May 2000).
Mullen, J., et al., "Viral Oncolysis," The Oncologist, vol. 7, No. 2, pp. 106-119 (Jan. 2002).
Mumby, M., et al., "Protein phosphatases and DNA tumor viruses: transformation through the back door?" Cell Regul., vol. 2, No. 8, pp. 589-598 (Aug. 1991).
Natoli, G., et al., "Apoptotic, Non-apoptotic, and Anti-apoptotic Pathways of Tumor Necrosis Factor Signalling," Biochem. Pharmacol., vol. 56, No. 8, pp. 915-920 (Oct. 15, 1998).
NCT 01171651 on Jul. 27, 2010, ClinicalTrials.gov Archive pp. 1-4 (Jul. 27, 2010).

(56) References Cited

OTHER PUBLICATIONS

Ng, A., et al., "The vaccinia virus A41L protein is a soluble 30 kDa glycoprotein that affects virus virulence," J Gen Virol., vol. 82, pp. 2095-2105 (Sep. 2001).
Nicolau, C., et al., "Liposome-mediated DNA transfer in eukaryotic cells: Dependence of the transfer efficiency upon the type of liposomes used and the host cell cycle stage," Biochem. Biophys. Acta, vol. 721, pp. 185-190 (Oct. 11, 1982).
Nielsen, L., et al., "Adenovirus-mediated p53 gene therapy and paclitaxel have synergistic efficacy in models of human head and neck, ovarian, prostate, and breast cancer," Clin Cancer Res, vol. 4, No. 4, pp. 835-846 (Apr. 1998).
Nielsen, L., et al., "Adenovirus-mediated p53 therapy synergizes with paclitaxel against human ovarian, mammary, prostate, head and neck, and liver cancer," Cancer Gene Therapy, vol. 4, No. 6, pp. S12 (Apr. 1997).
Noguiez-Hellin, P., et al., "Plasmoviruses: Nonviral/viral vectors for gene therapy," Proc. Natl. Acad. Sci. USA, vol. 93, pp. 4175-4180 (Apr. 1996).
Nomoto, S., et al., "Cloning and characterization of the alternative promoter regions of the human LIMK2 gene responsible for alternative transcripts with tissue-specific expression," Gene, vol. 236, No. 2, pp. 259-271 (Jun. 24, 1999).
Norman, K., et al., "Reovirus as a Novel Oncolytic Agent," J Clin. Invest., vol. 105, No. 8, pp. 1035-1038 (Apr. 2000).
Ochi, K, et al., "A Case of Small Pancreatic Cancer Diagnosed by Serial Follow-up Studies Promptly by a Positive K-ras Point Mutation in Pure Pancreatic Juice," Am. J. Gastroenterol., vol. 93, No. 8, pp. 1366-1368 (Mar. 6, 1998).
Ohara, K., "Radiotherapy: a significant treatment option in management of prostatic cancer," Gan to Kagaku Ryoho, vol. 25, No. 6, pp. 823-828 (May 1998).
Okamoto, A., et al., "Mutations and altered expression of p16INK4 in human cancer (p53 protein/tumor-suppressor gene/cyclin Di/retinoblastoma protein)," Proc. Natl. Acad. Sci. USA, vol. 9, No. 23, pp. 1104-1109 (Nov. 1994).
Omirulleh, S., et al., "Activity of a chimeric promoter with the doubled CaMV 35S enhancer element in protoplast-derived cells and transgenic plants in maize," Plant Mol. Biol., vol. 21, No. 3, pp. 415-428 (Feb. 1993).
Orlow, I., et al., "Chromosome 9 Allelic Losses and Microsatellite Alterations in Human Bladder Tumors," Cancer Res., vol. 54, No. 11, pp. 2848-2851 (Jun. 1, 1994).
Parato, K.A., et al., "Diplomatic Immunity: Turning a Foe Into an Ally," Curr Opin Mol Ther., vol. 11, No. 1, pp. 13-21 (Feb. 2009).
Parato, K. et al., "Recent Progress in the Battle between Oncolytic Viruses and Tumours," Nat Rev Cancer, vol. 5, pp. 965-976 (Dec. 2005).
Park, B.H., et al., "Use of a Targeted Oncolytic Poxvirus, JX-594, in Patients with Refractory Primary or Metastatic Liver Cancer: A Phase I Trial." Lancet Oncology, vol. 9, pp. 533-542 (Jun. 2008).
Payne, L., "Significance of Extracellular Enveloped Virus in the In Vitro and In Vivo Dissemination of Vaccinia," J Gen Virol., vol. 50, No. 1, pp. 89-100 (Sep. 1980).
Payne, L., "Identification of the Vaccinia Hemagglutinin Polypeptide from a Cell System Yielding Large Amounts of Extracellular Enveloped Virus," Journal of Virology, vol. 31, No. 4, pp. 147-155 (Jul. 1979).
Pelletier J., et al., "Internal initiation of translation of eukaryotic mRNA directed by a sequence derived from poliovirus RNA," Nature, vol. 334, No. 6180, pp. 320-325 (Jul. 1988).
Peplinski, G., et al., "In vivo gene therapy of a murine pancreas tumor with recombinant vaccinia virus encoding human interleukin-1beta," Surgery, vol. 118, Issue 2, pp. 185-191 (Aug. 1995).
Perera, L., et al., "Comparative assessment of virulence of recombinant vaccinia viruses expressing IL-2 and IL-15 in immunodeficient mice," PNAS, vol. 98, No. 9. pp. 5146-5151 (Feb. 2001).
Petrelli A., et al., "From Single-to Multi-Target Drugs in Cancer Therapy: When Aspecificity Becomes an Advantage," Current Medical Chemistry, vol. 15, pp. 422-432 (Feb. 2008).

Pietras, R., et al., "Remission of human breast cancer xenografts on therapy with humanized monoclonal antibody to HER-2 receptor and DNA-reactive drugs," Oncogene, vol. 17, No. 17, pp. 2235-2249 (May 1998).
Podar, K., et al., "The Small-Molecule VEGF Receptor Inhibitor Pazopanib (GW786034B) Targets Both Tumor and Endothelial Cells in Multiple Myeloma," Proc. Natl. Acad. Sci. U S A., vol. 103, No. 51, pp. 19478-19483 (Dec. 19, 2006).
Prestwich, R., et al., "Immune-mediated antitumor activity of reovirus is required for therapy and is independent of direct viral oncolysis and replication," Clin. Cancer Res., vol. 15, No. 13, pp. 4374-4381 (Jul. 1, 2009).
Price, N., et al. "The vaccinia virus B9R protein is a 6 kDa intracellular protein that is non-essential for virus replication and virulence," J Gen Virol., vol. 83, Pt 4, pp. 873-878 (Apr. 2002).
Price, N., et al., "Vaccinia virus gene B7R encodes an 18-kDa protein that is resident in the endoplasmic reticulum and affects virus virulence," Virology, vol. 267, pp. 65-79 Feb. 1, 2000).
Puhlmann M., et al., "Thymidine Kinase-Deleted Vaccinia Virus Expressing Purine Nucleoside Phosphorylase as a Vector for Tumor-Directed Gene Therapy," Hum Gene Ther., vol. 10, pp. 649-657 (Mar. 1, 1999).
Puhlmann, M., et al., "Vaccinia as a vector for tumor-directed gene therapy: biodistribution of a thymidine kinase-deleted mutant," Cancer Gene Ther., vol. 7, No. 1, pp. 66-73 (Jan. 2000).
Qin, H., et al., "Cancer Gene Therapy Using Tumor Cells Infected with Recombinant Vaccinia Virus Expressing GM-CSF," Human Gene Therapy, vol. 7, pp. 1853-1860 (Oct. 1, 1996).
Qin, X., et al., "Interferon-beta gene therapy inhibits tumor formation and causes regression of established tumors in immune-deficient mice," Proc Natl Acad Sci USA, vol. 95, No. 24, pp. 4411-14416 (Nov. 1998).
Racila, E., et al., "A polymorphism in the Complement Component C1qA Correlates with Prolonged Response Following Rituximab Therapy of Follicular Lymphoma," Clin Cancer Res., vol. 14, No. 20, pp. 6697-6703 (Oct. 15, 2008).
Randall, R., et al., "Interferons and Viruses: An Interplay Between Induction, Signalling, Antiviral Responses and Virus Countermeasures," Journal of General Virology, vol. 89, pp. 1-47 (Jan. 2008).
Ravindranath, M., et al., "Role of Gangliosides in Active Immunotherapy with Melanoma Vaccine," Intern. Rev. Immunol., vol. 7, pp. 303-329 (Apr. 26, 1991).
Reading, P., et al., "Vaccinia virus CrmE encodes a soluble and cell surface tumor necrosis factor receptor that contributes to virus virulence," Virology, vol. 292, No. 2, pp. 285-298 (Jan. 2002).
Reagan-Shaw, S., et al., "Dose Translation From Animal to Human Studies Revisited," FASEB Journal, vol. 22, pp. 659-661 (Mar. 2008) (E-published Oct. 2007).
Reid, T., "Fighting Fire with Fire: Effects of Oncolytic Virotherapy on Underlying Viral Hepatitis in Hepatocellular Carcinoma," Molecular Therapy, vol. 16, No. 9, pp. 1521-5123 (Sep. 1, 2008).
Remington's Pharmaceutical Sciences, 18th Edition, "Chapter 52 Enzymes and Chapter 85 Intravenous Admixtures," published Philadelphia, pp. 1035-1038 and 1570-1580 (1990).
Rippe, R., et al., "DNA-Mediated Gene Transfer into Adult Rat Hepatocytes in Primary Culture," Mol. Cell Biol., vol. 10, pp. 689-695 (Feb. 1990).
Rosel, J., et al., "Conserved TAAATG sequence a the transcriptional and translational initiation sites of vaccinia virus late genes deduced by structural and functional analysis of the HindIII H genome fragment," J Virology, vol. 60, No. 2, pp. 436-449 (Jul. 1986).
Rosenberg, S., et al., "Use of tumor-infiltrating lymphocytes and interleukin-2 in the immunotherapy of patients with metastatic melanoma. A preliminary report," N. Engl. J. Med., vol. 319., pp. 1676-1680 (Dec. 1988).
Rosenberg, S., et al., "Experience with the Use of High-Dose Interleukin-2 in the Treatment of 652 Cancer Patients," Ann. Surg., vol. 210, No. 4, pp. 474-548 (Apr. 17, 1989).
Rosenberg, S., et al., "Cancer Immunotherapy: Moving Beyond Current Vaccines," Nature Medicine, vol. 10, No. 9, pp. 909-915 (Sep. 2004).

(56) References Cited

OTHER PUBLICATIONS

Sambrook, J., et al., Chapter 9—Molecular Cloning: A Laboratory Manual, 2nd Edition, Cold Spring Harbor, Laboratory Press, Cold Spring Harbor, New York, pp. 4.13-4.19 (1989).

Sandhu, D., et al., "Treatment Options for Hepatocellular Carcinoma," Expert Review of Gastroenterology & Hepatology, vol. 2, No. 1, pp. 81-92 (Feb. 2008).

Saraiva, M., et al., "CrmE, a novel soluble tumor necrosis factor receptor encoded by poxviruses," J Virol, vol. 75, No. 1, pp. 226-233 (Jan. 2001).

Schmitz, V., et al., "Gene therapy for liver diseases: recent strategies for treatment of viral hepatitis and liver malignancies," Gut, vol. 50, pp. 130-135 (Jan. 2002).

Scholl, S., et al., "Recombinant vaccinia virus encoding human MUC1 and IL2 as immunotherapy in patients with breast cancer," J Immunother, vol. 23, Issue 5, pp. 570-580 (Sep./Oct. 2000).

Seet, B., et al., "Molecular determinants for CC-chemokine recognition by a poxvirus CC-chemokine inhibitor," Proc Natl Acad. Sci USA, vol. 98, No. 16, pp. 9008-9013, (Jul. 2001).

Senzer, N., et al., "Phase II Clinical Trial of a Granulocyte-macrophage Colony-Stimulating Factor-Encoding, Second-Generation Oncolytic Herpesvirus in Patients with Unresectable Metastatic Melanoma," J Clin Oncol, vol. 27, No. 34, pp. 5763-5771 (Dec. 1, 2009).

Serrano, M., et al., "A new regulatory motif in cell-cycle control causing specific inhibition of cyclin D/CDK4," Nature, vol. 366, pp. 704-707 (Dec. 1993).

Serrano, M., et al., "Inhibition of ras-induced proliferation and cellular transformation by p16INK4," Science, vol. 267, No. 5195, pp. 249-252 (Jan. 13, 1995).

Siemens, D., et al., "Comparison of Viral Vectors: Gene Transfer Efficiency and Tissue Specificity in a Bladder Cancer Model" Journal of Urology, vol. 170, No. 3, pp. 979-984 (Sep. 2003).

Sinkovics, J., et al., "Newcastle disease virus (NDV): brief history of its oncolytic strains," J Clin Viro, vol. 16, pp. 1-15 (Feb. 2000).

Sinkovics, J., "New Developments in the Virus Therapy of Cancer: A Historical Review," Intervirology, vol. 36, pp. 193-214 (1993).

Smith, G., et al., "Extracellular enveloped vaccinia virus," Adv Exp Med Biol, vol. 440, pp. 395-414 (Aug. 31, 1998).

Smith, G., "Vaccinia virus immune evasion," Immunol Lett., vol. 65, Issue 1-2, pp. 55-62 (Jan. 1999).

Smith, G., et al., "Corticotropin releasing factor receptor 1-deficient mice display decreased anxiety, impaired stress response, and aberrant neuroendocrine development," Neuron., vol. 20, pp. 1093-1102 (Jun. 1998).

Smith, V., et al., "Ectromelia, vaccinia and cowpox viruses encode secreted interleukin-18-binding proteins," J. Gen. Virol., vol. 81, pp. 1223-1230 (May 2000).

Smith, E., et al., "Lethality-based selection of recombinant genes in mammalian cells: application to identifying tumor antigens," Nat Med, vol. 7, No. 8, pp. 967-972 (Aug. 2001).

Smith, G., et al., "Vaccinia virus immune evasion," Immunol Rev., vol. 159, pp. 137-154 (Oct. 1997).

Smith, B., et al., "Prognostic Significance of Vascular Endothelial Growth Factor Protein Levels in Oral and Oropharyngeal Squamous Cell Carcinoma," Clinical Oncol., vol. 18, pp. 2046-2052 (May 2000).

Solyanik, G., et al., "Different growth patterns of a cancer cell population as a function of its starting growth characteristics: analysis by mathematical modelling," Cell. Prolif., vol. 28, No. 5, pp. 263-278 (Mar. 1995).

Spehner, D., et al. "Enveloped virus is the major virus form produced during productive infection with the modified vaccinia virus Ankara strain," Virology, vol. 273, pp. 9-15 (May 5, 2000).

Spriggs, M., et al., "Vaccinia and Cowpox Viruses Encode a Novel Secreted Interleukin-1-Binding Protein," Cell, vol. 71, No. 1, pp. 145-152 (Oct. 2, 1992).

Sroller, V., et al., "Effect of IFN-gamma receptor gene deletion on vaccinia virus virulence," Arch. Virol., vol. 146, pp. 239-249 (Mar. 2001).

Stojdl, D., et al., "Exploiting Tumor-Specific Defects in the Interferon Pathway With a Previously Unknown Oncolytic Virus," Nat. Med., vol. 6, No. 7, pp. 821-825 (Jul. 2000).

Stojdl, D., et al., "VSV Strains with Defects in their Ability to Shutdown Innate Immunity are Potent Systemic Anti-Cancer Agents." Cancer Cell, vol. 4, No. 4, pp. 263-275 (Oct. 2003).

Stokke, T., et al., "Uncoupling of the order of the S and M phases: effects of staurosporine on human cell cycle kinases," Cell Prolif., vol. 30, No. 5, pp. 197-218 (Aug. 1997).

Symons, J., et al., "A study of the vaccinia virus interferon-gamma receptor and its contribution to virus virulence," J. Gen. Virol., vol. 83, No. 8, pp. 1953-1964 (Aug. 2002).

Symons, J., et al., "The vaccinia virus C12L protein inhibits mouse IL-18 and promotes virus virulence in the murine intranasal model," J. Gen. Virol., vol. 83, No. 11, pp. 2833-2844 (Nov. 2002).

Symons, J., et al., "Vaccinia virus encodes a soluble type I interferon receptor of novel structure and broad species specificity," Cell, vol. 81, pp. 551-560 (May 19, 1995).

"The 14th Annual Meeting 2008 Japan Society of Gene Therapy," The Journal of Gene Medicine, vol. 11, No. 12, pp. 11383-1193 (Nov. 25, 2009).

"The 14th Annual Meeting 2008 Japan Society of Gene Therapy Program and Abstracts," retrieved from the internet on Feb. 14, 2014—URL:http://jsgt.jp/annual-eeting/08JSGT/14-program2008.pdf.

Thorne, S., et al., "Future directions of the field oncolytic virotherapy: a perspective on the use of vaccinia virus," Expert Opinion Biol. Ther., vol. 4, pp. 1307-1321 (Aug. 2004).

Thorne, S., et al., "169. The Creation of Novel Oncolytic Vaccinia Virus Vectors for Efficient Systemic Delivery of Transgenes to Tumors," Mol. Ther., vol. 11, Supplement 1, p. S67 (May 2005).

Thorne, S., et al., "Rational Strain Selection and Engineering Creates a Broad Spectrum Systemically Effective Oncolytic Poxvirus JX-963," The Journal of Clinical Investigation, vol. 117, No. 11, pp. 3350-3358 (Nov. 2007).

Thorne, S., et al., "The Use of Oncolytic Vaccinia Viruses in the Treatment of Cancer: A New Role for an Old Ally?," Current Gene Therapy, vol. 5, pp. 429-443 (Aug. 2005).

Thorne, S., et al., "Oncolytic Virotherapy: Approaches to Tumor Targeting and Enhancing Antitumor Effects," Semin. Oncol., vol. 6, pp. 537-548 (Dec. 2005).

Timiryasova, T., et al., "Antitumor effect of vaccinia virus in glioma model," Oncol Res, vol. 11, pp. 133-144 (Apr. 30, 1999).

Todo, T., et al., "In situ expression of soluble B7-1 in the context of oncolytic herpes simplex virus induces potent antitumor immunity," Cancer Res, vol. 61, pp. 153-161 (Jan. 1, 2001).

Trevor, K., et al., "Transduction of human dendritic cells with a recombinant modified vaccinia Ankara virus encoding MUC1 and IL-2," Cancer Immunology Immunotherapy, vol. 50, No. 8, pp. 397-407 (Aug. 22, 2001).

Tscharke, D., et al., "Dermal Infection with Vaccinia Virus Reveals Roles for Virus Proteins not seen using other Inoculation Routes," J. Gen. Virol., vol. 83, pp. 1977-1986 (Aug. 2002).

Tsujimoto, Y., et al., "Analysis of the structure, transcripts, and protein products of bcl-2, the gene involved in human follicular lymphoma," Proc. Natl. Acad. Sci., vol. 83, No. 14, pp. 5214-5218 (Jul. 1986).

Tsujimoto, Y., et al., "Involvement of the bcl-2 gene in human follicular lymphoma," Science, vol. 228, No. 4706, pp. 1440-1443 (Jun. 1985).

Tsujimoto, Y., et al., "Clustering of breakpoints on chromosome 11 in human B-cell neoplasms with the t(11;14) chromosome translocation," Nature, vol. 314, pp. 340-343 (May 1985).

Tsumaki, N., et al., "Modular Arrangement of Cartilage- and Neural Tissue-specific cis-Elements in the Mouse a2(XI) Collagen Promoter," J. Biol. Chem., vol. 273, No. 36, pp. 22861-22864 (Sep. 1998).

Upton, C., et al., "Encoding of a Homolog of the IFN-γ Receptor by Myxoma Virus," Science, vol. 258, pp. 1369-1372 (Nov. 20, 1992).

Upton, C., et al., "Myxoma Virus Expresses a Secreted Protein with Homology to the Tumor Necrosis Factor Receptor Gene Family That Contributes to Viral Virulence," Virology, vol. 184, No. 1, pp. 370-382 (Sep. 1991).

(56) References Cited

OTHER PUBLICATIONS

Vanderplasschen A., "A Novel Virus Binding Assay Using Confocal Microscopy: Demonstration that the Intracellular and Extracellular Vaccinia Virions Bind to Different Cellular Receptors," J. Virol., vol. 71, No. 5, pp. 4032-4041 (May 1997).
Vanderplasschen A., "Intracellular and Extracellular Vaccinia Virions enter Cells by Different Mechanisms," J. Gen. Virol., vol. 79, Part 4, pp. 877-887 (Apr. 1998).
Vanderplasschen, A., et al., "Extracellular enveloped vaccinia virus is resistant to complement because of incorporation of host complement control proteins into its envelope," Proc Natl Acad Sci USA, vol. 95, No. 13, pp. 7544-7549 (Jun. 1998).
Verardi, P., et al., "Vaccinia virus vectors with a inactivated gamma interferon receptor homolog gen (B8R) are attenuated in vivo without a concomitant reduction in immunogenicity," J Virol, vol. 75, No. 1, pp. 11-18 (Jan. 2001).
Vicari, A., et al., "Chemokines in cancer," Cytokine Growth Factor Rev., vol. 13, pp. 143-154 (Apr. 2002).
Vogelstein B., et al., "P53 Function and Dysfunction," Cell, vol. 70, No. 4, pp. 523-526 (Aug. 1992).
Wallach, D., et al., "Tumor Necrosis Factor Receptor and Fas Signaling Mechanisms," Annu. Rev. Immunol., vol. 17, pp. 331-367 (Apr. 1999).
Walport, M., "Complement. First of two parts," N Engl J Med., vol. 344, No. 14, pp. 1058-1066 (Apr. 5, 2001).
Wang. H,. et al., "A Recombinant Adenovirus Ttype 35 Fiber Knob Protein Sensitizes Lymphoma Cells to Rituximab Therapy," Blood, vol. 115, No. 3, pp. 592-600 (Jan. 2010).
Weiner, L.M., et al., "Monoclonal Antibodies: Versatile Platforms for Cancer Immunotherapy," Nat Rev Immunol., vol. 10, No. 5, pp. 317-327 (May 2010).
Weijer, K., et al., "Feline Malignant Mammary Tumors. I. Morphology and Biology: Some Comparisons With Human and Canine Mammary Carcinomas," J Natl Cancer Inst, vol. 49, pp. 1697-1707 (Aug. 1972).
Wold, W., et al., "Adenovirus proteins that subvert host defenses," Trends Microbiol, vol. 2, No. 11, pp. 437-443, (Nov. 1994).
Wold, W., et al., "Mapping a New Gene That Encodes an 11,600-Molecular-Weight Protein in the E3 Transcription Unit of Adenovirus 2," J. Virol., vol. 52, No. 2, pp. 307-313 (Nov. 1984).
Wolffe, E., et al., "Deletion of the vaccinia virus B5R gene encoding a 42-kilodalton membrane glycoprotein inhibits extracellular virus envelope formation and dissemination," J. Virol., 67, pp. 4732-4741 (Aug. 1993).
Wong, T., et al., "Appearance of beta-lactamase activity in animal cells upon liposome-mediated gene transfer," Gene, vol. 10, pp. 87-94 (Jul. 1980).
Written Opinion of PCT/US2010/48829 dated Dec. 16, 2010.
Written Opinion of PCT/US06/034945 dated Mar. 23, 2007.
Written Opinion of PCT/12/20173 dated Apr. 13, 2012.
Wu, H., et al., "Promoter-Dependent Tissue-Specific Expressive Nature of Imprinting Gene, Insulin-like Growth Factor II, in Human Tissues," Biochem. Biophys. Res. Commun., vol. 233, No. 1, pp. 221-226 (Feb. 1997).
Xiang, et al., "Blockade of interferon induction and action by the E3L double-stranded RNA binding proteins of vaccinia virus," J Virol, vol. 76, No. 10, pp. 5251-5259 (May 2002).
Xu, X., et al., "Myxoma virus expresses a TNF receptor homolog with two distinct functions," Virus Genes, vol. 21, Nos. 1-2, pp. 97-109 (Aug. 2000).
Zeimet, A., et al., "Why did p53 Gene Therapy Fail in Ovarian Cancer?" Lancet Oncol., vol. 4, pp. 415-422 (Jul. 2003).
Zent, C., et al., Direct and Complement Dependent Cytotoxicity in CLL Cells From Patients with High-Risk Early-Intermediate Stage Chronic Llymphocytic Leukemia (CLL) Treated With Alemtuzumab and Rituximab., Leuk Res., vol. 32, No. 12, pp. 1849-1856, (Dec. 2008).
Zhao-Emonet, J., et al., "Deletional and mutational analyses of the human CD4 gene promoter: characterization of a minimal tissue-specific promoter," Biochem. Biophys. Acta., vol. 1442, No. 2-3, pp. 109-119 (Jul. 28, 1998).
U.S. Appl. No. 11/470,951—Restriction Requirement dated Apr. 26, 2007.
U.S. Appl. No. 11/470,951—Non-final office action dated Jul. 11, 2007.
U.S. Appl. No. 11/470,951—Final office action dated Apr. 1, 2008.
U.S. Appl. No. 11/470,951—Non-final office action dated Oct. 15, 2008.
U.S. Appl. No. 11/470,951—Final office action dated Jul. 6, 2009.
U.S. Appl. No. 11/470,951—Non-final office action dated Aug. 16, 2010.
U.S. Appl. No. 11/470,951—Final office action dated Apr. 19, 2011.
U.S. Appl. No. 11/470,951—Advisory Action dated Jun. 30, 2011.
U.S. Appl. No. 11/470,951—Final office action dated Dec. 6, 2013.
U.S. Appl. No. 11/470,951—Non-final office action dated Jan. 21, 2015.
U.S. Appl. No. 11/470,951—Final office action dated Apr. 27, 2015.
U.S. Appl. No. 13/535,291—Notice of Allowance dated Nov. 3, 2014.
U.S. Appl. No. 13/535,291—Final office action dated Apr. 23, 2014.
U.S. Appl. No. 13/535,291—Non-final office action dated Jan. 9, 2014.
U.S. Appl. No. 13/535,291—Non-final office action dated May 31, 2013.
U.S. Appl. No. 13/535,291—Final office action dated Sep. 13, 2013.
U.S. Appl. No. 11/838,774—Restriction Requirement dated May 19, 2009.
U.S. Appl. No. 11/838,774—Non-final office action dated Jul. 6, 2010.
U.S. Appl. No. 11/838,774—Restriction Requirement dated Nov. 19, 2009.
U.S. Appl. No. 12/531,353—Non-final office action dated Jan. 27, 2012.
U.S. Appl. No. 12/531,353—Final office action dated Jul. 9, 2012.
U.S. Appl. No. 13/395,929—Restriction Requirement dated Apr. 4, 2013.
U.S. Appl. No. 13/395,929—Non-final office action dated May 10, 2013.
U.S. Appl. No. 13/395,929—Final office action dated Sep. 3, 2013.
U.S. Appl. No. 13/395,929—Notice of Allowance dated Jan. 31, 2014.
U.S. Appl. No. 11/838,757—Restriction Requirement dated Apr. 27, 2009.
U.S. Appl. No. 11/838,757—Restriction Requirement dated Sep. 1, 2009.
U.S. Appl. No. 11/838,757—Non-final office action dated Dec. 29, 2009.
U.S. Appl. No. 11/838,757—Final office action dated Dec. 13, 2010.
U.S. Appl. No. 11/838,757—Non-final office action dated Jul. 26, 2011.
U.S. Appl. No. 11/838,757—Final office action dated Nov. 10, 2011.
U.S. Appl. No. 11/838,757—Advisory Action dated Apr. 25, 2012.
U.S. Appl. No. 11/838,757—Applicant Initiated Interview Summary dated Apr. 23, 2012.
U.S. Appl. No. 11/838,757—Non-final office action dated May 29, 2012.
U.S. Appl. No. 11/838,757—Notice of Allowability dated Oct. 4, 2012.
U.S. Appl. No. 10/524,932—Restriction Requirement dated Jan. 3, 2008.
U.S. Appl. No. 10/524,932—Non-final office action dated Apr. 15, 2008.
U.S. Appl. No. 10/524,932—Final office action dated Oct. 24, 2008.
U.S. Appl. No. 13/675,953—Notice of Allowance dated Nov. 13, 2014.
U.S. Appl. No. 13/675,953—Non-final office action dated Jul. 30, 2014.
U.S. Appl. No. 14/273,476—Final Office Action dated Nov. 21, 2014.
U.S. Appl. No. 14/273,476—Non-final office action dated Aug. 20, 2014.

\* cited by examiner

FIG. 4
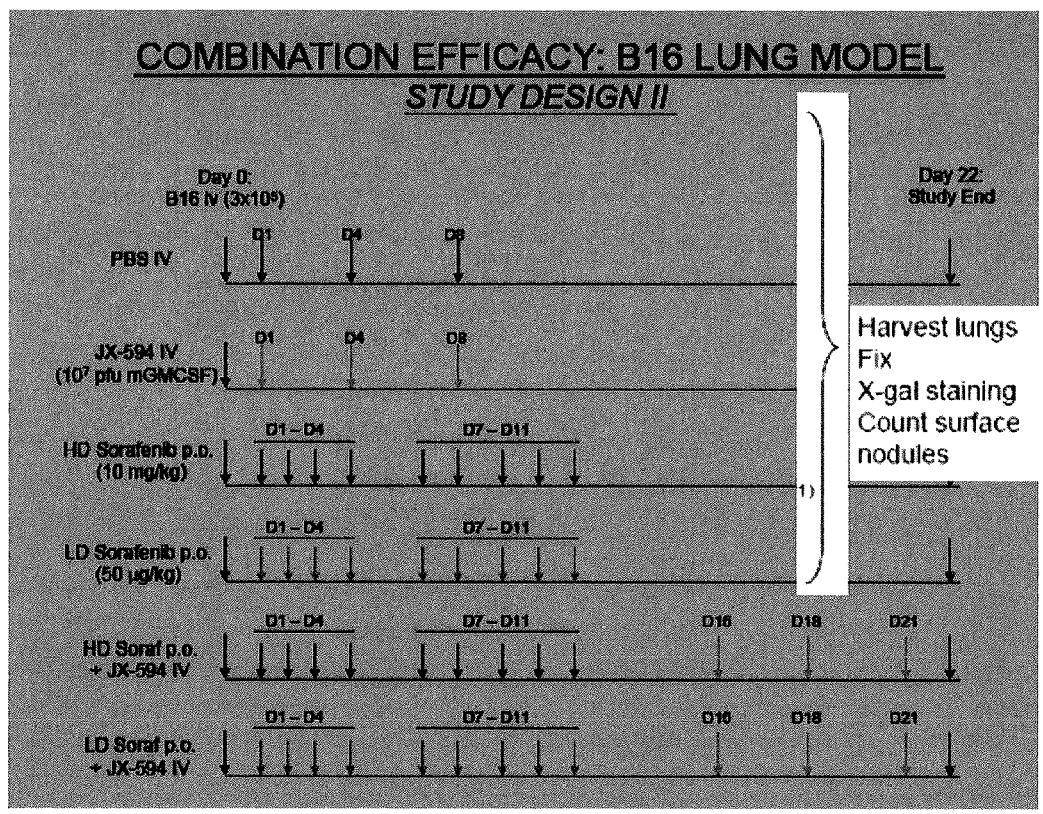
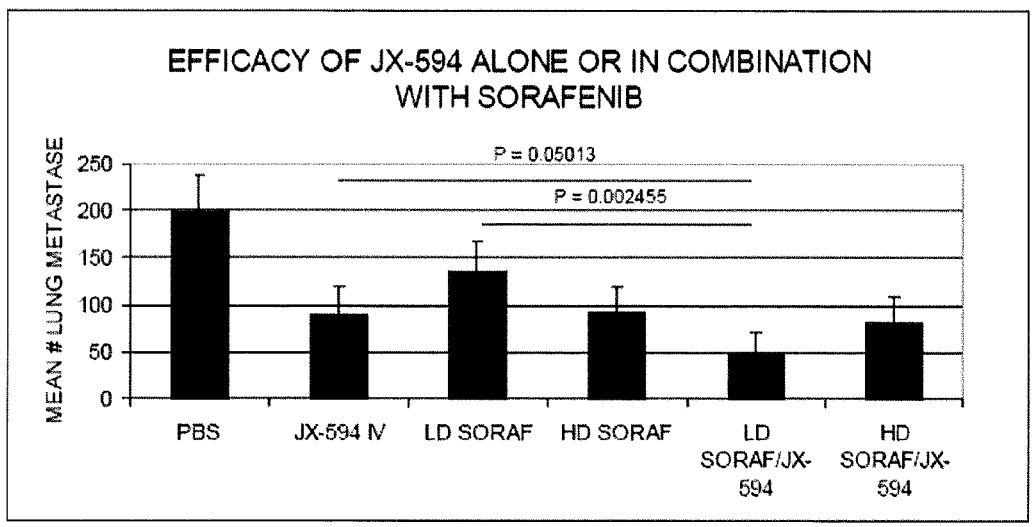

| Group | Drug and Dose | Treatment (Days) | Number |
|---|---|---|---|
| 1 | PBS | Daily | 8 |
| 2 | Sorafenib (400 µg) | Daily | 8 |
| 3 | JX-594 ($10^7$ pfu) | Days 1, 8, 15, 22, 29, 36 | 8 |
| 4 | JX-594 ($10^7$ pfu) with Sorafenib (40 µg) | JX-594: 1, 8, 15, 22, 29, 36 with Sorafenib: Daily | 8 |
| 5 | Sorafenib (400 µg) followed by JX-594 ($10^7$ pfu) | Sorafenib: Daily (1-14) followed by JX-594: 15, 22, 29, 36 | 8 |
| 6 | JX-594 ($10^7$ pfu) followed by Sorafenib (400 µg) | JX-594: Day 1, 8 followed by Sorafenib: Daily starting on Day 15 | 8 |

| Group | Date of sacrifice | Virus | Sorafenib | PBS |
|---|---|---|---|---|
| PBS control | Day 22 | - | - | + |
| JX-594 followed by sorafenib | Day 22 | + | + | - |
| JX 594 alone | Day 22 | + | - | - |
| Sorafenib alone | Day 22 | - | + | - |
| JX-594 followed by sorafenib | Day 35 | + | + | - |
| JX 594 alone | Day 35 | + | - | - |
| Sorafenib alone | Day 35 | - | + | - |
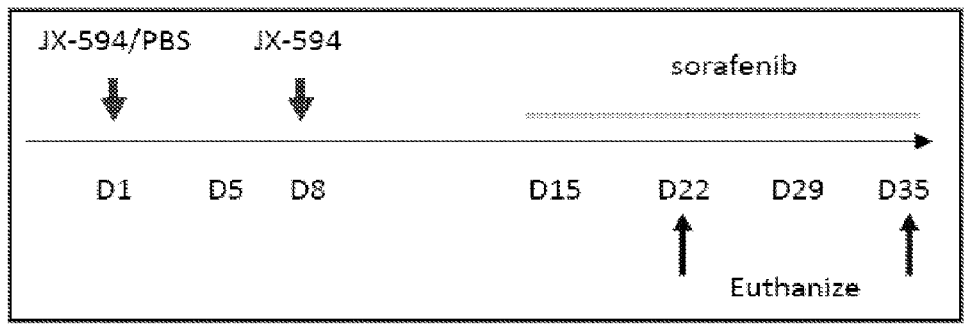
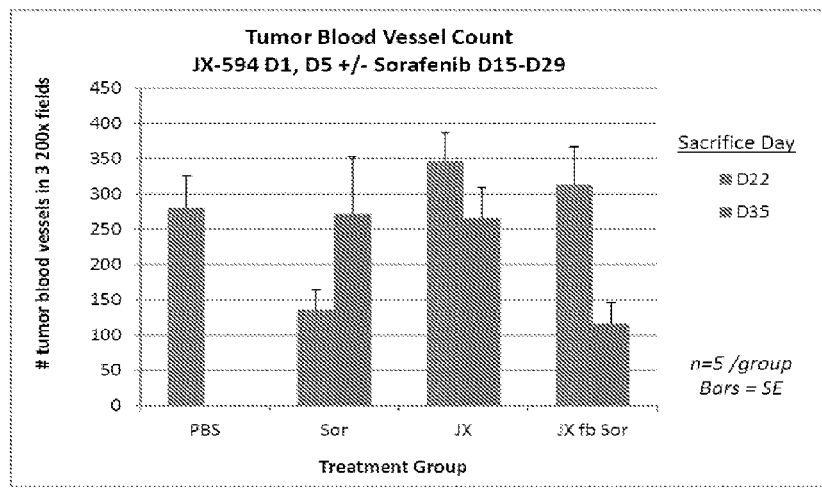
FIG. 6

FIGURE 10

Sorafenib Response in PNUH : MRI available patients were selected for evaluation of Choi response.

| ID | Name | Gender | Age | Dx date | Metastasis | PV invasion | TMN | Staging BCLC | Sorafenib Px | Dose | Image | RECIST | Choi | Tumor response |
|---|---|---|---|---|---|---|---|---|---|---|---|---|---|---|
| 30404427 JHC | | F | 51 | 09-2-13 | Bone | + | IV | C | 09-2-17 | 400 bid | MR | 2009-04-21 PD | No response | |
| 95026312 JCK | | M | 63 | 08-9-22 | Bone | - | IV | C | 09-2-24 | 200 bid | | Died | Died | |
| 80716327 JHS | | M | 48 | 08-12-12 | Bone | - | IV | C | 09-3-28 | 400 bid | MR | 2009-05-15 SD | No response | |
| 97040112 SBK | | M | 73 | 08-5-23 | No meta | + | IV | C | 09-3-31 | 400 bid | | Died | Died | |
| 50241107 JCL | | M | 57 | 05-5-6 | No meta | - | II | B | 08-7-2 | 400 bid | MR | 2008-10-22 SD | No response | |
| 50731002 YSP | | F | 43 | 06-1-13 | No meta | - | IIIA | B | 08-4-10 | 200 bid | MR | 2008-07-01 SD | No response | |
| 90116328 JJL | | M | 44 | 09-3-2 | No meta | + | IIIA | C | 09-3-27 | 400 bid | MR | no determined Died | NA | |
| 90104181 GOL | | F | 57 | 09-2-21 | LN, Lung | + | IV | C | 09-3-3 | 400 bid | | Died | Died | |
| 90101016 TGK | | M | 40 | 09-3-4 | No meta | + | IIIA | C | 09-3-17 | 400 bid | MR | 2008-10-08 SD | No response | |
| 90065518 TBO | | F | 62 | 09-2-11 | No meta | - | IIIA | C | 09-3-23 | 400 bid | | Died | Died | |
| 80587527 JHS | | M | 48 | 08-10-8 | No meta | + | IIIA | C | 08-10-15 | 200 bid | MR | 2009-01-22 PR | Response | |
| 80250728 DCK | | M | 37 | 08-4-28 | LN | + | IV | C | 08-5-8 | 400 bid | MR | 2009-01-16 SD | Response | |
| 70435663 IYK | | M | 54 | 06-12-10 | No meta | - | I | A | 08-2-11 | 200 bid | MR | 2009-05-04 SD | Response | |
| 60519719 SML | | M | 50 | 08-11-20 | No meta | - | IIIA | B | 09-3-24 | 00 bid | MR | 2009-05-29 SD | Response | |
| 60042590 JLJ | | M | 54 | 06-1-19 | No meta | - | II | B | 09-3-31 | 400 bid | | no determined | NA | |
| 50280964 DOK | | M | 63 | 05-5-25 | No meta | - | I | A | 08-5-15 | 200 bid | MR | 2008-06-17 SD | No response | |
| 10186956 SYC | | M | 55 | 06-7-5 | No meta | - | I | A | 08-10-30 | 200 bid | MR | 2009-02-24 PD | No response | |
| 20246145 JHY | | F | 49 | 07-7-27 | No meta | - | II | B | 08-12-17 | 400 bid | | Died | Died | |
| 50192971 GY | | M | 67 | 08-10-30 | No meta | + | IIIA | C | 08-11-5 | 400 bid | MR | 2009-02-12 PD | No response | |
| 50651182 EHJ | | F | 60 | 05-10-26 | No meta | - | II | B | 08-5-29 | 400 bid | MR | 2008-07-04 PD | No response | |
| 50687648 JHS | | M | 43 | 05-12-1 | No meta | - | I | A | 08-5-1 | 400 bid | MR | 2008-07-28 PD | No response | |
| 60168885 SJA | | F | 50 | 07-6-7 | No meta | - | II | B | 08-10-2 | 200 bid | MR | 2009-02-16 PD | No response | |
| 70295719 IHL | | M | 66 | 07-5-21 | LN | - | IIIA | C | 08-5-15 | 200 bid | MR | 2008-07-08 PD | No response | |
| 70723922 IMH | | M | 56 | 07-12-30 | No meta | - | IIIA | B | 08-3-25 | 200 bid | MR | 2008-10-28 PD | No response | |
| 70733381 GCY | | M | 56 | 07-12-28 | LN | - | IV | B | 08-6-10 | 200 bid | | Died | Died | |
| 80188308 BYK | | F | 69 | 08-3-28 | No meta | + | IIIA | C | 08-4-29 | 200 bid | MR | 2008-07-21 SD | No response | |
| 80223069 THK | | M | 67 | 5-4-2002 | No meta | - | II | B | 08-4-30 | 400 bid | MR | 2008-08-19 PD | No response | |
| 80305822 JHK | | M | 60 | 5-1-2007 | No meta | - | II | B | 08-10-30 | 400 bid | MR | Died | Died | |

Response? RTX together 7043, 1702 (JX594 3 cycles before sorafenib)
Response? RTX together 6051 1705 (JX594 3 cycles before sorafenib)

DCE-MRI images before and 5 days post-JX-594 treatment:
DCE-MRI images before and 4 weeks post-Sorafenib treatment:
FIG. 12

DCE-MRI images before and 4 weeks post-Sorafenib treatment:

Enhanced Necrosis evident in 3D reonstruction of tumors after JX-594 and sorafenib therapy :
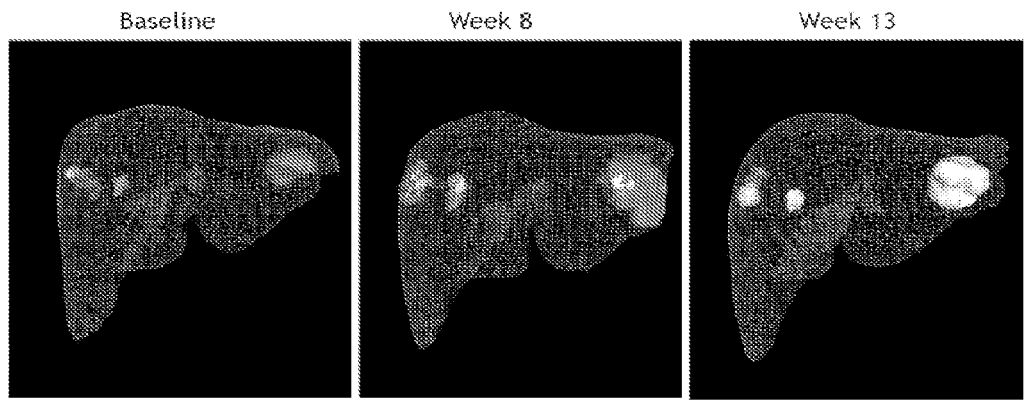
Quantitation of Necrosis of Tumors after JX-594 and Sorafenib Therapy :
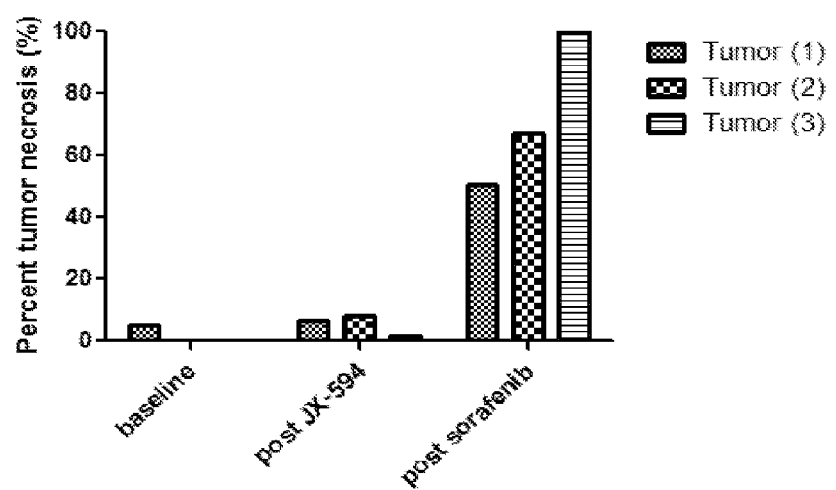
FIG. 16

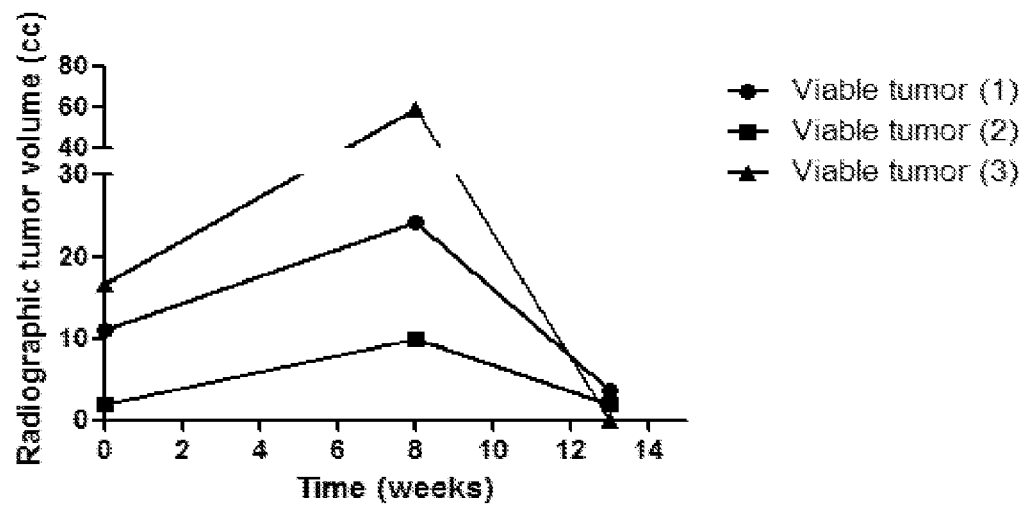
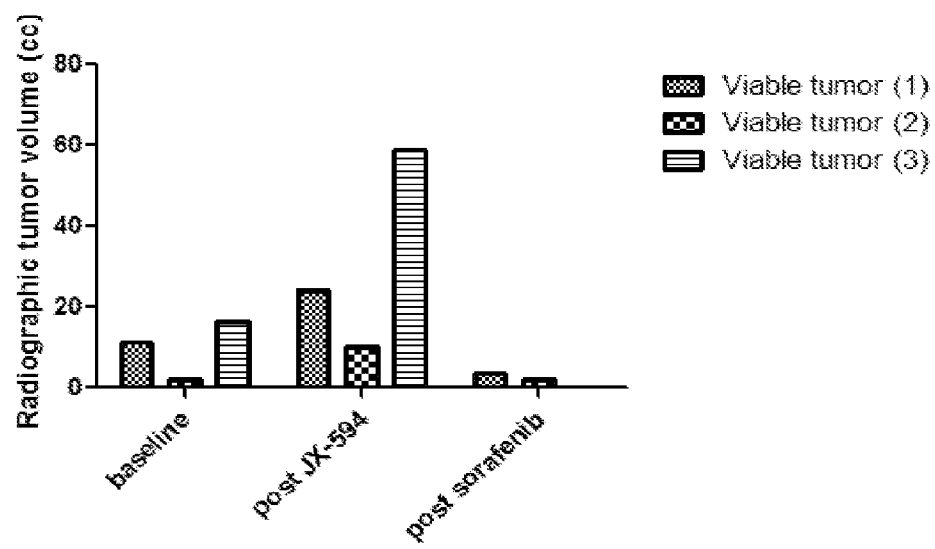
FIG. 17

ONCOLYTIC VACCINIA VIRUS COMBINATION CANCER THERAPY

BACKGROUND OF THE INVENTION

I. Field of the Invention

The present invention relates generally to the fields of oncology and virology. More particularly, it concerns poxviruses, specifically including oncolytic vaccinia viruses suitable for the treatment of cancer and their use in combination with anti-angiogenic agents.

II. Background

Normal tissue homeostasis is a highly regulated process of cell proliferation and cell death. An imbalance of either cell proliferation or cell death can develop into a cancerous state (Solyanik et al., 1995; Stokke et al., 1997; Mumby and Walter, 1991; Natoli et al., 1998; Magi-Galluzzi et al., 1998). For example, cervical, kidney, lung, pancreatic, colorectal, and brain cancer are just a few examples of the many cancers that can result (Erlandsson, 1998; Kolmel, 1998; Mangray and King, 1998; Mougin et al., 1998). In fact, the occurrence of cancer is so high that over 500,000 deaths per year are attributed to cancer in the United States alone.

Currently, there are few effective options for the treatment of many common cancer types. The course of treatment for a given individual depends on the diagnosis, the stage to which the disease has developed and factors such as age, sex, and general health of the patient. The most conventional options of cancer treatment are surgery, radiation therapy and chemotherapy. Surgery plays a central role in the diagnosis and treatment of cancer. Typically, a surgical approach is required for biopsy and to remove cancerous growth. However, if the cancer has metastasized and is widespread, surgery is unlikely to result in a cure and an alternate approach must be taken.

Replication-selective oncolytic viruses hold promise for the treatment of cancer (Kirn et al., 2001). These viruses can cause tumor cell death through direct replication-dependent and/or viral gene expression-dependent oncolytic effects (Kim et al., 2001). In addition, viruses are able to enhance the induction of cell-mediated antitumoral immunity within the host (Todo et al., 2001; Sinkovics et al., 2000). These viruses also can be engineered to expressed therapeutic transgenes within the tumor to enhance antitumoral efficacy (Hermiston, 2000). However, major limitations exist to this therapeutic approach as well.

Therefore, more additional therapies for the treatment of cancer are needed. The use of oncolytic viruses presents a potential area for development.

SUMMARY OF THE INVENTION

In vitro studies have indicated that sorafenib and similar kinase inhibitors suppress the effectiveness of poxvirus, vaccinia virus and particularly JX-594 when used in combination on cultured cell lines. Contrary to the in vitro findings, preclinical efficacy models have shown that combining sorafenib and JX-594 actually shows better efficacy than either agent alone. Thus, various aspects of the invention are directed to the application of these unexpected findings as in vivo therapy using a combination of poxvirus, vaccinia virus, or JX-594 virus and anti-angiogenic agents, such as kinase inhibitors, sorafenib, sutent, or similar compounds.

Embodiments of the invention are directed to methods for treating cancer in a subject previously administered a poxvirus therapy comprising administering an effective amount of an anti-angiogenic agent. In certain aspects it is determined that the tumor being treated is undergoing re-vascularization. In a further aspect the poxvirus is a vaccinia virus. In still a further aspect the vaccinia virus is a vaccinia virus expressing GM-CSF. Alternatively the vaccinia virus lacks a functional thymidine kinase gene. In certain aspects the vaccinia virus is JA-594.

Certain embodiments are directed to potentiating anti-angiogenic therapy, particularly those for which a patient has failed, has developed a tolerance, does not respond, or partially responds. As used herein, the term "potentiate", "potentiating", "therapy potentiating", "therapeutic effect is potentiated", and "potentiating the therapeutic effects" is defined herein as producing one or more of the following physiological effects: the increase or enhancement of the cytotoxic activity of therapeutic agents by acting in an additive or synergistic cytotoxic manner with the therapeutic agents; sensitizing cancer cells or a tumor to the anti-cancer activity of therapeutic agents; and/or restoring anti-angiogenic effectiveness of a therapy or sensitivity of a tumor to the therapy. Embodiments of the invention include anti-angiogenic agents as therapeutic agents for the treatment of cancer. In certain aspects methods of potentiating anti-angiogenic therapy include administering a poxvirus to a patient that is insensitive to, developed a tolerance for, or is not sufficiently responding to anti-angiogenic therapy in an amount that potentiates the therapeutic efficacy of the anti-angiogenic therapy. In further aspects the anti-angiogenic therapy is a kinase inhibitor, sorafenib, sutent, or similar compound. Methods of the invention can also include identifying a patient that is resistant or non-responsive or has cancer recurrence after anti-angiogenic therapy. In certain aspects a sensitizing amount of poxvirus, vaccinia virus, or JX-594 virus is administered to a patient that is resistant, tolerant, or insensitive to anti-angiogenic therapy (anti-angiogenic kinase inhibitors, sorafenib, sutent or similar compounds). A sensitizing amount is an amount sufficient render a tumor not showing a therapeutic response to a treatment—as determined by a physician or scientist—capable of responding to the same or similar therapy.

"Therapy resistant" cancers and tumors refers to cancers that have become resistant to anti-angiogenic cancer therapies. "Therapy sensitive" cancers are responsive (clinical parameters of response are detectable or measurable, such as tumor growth reduction, tumor necrosis, tumor shrinkage, tumor vascular shutdown and the like) to therapy. One of skill in the art will appreciate that some cancers are therapy sensitive to particular agents but not to others.

In certain aspects the anti-angiogenic agent is a kinase inhibitor. In other aspects the kinase inhibitor inhibits the Raf kinase pathway. In a particular aspect the kinase inhibitor is sorafenib, sutent, or similar anti-angiogenic kinase inhibitor.

Certain embodiments are directed to methods further comprising determining if a tumor is undergoing re-vascularization. In certain aspects re-vascularization is determined by non-invasive imaging of the tumor, for example, magnetic resonance imaging (MRI). In certain aspects the magnetic resonance imaging is dynamic contrast-enhanced MRI (DCE-MRI).

In certain aspects of the methods the anti-angiogenic agent is administered at least 2, 3, 4, 5, 6, 7, 8, 9, 10 or more weeks, including all values and ranges there between, after the first, second, third, fourth, fifth or more vaccinia virus administration.

In certain aspects the tumor is a brain tumor, a head & neck cancer tumor, an esophageal tumor, a skin tumor, a lung tumor, a thymic tumor, a stomach tumor, a colon tumor, a liver tumor, an ovarian tumor, a uterine tumor, a bladder tumor, a testicular tumor, a rectal tumor, a breast tumor, a kidney tumor, or a pancreatic tumor. In a further aspect the tumor is a hepatocellular carcinoma or a colorectal cancer.

In certain aspects the methods further comprising first administering to the subject the poxvirus, vaccinia virus, or JX-594 viral therapy. In a further aspect the viral therapy can be administered by injection into a tumor mass or by intravascular administration. In a particular aspect the virus is injection into tumor vasculature. In certain aspects the viral therapy can be administered via multiple modalities, e.g., intravascular and intratumoral, etc.

Certain embodiments are directed to methods for treating a hepatic tumor or metastatic tumor in the liver or other organ of a patient comprising administering sorafenib to the tumor, wherein the tumor was previous treated with a poxvirus, vaccinia virus, or JX-594 virus. Methods of the invention can also include determining if the tumor is undergoing reperfusion.

Certain aspects are directed to methods of treating a hepatic tumor, either primary or a metastatic tumor (a metastatic tumor being a tumor that originates in an organ or tissue distal from the location in which it is treated) comprising administering an effective amount of a poxvirus, a vaccinia virus, or a JX-594 virus, and administering an anti-angiogenic agent. In certain aspects the anti-angiogenic agent will be a kinase inhibitor. In further aspects the kinase inhibitor is sorafenib or sutent.

Certain embodiments are directed to methods of treating a hepatic tumor comprising administering an effective amount of a poxvirus, a vaccinia virus, or a JX-594 virus, wherein the tumor will be evaluated for reperfusion and determined to be a candidate for sorafenib therapy if the tumor is undergoing reperfusion.

In still further aspects are directed to methods of treating a patient having a tumor comprising (a) evaluating a tumor that has been treated with an anti-cancer therapy by non-invasive imaging of the tumor to detect reperfusion; and (b) administering an effective amount of anti-angiogenic agent, e.g., sorafenib or sutent, or similar kinase inhibitor, to a tumor in which reperfusion is detected or suspected. Imaging is not required for treating the a tumor with the combination of JX-594 and an anti-angiogenic such as sorafenib or sutent or similar kinase inhibitor.

JX-594 is a targeted oncolytic poxvirus designed to selectively replicate in and destroy cancer cells. Direct oncolysis plus granulocyte macrophage-colony stimulating factor (GM-CSF) expression also stimulates tumor vascular shutdown in tumors.

Certain embodiments of the invention are directed to methods that include administration of a thymidine kinase deficient vaccinia virus. In certain aspects, the methods include administering to the subject a TK-deficient, GM-CSF-expressing, replication-competent vaccinia virus vector (e.g., JX-594) in an amount sufficient to induce oncolysis of cells in the treated tumor or other tumors distal from the administration site. The administration of vaccinia virus can be followed by administration an anti-angiogenic agent, such as an anti-angiogenic tyrosine kinase inhibitor.

The tyrosine kinase inhibitor can be selected from the group consisting of sunitinib (SU1 1248; Sutent®), SU5416, SU6668, vatalanib (PTK787/ZK222584), AEE788, ZD6474, ZD4190, AZD2171, GW786034, sorafenib (BAY 43-9006), CP-547,632, AG013736, YM-359445, gefitinib (Iressa®), erlotinib (Tarceva®), EKB-569, HKI-272, and CI-1033. Sorafenib (Nexavar, Bayer), is a drug approved for the treatment of primary kidney cancer (advanced renal cell carcinoma) and advanced primary liver cancer (hepatocellular carcinoma).

Sorafenib is a small molecular inhibitor of several Tyrosine protein kinases. Sorafenib targets the Raf/Mek/Erk pathway (MAP Kinase pathway). Therefore, other kinase inhibitors that target this pathway are also contemplated as being useful in combination with JX-594.

In certain aspects, the subject is administered at least $1 \times 10^7$, $1 \times 10^8$, $2 \times 10^8$, $5 \times 10^8$, $1 \times 10^9$ $2 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$ or more viral particles or plaque forming units (pfu), including the various values and ranges there between. The viral dose can be administered in 0.1, 1, 2, 3, 4, 5, 6, 7, 8, 9, 10, 100, 500, 1000 or more milliliters, including all values and ranges there between. In one aspect, the dose is sufficient to generate a detectable level of GM-CSF in serum of the patient, e.g., at least about, at most about or about 2, 5, 10, 40, 50, 100, 200, 500, 1,000, 5,000, 10,000, 15,000 to 20,000 pg/mL, including all values and ranges there between. It is contemplated that a single dose of virus refers to the amount administered to a subject or a tumor over a 0.1, 0.5, 1, 2, 5, 10, 15, 20, or 24 hour period, including all values there between. The dose may be spread over time or by separate injection. Typically, multiple doses are administered to the same general target region, such as in the proximity of a tumor or in the case of intravenous administration a particular entry point in the blood stream or lymphatic system of a subject. In certain aspects, the viral dose is delivered by injection apparatus comprising a needle providing multiple ports in a single needle or multiple prongs coupled to a syringe, or a combination thereof. In a further aspect, the vaccinia virus vector is administered 2, 3, 4, 5, or more times. In still a further aspect, the vaccinia virus is administered over 1, 2, 3, 4, 5, 6, 7 or more days or weeks.

In certain embodiments the subject is a human. The subject may be afflicted with cancer and/or a tumor. In certain embodiments the tumor may be non-resectable prior to treatment and respectable following treatment. In certain aspects the tumor is located on or in the liver. In other aspects, the tumor can be a brain cancer tumor, a head and neck cancer tumor, an esophageal cancer tumor, a skin cancer tumor, a lung cancer tumor, a thymic cancer tumor, a stomach cancer tumor, a colon cancer tumor, a liver cancer tumor, an ovarian cancer tumor, a uterine cancer tumor, a bladder cancer tumor, a testicular cancer tumor, a rectal cancer tumor, a breast cancer tumor, or a pancreatic cancer tumor. In other embodiments the tumor is a bladder tumor. In still further embodiments the tumor is melanoma. The tumor can be a recurrent, primary, metastatic, and/or multi-drug resistant tumor. In certain embodiments, the tumor is a hepatocellular tumor or a metastasized tumor originating from another tissue or location. In certain aspects the tumor is in the liver.

In certain aspects the patient is monitored for tumor reperfusion. In certain aspects monitoring or evaluating the patient will be by non-invasive or minimally invasive imaging, e.g., magnetic resonance imaging. If reperfusion is detected or suspect a patient can be administered an anti-angiogenic agent, such as an anti-angiogenic tyrosine kinase inhibitor. In certain aspects, the tyrosine kinase inhibitor is sorafenib or similar agent. The anti-angiogenic agent can be administer at least, at most, or about 1, 2, 3, 4, 5, 6, 7, 8, 9, 10, 11, 12, 13, or more weeks after poxvirus virus therapy.

In certain aspects, the method further comprises administering to the subject an additional cancer therapy. The additional cancer therapy can be chemotherapy, biological therapy, radiotherapy, immunotherapy, hormone therapy, anti-vascular therapy, cryotherapy, toxin therapy and/or surgery, including combinations thereof. In still a further aspect, surgery includes the transarterial chemoembolization (TACE procedure, see Vogl et al., European Radiology 16(6):1393, 2005). The method may further comprise a second administration of the vaccinia virus vector. Methods of the invention can further comprise assessing tumor cell viability before, during, after treatment, or a combination thereof. In certain embodiments the virus is administered intravascularly, intratumorally, or a combination thereof. In a further aspect administration is by injection into a tumor mass. In still a further embodiment, administration is by injection into or in the region of tumor vasculature. In yet a further embodiment, administration is by injection into the lymphatic or vasculature system proximal to the tumor. In certain aspects the method includes imaging the tumor prior to or during administration. In certain aspects, a patient is or is not pre-immunized with a vaccinia virus vaccine. In a further aspect, the subject can be immunocompromised, either naturally or clinically.

In certain aspects, the virus is administered in an amount sufficient to induce cell or cancer cell death or necrosis in at least 15% of cells in an injected tumor, in at least 20% of cells in an injected tumor, in at least 30% of cells in an injected tumor, in at least 30% of cells in an injected tumor, in at least 40% of cells in an injected tumor, in at least 50% of cells in an injected tumor, in at least 60% of cells in an injected tumor, in at least 70% of cells in an injected tumor, in at least 80% of cells in an injected tumor, or in at least 90% of cells in an injected tumor.

In a further aspect of the invention, the methods can exclude pre-treatment of a subject with a vaccinia vaccine, e.g., a subject need not be vaccinated 1, 2, 3, 4, 5, or more days, weeks, months, or years before administering the therapy described herein. In some aspects, non-injected tumors or cancer will be infected with the therapeutic virus, thus treating a patient by both local administration and systemic dissemination.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4. Combination therapy with sorafenib enhances JX-594 efficacy in the murine B16 metastatic melanoma model. Top panel shows the study design of a combination efficacy preclinical study in B16 murine tumor model. Bottom panel shows average number of lung metastases that developed in each group.

FIG. 6 Anti-vascular effects of JX-594 followed by sorafenib. Top panels show study design of a preclinical study of JX-594 followed by Sorafenib in HepG2 xenograft model. Bottom panel shows average number of vessels in tumors (three 200× fields were counted). Error bars are standard error.

FIG. 10 Illustrates a summary of patient responses, including Choi assessment.

FIG. 12 Patient 1705—DCE-MRI images before and 5 days post-JX-594 treatment: DCE-MRI images before and 4 weeks post-Sorafenib treatment.

FIG. 16 Illustrates significant necrosis induction in patient treated with JX-594 followed by sorafenib (Patient 1705).

FIG. 17 Illustrates reduced viable tumor volume following sequential therapy with JX-594 and sorafenib.

DETAILED DESCRIPTION OF THE INVENTION

Figure 1:
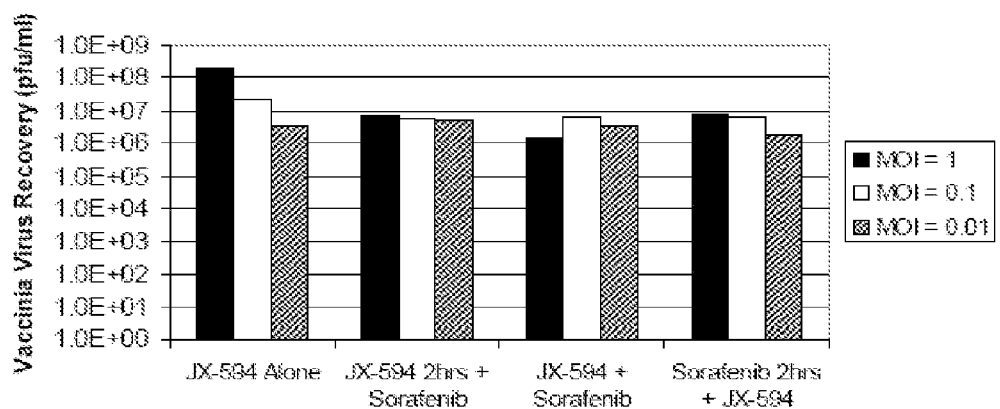
FIG. 1. JX-594 replication is inhibited in the presence of sorafenib in vitro. At various multiplicities of infection (MOI), JX-594 alone, or with 10 μM sorafenib, was added to PLC/PRF/5 cells. After 24 hours infection, cells and supernatants were collected for titration by plaque assay on Vero cells.

The present invention concerns the use of oncolytic poxviruses for the treatment of cancer. In particular, the use of a vaccinia virus expressing GM-CSF to achieve a particular degree of oncolysis is described. In another embodiment, a vaccinia virus can be used in a treatment regime that is more effective at treating vascularized or vascularizing tumors. A particular regime is the use of an anti-angiogenic agent after treatment with an oncolytic vaccinia virus. In certain aspects the treatment regime includes imaging the tumor to assess reperfusion that results from re-vacularization of the tumor after the vaccinia virus induce vascular collapse of the tumor. In certain aspects, the vaccinia virus is the JX-594 virus (TK minus, GM-CSF expressing vaccinia virus).

I. Treatment Regimens and Pharmaceutical Formulations

In an embodiment of the present invention, a method of treatment for a hyperproliferative disease, such as cancer, by the delivery of an oncolytic vaccinia virus, such as JX-594, is contemplated.

The methods include administrations of an effective amount of a pharmaceutical composition comprising an oncolytic vaccinia virus or an anti-angiogenic agent. A pharmaceutically effective amount is defined as that amount sufficient to induce oncolysis—the disruption or lysis of a cancer cell—and/or the inhibition of vascularization or destruction of neo-vasculature of tumors. The term includes the slowing, inhibition, or reduction in the growth or size of a tumor and includes the eradication of the tumor in certain instances. In certain aspects an effective amount of vaccinia virus results in systemic dissemination of the therapeutic virus to tumors, e.g., infection of non-injected tumors.

A. Combination Treatments

The compounds and methods of the present invention may be used in the context of hyperproliferative diseases/conditions, including cancer, and may be used in a particular order of administration with various time gaps between administration. In order to increase the effectiveness of a treatment with the compositions of the present invention, such as a GM-CSF-expressing vaccinia virus, it is desirable to combine these compositions with anti-angiogenic agents and other agents effective in the treatment of cancer. For example, the treatment of a cancer may be implemented with therapeutic compounds of the present invention in combination with anti-angiogenic agents.

Various combinations may be employed; for example, a poxvirus, such as vaccinia virus JX-594, is "A" and the secondary anti-angiogenic therapy is "B":

| |
|---|
| A/B/A B/A/B B/B/A A/A/B A/B/B B/A/A A/B/B/B B/A/B/B |
| B/B/B/A B/B/A/B A/A/B/B A/B/A/B A/B/B/A B/B/A/A |
| B/A/B/A B/A/A/B A/A/A/B B/A/A/A A/B/A/A A/A/B/A |

Administration of the poxvirus/vaccinia vectors of the present invention to a patient will follow general protocols for the administration of that particular therapy, taking into account the toxicity, if any, of the poxvirus treatment. After treatment with vaccinia virus an anti-angiogenic agent is administered to effectively treat neo-vascularization or reperfusion of the vaccinia virus treated tumor. It is expected that the treatment cycles would be repeated as necessary. It also is contemplated that various standard therapies, as well as surgical intervention, may be applied in combination with the described cancer or tumor cell therapy.

An "anti-angiogenic" agent is capable of negatively affecting angiogenesis in a tumor, for example, by killing cells, inducing apoptosis in cells, reducing the growth rate of cells involved in angiogenesis and effectively reducing the blood supply to a tumor or cancer cell. Examples of anti-angiogenic agents include, but are not limited to, sorafenib, sutent and similar compounds, retinoid acid and derivatives thereof, 2-methoxyestradiol, ANGIOSTATIN™, ENDOSTATIN™, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((I-azetidine-2-carboxylic acid (LACA), cishydroxyproline, d,I-3, 4-dehydroproline, thiaproline, alpha-dipyridyl, beta-aminopropionitrile fumarate, 4-propyl-5-(4-pyridinyl)-2(3 h)-oxazolone; methotrexate, mitoxantrone, heparin, interferons, 2 macroglobulin-serum, chimp-3, chymostatin, β-cyclodextrin tetradecasulfate, eponemycin; fumagillin, gold sodium thiomalate, d-penicillamine (CDPT), beta-1-anticollagenase-serum, alpha 2-antiplasmin, bisantrene, lobenzarit disodium, n-2-carboxyphenyl-4-chloroanthronilic acid disodium or "CCA", thalidomide; angiostatic steroid, carboxynaminolmidazole; metalloproteinase inhibitors such as BB94. Other anti-angiogenesis agents include antibodies, for example, monoclonal antibodies against these angiogenic growth factors: bFGF, aFGF, FGF-5, VEGF isoforms, VEGF-C, HGF/SF and Ang-1/Ang-2. Ferrara N. and Alitalo, K "Clinical application of angiogenic growth factors and their inhibitors" (1999) Nature Medicine 5:1359-1364. Other anti-angiogenesis agents may include inhibitors of VEGF transcription.

Angiogenesis, the formation of new blood vessels out of pre-existing capillaries, is a sequence of events that is of key importance in a broad array of physiologic and pathologic processes. A number of diseases are associated with formation of new vasculature. Angiogenesis is an important characteristic of various pathologies, including pathologies characterized or associated with an abnormal or uncontrolled proliferation of cells such as tumors. Pathologies which involve excessive angiogenesis include, for example, cancers (both solid and hematologic tumors). Cancer patient can benefit from inhibition of angiogenesis-tumor vascularization.

Angiogenesis is crucial to the growth of neoplastic tissues. For more than 100 years, tumors have been observed to be more vascular than normal tissues. Several experimental studies have suggested that both primary tumor growth and metastasis require neovascularization. Pathologic angiogenesis necessary for active tumor growth is generally sustained and persistent, with the initial acquisition of the angiogenic phenotype being a common mechanism for the development of a variety of solid and hematopoietic tumor types. Tumors that are unable to recruit and sustain a vascular network typically remain dormant as asymptomatic lesions in situ. Metastasis is also angiogenesis-dependent: for a tumor cell to metastasize successfully, it generally gains access to the vasculature in the primary tumor, survive the circulation, arrest in the microvasculature of the target organ, exit from this vasculature, grow in the target organ, and induce angiogenesis at the target site. Thus, angiogenesis appears to be necessary at the beginning as well as the completion of the metastatic cascade.

The criticality of angiogenesis to the growth and metastasis of neoplasms thus provides a target for therapeutic efforts. Appropriate anti-angiogenic agents may act directly or indirectly to influence tumor-associated angiogenesis either by delaying its onset or by blocking the sustainability of neovascularization of tumors.

Additional anti-cancer agents include biological agents (biotherapy), chemotherapy agents, and radiotherapy agents. More generally, these other compositions would be provided in a combined amount effective to kill or inhibit proliferation of the cell.

Typically, vaccinia virus therapy will precede other agents by intervals ranging from days to weeks. In embodiments where the other agent and poxvirus are applied separately to the cell, one would generally ensure that a significant period of time did not expire between the time of each delivery, such that the agent and poxvirus would still be able to exert an advantageously combined effect on the cell. In such instances, it is contemplated that one may contact the cell with both modalities within about 2-20 weeks of each other. In some situations, it may be desirable to extend the time period for treatment significantly where several days (2, 3, 4, 5, 6 or 7) to several weeks (1, 2, 3, 4, 5, 6, 7 or 8) lapse between the respective administrations.

In addition to treating a subject with vaccinia virus and an anti-angiogenic agent, an additional therapy can be used that includes traditional cancer therapies.

1. Chemotherapy

Cancer therapies include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as bio chemotherapy.

2. Radiotherapy

Other factors that cause DNA damage and have been used extensively include what are commonly known as .gamma.-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of certain poxvirus polypeptides would provide therapeutic benefit in the treatment of cancer.

4. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

Another form of therapy for use in conjunction with the current methods includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen.

B. Administration

In treating a tumor, the methods of the present invention administer an oncolytic vaccinia virus and then at a later time administer a composition comprising an anti-angiogenic agent. The routes of administration will vary, naturally, with the location and nature of the tumor, and include, e.g., intradermal, transdermal, parenteral, intravenous, intramuscular, intranasal, subcutaneous, regional (e.g., in the proximity of a tumor, particularly with the vasculature or adjacent vasculature of a tumor), percutaneous, intratracheal, intraperitoneal, intraarterial, intravesical, intratumoral, inhalation, perfusion, lavage, and oral administration. Compositions will be formulated relative to the particular administration route.

Intratumoral injection, or injection directly into the tumor vasculature is specifically contemplated. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The virus can be administered in multiple injections to the tumor, spaced at approximately 1 cm intervals. In the case of surgical intervention, the present invention may be used preoperatively, to render an inoperable tumor subject to resection. Continuous administration also may be applied where appropriate, for example, by implanting a catheter into a tumor or into tumor vasculature. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb or organ perfusion may be used to administer therapeutic compositions of the present invention, particularly in the treatment of hepatic tumors, melanomas, and sarcomas.

Treatment regimens may vary as well, and often depend on tumor type, tumor location, disease progression, and health and age of the patient. Certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one will deliver 1 to 100, 10 to 50, 100-1000, or up to about or at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp), including all values and ranges there between, to the tumor or tumor site.

C. Injectable Compositions and Formulations

The preferred method for the delivery of an expression construct or virus encoding all or part of a poxvirus genome to cancer or tumor cells in the present invention is via intratumoral injection. However, the pharmaceutical compositions disclosed herein may alternatively be administered parenterally, intravenously, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

II. Vaccinia Virus Jx-594

Poxviruses have been known for centuries, with the characteristic pock marks produced by variola virus (smallpox) giving this family its name. It appears that smallpox first emerged in China and the Far East over 2000 years ago. Fortunately, this often fatal virus has now been eradicated, with the last natural outbreak occurring in 1977 in Somalia.

The poxvirus viral particle is oval or brick-shaped, measuring some 200-400 nm long. The external surface is ridged in parallel rows, sometimes arranged helically. The particles are extremely complex, containing over 100 distinct proteins. The extracellular forms contain two membranes (EEV—extracellular enveloped virions), whereas intracellular particles only have an inner membrane (IMV—intracellular mature virions). The outer surface is composed of lipid and protein that surrounds the core, which is composed of a tightly compressed nucleoprotein. Antigenically, poxviruses are also very complex, inducing both specific and cross-reacting antibodies. There are at least ten enzymes present in the particle, mostly concerned with nucleic acid metabolism/genome replication.

The genome of the poxvirus is linear double-stranded DNA of 130-300 Kbp. The ends of the genome have a terminal hairpin loop with several tandem repeat sequences. Several poxvirus genomes have been sequenced, with most of the essential genes being located in the central part of the genome, while non-essential genes are located at the ends. There are about 250 genes in the poxvirus genome.

Replication takes place in the cytoplasm, as the virus is sufficiently complex to have acquired all the functions necessary for genome replication. There is some contribution by the cell, but the nature of this contribution is not clear. However, even though poxvirus gene expression and genome replication occur in enucleated cells, maturation is blocked, indicating some role by the cell.

The receptors for poxviruses are not generally known, but probably are multiple in number and on different cell types. For vaccinia, one of the likely receptors is EGF receptor (McFadden, 2005). Penetration may also involve more than one mechanism. Uncoating occurs in two stages: (a) removal of the outer membrane as the particle enters the cell and in the cytoplasm, and (b) the particle is further uncoated and the core passes into the cytoplasm.

Once into the cell cytoplasm, gene expression is carried out by viral enzymes associated with the core. Expression is divided into 2 phases: early genes: which represent about of 50% genome, and are expressed before genome replication, and late genes, which are expressed after genome replication. The temporal control of expression is provided by the late promoters, which are dependent on DNA replication for activity. Genome replication is believed to involve self-priming, leading to the formation of high molecular weight concatamer, which are subsequently cleaved and repaired to make virus genomes. Viral assembly occurs in the cytoskeleton and probably involves interactions with the cytoskeletal proteins (e.g., actin-binding proteins). Inclusions form in the cytoplasm that mature into virus particles. Cell to cell spread may provide an alternative mechanism for spread of infection. Overall, replication of this large, complex virus is rather quick, taking just 12 hours on average.

At least nine different poxviruses cause disease in humans, but variola virus and vaccinia are the best known. Variola strains are divided into variola major (25-30% fatalities) and variola minor (same symptoms but less than 1% death rate). Infection with both viruses occurs naturally by the respiratory route and is systemic, producing a variety of symptoms, but most notably with variola characteristic pustules and scarring of the skin.

A. Vaccinia Virus

Vaccinia virus is a large, complex enveloped virus having a linear double-stranded DNA genome of about 190K by and encoding for approximately 250 genes. Vaccinia is well-known for its role as a vaccine that eradicated smallpox. Post-eradication of smallpox, scientists have been exploring the use of vaccinia as a tool for delivering genes into biological tissues (gene therapy and genetic engineering). Vaccinia virus is unique among DNA viruses as it replicates only in the cytoplasm of the host cell. Therefore, the large genome is required to code for various enzymes and proteins needed for viral DNA replication. During replication, vaccinia produces several infectious forms which differ in their outer membranes: the intracellular mature virion (IMV), the intracellular enveloped virion (IEV), the cell-associated enveloped virion (CEV) and the extracellular enveloped virion (EEV). IMV is the most abundant infectious form and is thought to be responsible for spread between hosts. On the other hand, the CEV is believed to play a role in cell-to-cell spread and the EEV is thought to be important for long range dissemination within the host organism.

Vaccinia virus is closely related to the virus that causes cowpox. The precise origin of vaccinia is unknown, but the most common view is that vaccinia virus, cowpox virus, and variola virus (the causative agent for smallpox) were all derived from a common ancestral virus. There is also speculation that vaccinia virus was originally isolated from horses. A vaccinia virus infection is mild and typically asymptomatic in healthy individuals, but it may cause a mild rash and fever, with an extremely low rate of fatality. An immune response generated against a vaccinia virus infection protects that person against a lethal smallpox infection. For this reason, vaccinia virus was used as a live-virus vaccine against smallpox. The vaccinia virus vaccine is safe because it does not contain the smallpox virus, but occasionally certain complications and/or vaccine adverse effects may arise, especially if the vaccine is immunocompromised.

As discussed above, vaccinia viruses have been engineered to express a number of foreign proteins. One such protein is granulocyte-macrophage colony stimulating factor, or GM-CSF. GM-CSF is a protein secreted by macrophages that stimulates stem cells to produce granulocytes (neutrophils, eosinophils, and basophils) and macrophages. Human GM-CSF is glycosylated at amino acid residues 23 (leucine), 27 (asparagine), and 39 (glutamic acid) (see U.S. Pat. No. 5,073, 627, incorporated by reference). GM-CSF is also known as molgramostim or, when the protein is expressed in yeast cells, sargramostim (trademarked Leukine®), which is used as a medication to stimulate the production of white blood cells, especially granulocytes and macrophages, following chemotherapy. A vaccinia virus expressing GM-CSF has previously been reported. However, it was delivered not as an oncolytic agent, but merely as a delivery vector for GM-CSF. As such, it has been administered to patients at dosage below that which can achieve significant oncolysis. Herein is described the use of a GM-CSF expressing vaccinia virus that, in some embodiments, is administered at concentrations greater than $1 \times 10^8$ pfu or particles.

Vaccinia virus may be propagated using the methods described by Earl and Moss in Ausubel et al., 1994, which is incorporated by reference herein.

III. Nucleic Acid Compositions

In certain embodiments, the present invention concerns vaccinia virus and variants thereof.

A. Variants of Viral Polypeptides

Amino acid sequence variants of the polypeptides encoded by the vaccinia virus vectors of the invention can be substitutional, insertional or deletion variants. A mutation in a gene encoding a viral polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500 or more non-contiguous or contiguous amino acids of the polypeptide, as compared to wild-type. Various polypeptides encoded by Vaccinia virus may be identified by reference to Rosel et al., 1986, Goebel et al., 1990 and GenBank Accession Number NC001559, each of which is incorporated herein by reference.

Deletion variants lack one or more residues of the native or wild-type protein. Individual residues can be deleted or all or part of a domain (such as a catalytic or binding domain) can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of an immunoreactive epitope or simply one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

The term "functionally equivalent codon" is used herein to refer to codons that encode the same amino acid (see Table 1, below).

TABLE 1

Codon Table

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art byte and Kyte and Doolittle, 1982. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

B. Polynucleotides Encoding Native Proteins or Modified Proteins

The present invention concerns polynucleotides, isolatable from cells, that are capable of expressing all or part of a protein or polypeptide. In some embodiments of the invention, it concerns a viral genome that has been specifically mutated to generate a virus that lacks certain functional viral polypeptides. The polynucleotides may encode a peptide or polypeptide containing all or part of a viral amino acid sequence or they be engineered so they do not encode such a viral polypeptide or encode a viral polypeptide having at least one function or activity reduced, diminished, or absent. Recombinant proteins can be purified from expressing cells to yield active proteins. The genome, as well as the definition of the coding regions of Vaccinia Virus may be found in Rosel et al., 1986; Goebel et al., 1990; and/or GenBank Accession Number NC_001559, each of which is incorporated herein by reference.

As used herein, the term "DNA segment" refers to a DNA molecule that has been isolated free of total genomic DNA of a particular species. Therefore, a DNA segment encoding a polypeptide refers to a DNA segment that contains wild-type, polymorphic, or mutant polypeptide-coding sequences yet is isolated away from, or purified free from, total mammalian or human genomic DNA. Included within the term "DNA segment" are a polypeptide or polypeptides, DNA segments smaller than a polypeptide, and recombinant vectors, including, for example, plasmids, cosmids, phage, viruses, and the like.

As used in this application, the term "poxvirus polynucleotide" refers to a nucleic acid molecule encoding a poxvirus polypeptide that has been isolated free of total genomic nucleic acid. Similarly, a "vaccinia virus polynucleotide" refers to a nucleic acid molecule encoding a vaccinia virus polypeptide that has been isolated free of total genomic nucleic acid. A "poxvirus genome" or a "vaccinia virus genome" refers to a nucleic acid molecule that can be provided to a host cell to yield a viral particle, in the presence or absence of a helper virus. The genome may or may have not been recombinantly mutated as compared to wild-type virus.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a particular polypeptide from a given species may be represented by natural variants that have slightly different nucleic acid sequences but, nonetheless, encode the same protein (see Table 1 above).

Similarly, a polynucleotide comprising an isolated or purified wild-type or mutant polypeptide gene refers to a DNA segment including wild-type or mutant polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit (including any sequences required for proper transcription, post-translational modification, or localization). As will be understood by those in the art, this functional term includes genomic sequences, cDNA sequences, and smaller engineered gene segments that express, or may be adapted to express, proteins, polypeptides, domains, peptides, fusion proteins, and mutants.

A nucleic acid encoding all or part of a native or modified polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs.

The term "recombinant" may be used in conjunction with a polypeptide or the name of a specific polypeptide, and this generally refers to a polypeptide produced from a nucleic acid molecule that has been manipulated in vitro or that is the replicated product of such a molecule.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length polypeptide from any source or encode a truncated version of the polypeptide, for example a truncated vaccinia virus polypeptide, such that the transcript of the coding region represents the truncated version. The truncated transcript may then be translated into a truncated protein. A tag or other heterologous polypeptide may be added to the modified polypeptide-encoding sequence, wherein "heterologous" refers to a polypeptide that is not the same as the modified polypeptide.

In certain other embodiments, the invention concerns isolated DNA segments and recombinant vectors that include within their sequence a contiguous nucleic acid sequence from that shown in sequences identified herein (and/or incorporated by reference). Such sequences, however, may be mutated to yield a protein product whose activity is altered with respect to wild-type.

It also will be understood that this invention is not limited to the particular nucleic acid and amino acid sequences of these identified sequences. Recombinant vectors and isolated DNA segments may therefore variously include the poxvirus-coding regions themselves, coding regions bearing selected alterations or modifications in the basic coding region, or they may encode larger polypeptides that nevertheless include poxvirus-coding regions or may encode biologically functional equivalent proteins or peptides that have variant amino acids sequences.

The DNA segments of the present invention encompass biologically functional equivalent poxvirus proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

C. Mutagenesis of Poxvirus Polynucleotides

In various embodiments, the poxvirus polynucleotide may be altered or mutagenized. Alterations or mutations may include insertions, deletions, point mutations, inversions, and the like and may result in the modulation, activation and/or inactivation of certain pathways or molecular mechanisms or particular proteins (e.g., thymidine kinase), as well as altering the function, location, or expression of a gene product, in particular rendering a gene product non-functional. Where employed, mutagenesis of a polynucleotide encoding all or part of a Poxvirus may be accomplished by a variety of standard, mutagenic procedures (Sambrook et al., 1989).

Mutations may be induced following exposure to chemical or physical mutagens. Such mutation-inducing agents include ionizing radiation, ultraviolet light and a diverse array of chemical such as alkylating agents and polycyclic aromatic hydrocarbons all of which are capable of interacting either directly or indirectly (generally following some metabolic biotransformations) with nucleic acids. The DNA damage induced by such agents may lead to modifications of base sequence when the affected DNA is replicated or repaired and thus to a mutation. Mutation also can be site-directed through the use of particular targeting methods.

D. Vectors

To generate mutations in the poxvirus genome, native and modified polypeptides may be encoded by a nucleic acid molecule comprised in a vector. The term "vector" is used to refer to a carrier nucleic acid molecule into which an exogenous nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (1989) and Ausbel et al., 1994, both incorporated herein by reference. In addition to encoding a modified polypeptide such as modified gelonin, a vector may encode non-modified polypeptide sequences such as a tag or targeting molecule.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse a2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996), and the SM22α promoter.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading flames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (NCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex-virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

E. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors or viruses (which does not qualify as a vector if it expresses no exogenous polypeptides). A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae*, *Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

F. Methods of Gene Transfer

Suitable methods for nucleic acid delivery to effect expression of compositions of the present invention are believed to include virtually any method by which a nucleic acid (e.g., DNA, including viral and non-viral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994, 624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384, 253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

G. Lipid Components and Moieties

In certain embodiments, the present invention concerns compositions comprising one or more lipids associated with a nucleic acid, an amino acid molecule, such as a peptide, or another small molecule compound. In any of the embodiments discussed herein, the molecule may be either a poxvirus polypeptide or a poxvirus polypeptide modulator, for example a nucleic acid encoding all or part of either a poxvirus polypeptide, or alternatively, an amino acid molecule encoding all or part of poxvirus polypeptide modulator. A lipid is a substance that is characteristically insoluble in water and extractable with an organic solvent. Compounds than those specifically described herein are understood by one of skill in the art as lipids, and are encompassed by the compositions and methods of the present invention. A lipid component and a non-lipid may be attached to one another, either covalently or non-covalently.

A lipid may be naturally-occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or amino acid molecule, such as a peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid/poxvirus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-poxvirus or Superfect (Qiagen)-poxvirus complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 0.83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

IV. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Preclinical studies were performed in murine HCC models to assess mechanisms of JX-594-induced vascular shutdown and subsequent re-perfusion. The potential of sorafenib to block reperfusion was evaluated. In a Phase 2 clinical trial, patients with HCC were treated with JX-594 by intratumoral injection every two weeks for three cycles. Tumor size, blood flow and density were assessed by dynamic contrast-enhanced (dce)-MRI and DW-MRI at baseline, Day 5 and Week 8. Two patients with partial tumor re-perfusion at Week 8 initiated standard sorafenib therapy, and sequential DCE-MRI scans were performed.

Tumor vascular shutdown was demonstrated in a murine HCC model after IT or IV administration of JX-594. Vascular shutdown was dependent on viral replication; mGM-CSF expression from the virus and neutrophil infiltration enhanced the effect. Re-perfusion of the tumor rim was demonstrated over time and correlated to increased VEGF levels in the tumor. Adjuvant sorafenib therapy inhibited angiogenesis and led to significantly improved anti-tumoral efficacy over either agent alone. HCC patients treated with JX-594 demonstrated acute tumor vascular shutdown and necrosis in both injected and non-injected tumors within the liver. Adjuvant therapy with sorafenib after the Week 8 assessment led to dramatic and durable tumor necrosis and vascular shutdown in two patients. Reviews of serial MRI scans from HCC patients on sorafenib alone demonstrated that these findings were specific to patients pre-treated with JX-594.

Because tumors have a high mutation rate and therefore may have a high degree of heterogeneity leading to mixed responses to any one therapy, it can be useful to combine certain anti-cancer agents with alternative mechanisms of action. To determine if the combination of oncolytic virus therapy with sorafenib was safe and effective, in vitro and in vivo preclinical experiments were conducted.

Example 1

In Vitro Data—Sorafenib Inhibits JX-594

JX-594 was tested in combination with sorafenib on the human HCC cell line PLC/PRF/5. The PLC/PRF/5 human HCC cell line supports JX-594 replication. However, when Sorafenib (10 µM) was added either 2 hrs prior to; during; or 2 hrs after JX-594 infection, burst size was decreased up to 100 fold (FIG. 1). JX-594 was also tested in combination with sorafenib on human ovarian cancer cell line A2780 and human HCC line HepG2.

Cell Culture and Sorafenib Preparation: Human tumor cell lines A2780 (ovarian) and HepG2 (HCC) were obtained from American Type Culture Collection (ATCC). Cells were cultured in DMEM supplemented with 10% FBS and 1% pen/strep. Cells were grown at 37° C. in a humidified incubator containing 5% $CO_2$. For in vitro use, sorafenib was dissolved in DMSO (Sigma-Aldrich Corp.) to a concentration of 1 mg/ml and further diluted to appropriate final concentration (100 ng/ml, 250 ng/ml, 500 ng/ml, 1000 ng/ml and 2500 ng/ml) in DMEM with 10% fetal bovine serum. DMSO in the final solution did not exceed 0.2% (v/v).

Plaque Formation, Burst Assay and Cell Viability: A2780 or HepG2 cells were seeded into 6-well plates at $4 \times 10^5$ cells/well and left overnight. 100 pfu of JX-594 was then added to each well and allowed to infect for 2 hours. At the end of the infection, the media was removed and 3% Carboxymethyl-cellulose DMEM overlay containing sorafenib at final concentrations of 0, 0.1, 0.25, 0.5, 1.0, and 2.5 µg/mL was added. Three days later, plates were stained with crystal violet and plaques were counted. In parallel, to assess replication (burst size), 6-well plates were prepared as above. Instead of staining and counting plaques, cells were harvested from each well for purification of virus. Cells were lysed by 3 rounds of freezing and thawing followed by sonication, before serial dilutions of the crude viral lysate was added to A2780 cells to titer the virus by plaque assay. Furthermore, to assess the direct effects of sorafenib on cell viability, cells were plated in 96 well plates and incubated with sorafenib only. Cell viability was determined by means of colorimetric assay based on live-cell mediated reduction of tetrazolium salt to formazan chromagen (Cell Counting Kit-8, Donjindo Laboratories, Kumamoto, Japan).

Figure 2:
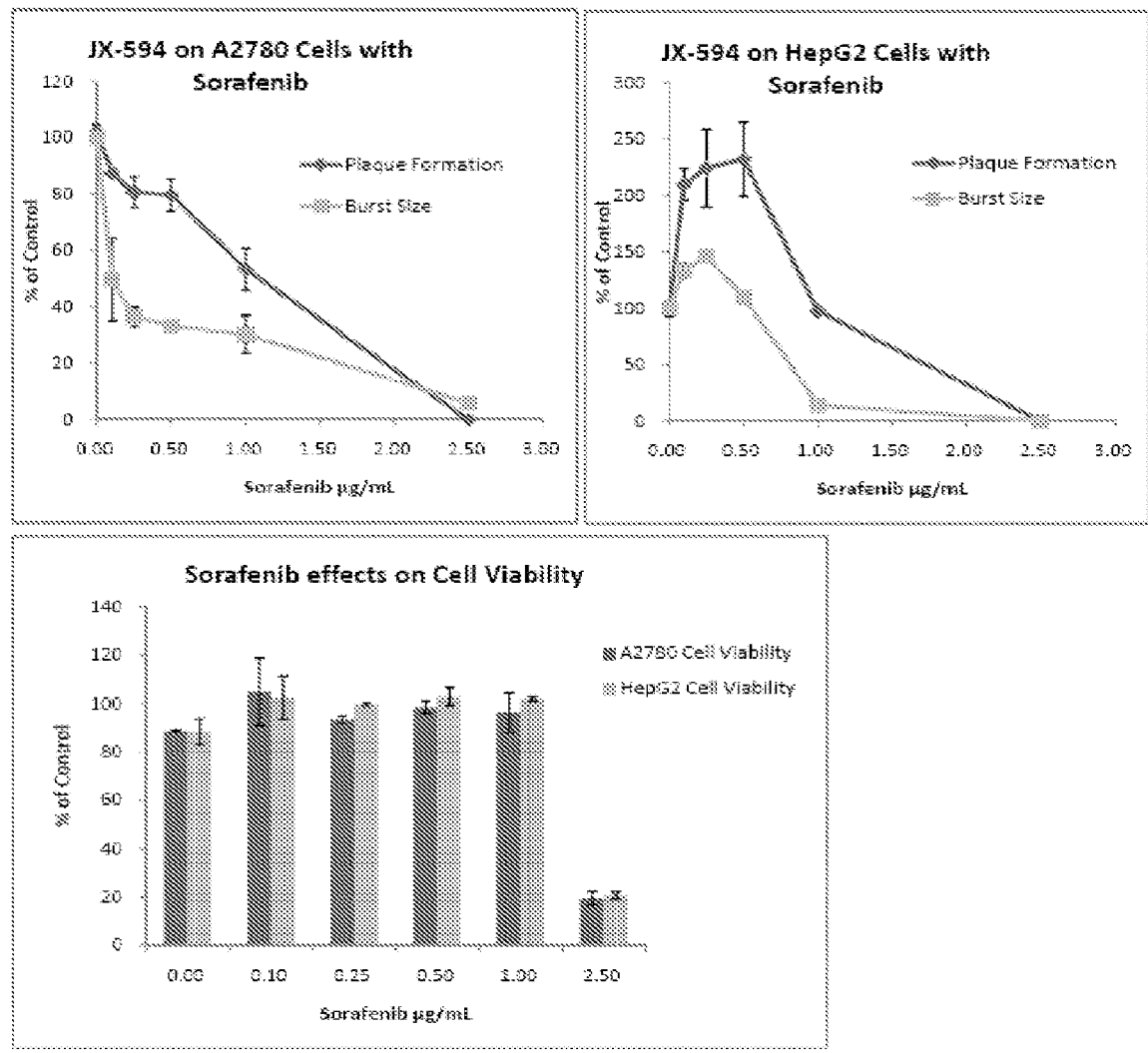
FIG. 2. Sorafenib Inhibits JX-594 Plaque Formation and Replication. JX-594 was allowed to infect monolayers of A2780 or HepG2 cells in the absence or presence of increasing concentrations of sorafenib. Top panels show experiments measuring plaque formation on the original monolayer, and the production of new viral particles (burst). Bottom panel shows that concentrations below cytotoxic levels are effective at inhibiting viral replication. The data are expressed as percent of control (no JX-594, no sorafenib). Error bars are standard deviation of replicates FIG. 3. Combination therapy with sorafenib enhances JX-594 efficacy against CT26 subcutaneous solid tumors. Top panel shows the study design of a combination efficacy preclinical study in mice with CT2 subcutaneous tumors. Kaplan-Meier survival curves are shown for each condition in the middle panel. Effects on tumor volume are shown in the lower panel.

Results: Concentrations of Sorafenib that are below cytotoxic levels can inhibit viral growth and replication on A2780 and HEPG2 tumor cell lines (FIG. 2). Additional experiments showed that sorafenib inhibited JX-594 replication in other human HCC lines including SNU423, SNU398, SNU475, SNU449, SNU387 and the human osteosarcoma line U2OS.

Sorafenib is a multikinase inhibitor and is capable of inhibiting the Ras signal transduction pathway (RAS/RAF/MEK/ERK) by inhibition of intracellular serine/threonine kinases Raf-1 and B-Raf. Activation of the Ras/Raf pathway commonly occurs in cancer and leads to transcriptional activation of E2F-responsive genes, including S-Phase genes such as thymidine kinase (TK) (Hengstschlager et al., 1994). JX-594 is vaccinia virus attenuated by inactivation of the viral TK gene. This mutation is designed to provide for selective replication in cells with high levels of cellular TK (i.e. cancer cells with abnormally activated pathways leading to constitutive E2F activation). While sorafenib and JX-594 are therefore both designed to targeted cancer cells with activated Ras pathway, simultaneous dosing of the therapies in vitro can lead to inhibition of viral replication which depends on an activated Ras pathway.

Example 2

In Vivo Data—Sorafenib Enhances JX-594

Contrary to the in vitro findings, preclinical efficacy models showed that combining sorafenib and JX-594 shows better efficacy than either agent alone.

Figure 3:
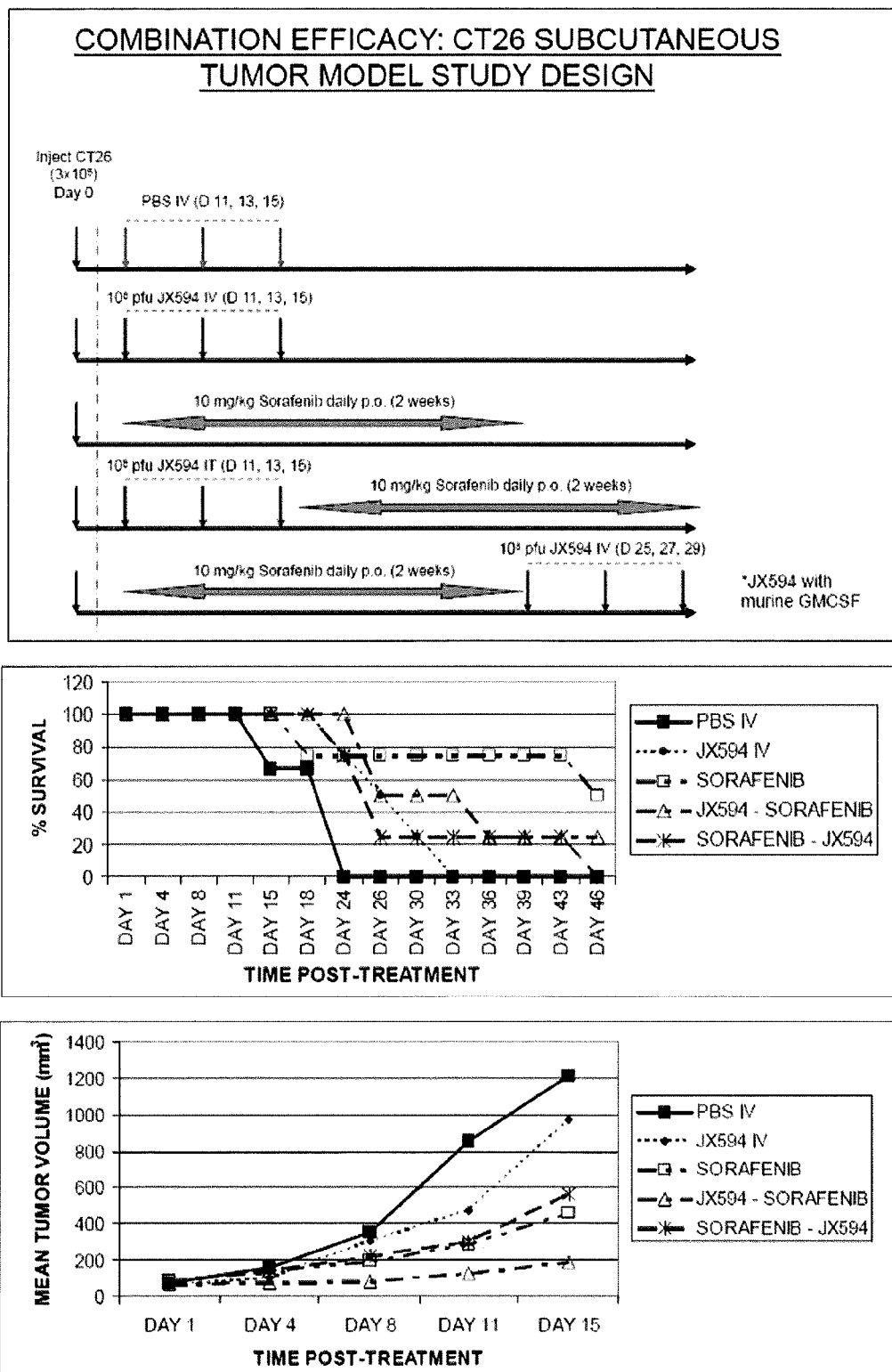

Sorafenib enhances JX-594 activity against murine CT26 primary tumors in vivo: The combination of JX-594 and sorafenib was tested in an immunocompetent murine model of subcutaneously implanted CT26 colorectal tumor cells. Balb/c mice were injected with $3\times10^5$ CT26 cells subcutaneously and after 11 days, treatment commenced with Sorafenib alone (10 mg/kg p.o. daily for 2 weeks), JX594 alone ($10^8$ pfu IV 3 times per week for 1 week), or in combination (JX594 prior to Sorafenib, or Sorafenib prior to JX594) (n=4 per group) (FIG. 3, upper panel). Control animals received PBS only. For this experiment, a version of JX-594 was used that expresses murine GM-CSF. Tumors were measured twice weekly until endpoint. Surviving proportions of each study group at each timepoint post treatment are shown (FIG. 3, middle panel). The mean tumor volumes of each study group at each timepoint post-treatment are shown (FIG. 3, lower panel). Compared to JX-594 alone, JX-594 in combination with Sorafenib enhanced survival and reduced tumor burden. JX-594 in combination with Sorafenib also reduced the tumor burden compared to Sorafenib-only animals. The preferred regimen was JX-594 followed by Sorafenib.

Sorafenib enhances JX-594 activity against murine B16 melanoma lung nodules in vivo: The combination of JX-594 and sorafenib was tested in an immunocompetent murine model of B16 melanoma tumors. C57BL/6 mice were injected with $3\times10^5$ B16-F10-LacZ cells IV and treated with Sorafenib alone (HD: 10 mg/kg, LD: 50 µg/kg p.o. daily for 2 weeks), JX594 alone ($10^7$ pfu IV 3 times per week for 1 week), or in combination (LD or HD sorafenib prior to JX-594 IV) (n=5 per group)(FIG. 4, top panel). At the end of treatment, mice were sacrificed and lungs were fixed and stained to detect B16 surface nodules (n=5 per group). The mean number of tumor nodules at the end of study is shown for each group (FIG. 4). In the 50 µg/kg p.o. Sorafenib+JX-594 group, there was significant reduction in B16 tumors compared to the JX-594 alone group or the Sorafenib alone group.

Sorafenib enhances JX-594 activity against human HCC xenograft model in vivo: SCID mice were implanted with subcutaneous HepG2 human hepatocellular carcinoma xenograft tumors. Once tumors reached a size of approximately 12-14 mm maximal diameter mice were randomized into one of six treatment groups (n=8 per group) (1) PBS alone, (2) sorafenib alone (standard daily intraperitoneal dosing with 400 µg), (3) JX-594 alone (intravenous treatment of $10^7$ pfu weekly for six total doses), (4) simultaneous treatment with JX-594 and sorafenib, (5) sorafenib followed by JX-594 and (6) JX-594 (2 doses) followed by sorafenib.

Figure 5:
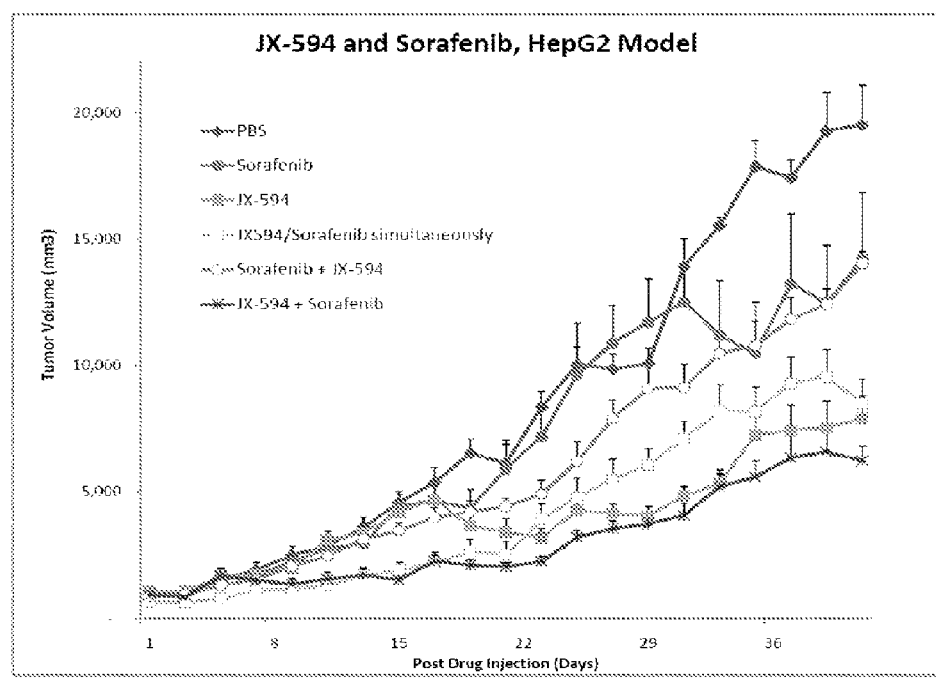
FIG. 5 JX-594 followed by Sorafenib shows superior efficacy in HCC xenograft model. Chart describes treatment schedule for each group. Graph plots average tumor size (mm3) for each group over time (bars are standard error of the mean).

Tumor size was measured using calipers and mice euthanized when tumor burdens reached allowable limit for ethical purposes. The regimen of JX-594 followed by sorafenib was superior to control or either agent alone in terms of tumor growth and time-to-tumor progression. In addition, this sequence was superior to sorafenib followed by JX-594 and to simultaneous treatment (FIG. 5).

A. Preclinical HCC Tumor Model Studies of Vascular Shutdown

Experimental Methods, Pilot Experiment: The pilot experiment was designed to show that JX-594 followed by Sorafenib induces acute vascular shutdown in the HepG2 model. Three groups were used (n=5 animals each). Group 1 received PBS only; Group 2 received a single dose of $10^6$ pfu JX-594 administered intravenously (IV); and Group 3 received a single dose of $10^6$ pfu JX-594 administered intratumorally (IT). Serum samples were collected on D5 for measurement of VEGF and GM-CSF levels. Prior to euthanization, mice were injected with fluorescent microspheres to allow for visualization of tumor perfusion. The resected tumor was divided into three portions for analysis 1) Flash frozen sample for measurement of VEGF protein levels 2) OCT-embedded sample preparation of frozen tumor sections to visualize microspheres and vascular marker CD31 and 3) Formalin fixed/paraffin-embedded sample for histological analysis.

Experimental Methods, Vascularity Study: The study followed longer term effects on vascularity and assessed the efficacy of JX-594+/–Sorafenib in the HepG2 model. HepG2 (human HCC line) tumors were implanted subcutaneously in nude mice. Animals were randomized to seven treatment groups (n=5 per group) to test agents alone, and in combination. Groups were treated with JX-594 ($10^6$ pfu. intratumorally, D1 and D8) and/or Sorafenib (400 µg i.p., daily D15-D29) or PBS (control) on the schedule detailed in (FIG. 6). Tumors were measured using calipers twice weekly. Serum samples were collected on D1, D8, D15, D22 and D29 for measurement of VEGF and GM-CSF levels. Mice were euthanized on D22 or D35. Prior to euthanization, mice were injected with fluorescent microspheres to allow for visualization of tumor perfusion. The resected tumor was divided into three portions for analysis 1) Flash frozen sample for measurement of VEGF protein levels 2) OCT-embedded sample preparation of frozen tumor sections to visualize microspheres and vascular marker CD31 and 3) Formalin fixed/paraffin-embedded sample for histological analysis.

Results: Vessels were counted in CD31-stained OCT tumor sections; the average number of vessels in 3 fields of 200× magnification are presented in (FIG. 6). Sorafenib alone caused a transient decrease in the number of vessels (Day 29), but vessel counts increase again over time (Day 35). However, in animals that received JX-594 followed by sorafenib, the number of vessel on D35 were lower compared to the sorafenib only group, suggesting the combination has a more lasting effect on tumor vasculature.

B. Clinical Data

JX-594 is a first-in-class targeted oncolytic poxvirus designed to selectively replicate in and destroy cancer cells. Direct oncolysis plus granulocyte macrophage-colony stimulating factor (GM-CSF) expression also stimulates tumor vascular shutdown in animal tumor models. Tumor vascular shutdown was assessed following JX-594 therapy in patients with hepatocellular carcinoma. In addition, feasibility of adjuvant anti-angiogenic therapy with sorafenib to prevent re-perfusion following JX-594 in both preclinical and clinical studies of hepatocellular carcinoma (HCC) were studied.

Methods: Preclinical studies were performed in murine HCC models to assess mechanisms of JX-594-induced vascular shutdown and subsequent re-perfusion. The potential of sorafenib to block reperfusion was evaluated. In a Phase 2 clinical trial, patients with HCC were treated with JX-594 by intratumoral injection every two weeks for three cycles. Tumor size, blood flow and density were assessed by dynamic contrast-enhanced (DCE)-MRI and DW-MRI at baseline, Day 5 and Week 8. Five patients with partial tumor re-perfusion at Week 8 initiated standard sorafenib therapy, and sequential dce-MRI scans were performed.

Findings: Tumor vascular shutdown occurs in murine HCC model after IT or IV administration of JX-594. Vascular shutdown was dependent on viral replication; mGM-CSF expression from the virus and neutrophil infiltration enhanced the effect. Re-perfusion of the tumor rim is demonstrated over time and correlated with increased VEGF levels in the tumor. Adjuvant sorafenib therapy inhibited angiogenesis and led to significantly improved anti-tumoral efficacy over either agent alone. HCC patients treated with JX-594 demonstrated acute tumor vascular shutdown and necrosis in both injected and non-injected tumors within the liver. Adjuvant therapy with sorafenib after the Week 8 assessment led to dramatic and durable tumor necrosis and vascular shutdown in at least three patients. Reviews of serial MRI scans from 15 HCC patients on sorafenib alone demonstrated that these findings were enhanced and enriched in patients pre-treated with JX-594.

JX-594 causes acute vascular shutdown and necrosis in HCC tumors, and sensitizes HCC to subsequent therapy with sorafenib. Randomized controlled trials of JX-594 followed by sorafenib versus sorafenib alone are indicated. Sequential therapy regimens with oncolytic poxviruses followed by anti-angiogenic agents hold promise.

Introduction: The targeted oncolytic poxvirus JX-594 replicates selectively in cancer cells, resulting in virus progeny production, tumor cell necrosis, release and spread within tumor tissues. JX-594 is also engineered to express the GM-CSF transgene in order to enhance the anti-tumoral immunity that results from oncolysis. The vaccinia backbone is inherently tumor-selective due to EGFR-ras pathway dependency and tumor-resistance to interferons. The inherent therapeutic index is amplified by the TK deletion; JX-594 replication is dependent on cellular TK, which is driven to high levels by cell cycle abnormalities in cancer. Results from a Phase 1 clinical trial of JX-594 in patients with refractory liver tumors demonstrated safety, efficacy and mechanistic proof-of-concept for JX-594 replication, systemic dissemination and biologically-active GM-CSF expression. Recently published preclinical studies demonstrated that oncolytic virus therapy can also induce acute tumor vascular shutdown (Breitbach, et al. 2007).

The inventors contemplate that the oncolytic poxvirus JX-594 causes tumor vascular shutdown, and that the GM-CSF expression from the virus enhances neutrophil recruitment and activation leading to augmentation of anti-vascular effects. Following preclinical studies, the inventors assess tumor vascular shutdown in patients with HCC, a tumor type that is hypervascular. Preclinical and clinical studies demonstrated the possibility of subsequent progression of a vascularized tumor rim.

Sorafenib is an oral multikinase inhibitor approved for treatment of renal cell carcinoma (RCC) and hepatocellular carcinoma (HCC). Sorafenib inhibits surface tyrosine kinase receptors (VEGF-R, PDGF-R) and intracellular serine/threonine kinases (Raf-1, B-Raf) and therefore is a multimechanistic anti-cancer agent. Sorafenib may affect tumor cells directly by inhibiting the Ras signaling pathway (RAS/RAF/MEK/ERK) which is commonly activated in cancer cells and promotes cell proliferation. Sorafenib may also reduce tumor growth through its anti-angiogenic effects resulting from inhibition of VEGF-R. Sutent (sunitinib/SU11248) is another targeted cancer therapy that inhibits the actions of vascular endothelial growth factor (VEGF) and has anti-angiogenic effects. It is approved for treatment of renal cell carcinoma and gastrointestinal stromal tumor (GIST).

The inventors contemplate that post-JX-594 re-perfusion is blocked by the anti-angiogenic agent sorafenib which is approved for use in HCC patients, or sutent which is approved for use in RCC patients. We tested this hypothesis in preclinical models of HCC, and in five patients after completion of therapy with JX-594.

C. Materials and Methods

Study Approvals and Registration: Study protocol and informed consent forms were approved by the US FDA, Korean FDA, and Institutional Review and Infection Control Committees at Pusan National University Hospital, Busan, South Korea. The protocol was registered via the world wide web at clinicaltrials.gov.

Patient Selection: Patients signed informed consent, according to Good Clinical Practice (GCP) guidelines. Inclusion criteria included unresectable, injectable hepatocellular tumor(s) within the liver (primary HCC) that had progressed despite treatment with standard therapies (treatment-refractory), normal hematopoietic function (leukocyte count>3, $\times 10^9$ cells/L, hemoglobin>100 g/L, platelet count>60$\times 10^9$ cells/L) and organ function (including creatinine≤132.6 µmol/L, aspartate aminotransferase (AST)/alanine aminotransferase (ALT)≤2·5 of upper normal limit, Child-Pugh class A or B), life expectancy≥16 weeks, and Karnofsky Performance Status (KPS)≥70. Exclusion criteria included extrahepatic tumors, tumors>10 cm max diameter, increased risk for vaccination complications (e.g. immunosuppression, eczema), treatment with immunosuppressive or cancer treatment agents within 4 weeks, rapidly progressive ascites, pregnancy or nursing.

Manufacturing and Preparation of JX-594: JX-594 is a Wyeth strain vaccinia modified by insertion of the human CSF2 and LacZ genes into the TK gene region under control of the synthetic early-late promoter and p7·5 promoter, respectively. Clinical trial material (CTM) was generated according to Good Manufacturing Practice (GMP) guidelines in Vero cells and purified through sucrose gradient centrifugation. The genome-to-pfu ratio was approximately 70:1. JX-594 was formulated in phosphate-buffered saline with 10% glycerol, 138 mM sodium chloride at pH 7-4. Final product quality control release tests included assays for sterility, endotoxin and potency. CTM was also tested for GM-CSF protein concentration and was negative (lower limit of detection<14,000 pg/mL). JX-594 was diluted in 0.9% normal saline in a volume equivalent to 25% of the estimated total volume of target tumor(s).

JX-594 Treatment Procedure, All IT Patients except 11301 (Sutent Patient): Patients with unresectable HCC were randomized to receive one of two dose levels ($10^8$ or $10^9$ pfu). JX-594 was administered via imaging-guided intratumoral injection using a multi-pronged Quadrafuse injection needle in roughly spherical tumors, and by a 21-gauge PEIT (percutaneous ethanol injection, multi-pore; HAKKO Medicals; Tokyo, Japan) needle in irregularly-shaped tumors. Tumors (n=1-5) were injected every two weeks for three cycles. The same tumors injected on cycle 1 were injected thereafter on each cycle.

Sorafenib Therapy and Tumor Response Assessment Following JX-594: Patients completed the IT clinical trial of JX-594 after 8 weeks on study. Some patients (Patients 1702, 1705, 1002, 1712, 1713) went on to receive standard sorafenib treatment (400 mg twice daily p.o.). Tumors in these patients were followed by DCE-MRI imaging using the same procedures that were used to assess response to JX-594 treatment.

JX-594 Treatment Procedure, Patients treated by IV JX-594 followed by IT JX-594 followed by Sorafenib: Patients with unrespectable HCC received two doses of JX-594 levels ($10^9$ pfu). For the first dose (Day 1), JX-594 was administered by intravenous infusion over 60 minutes. For the second and third doses (Day 8 and Day 22), JX-594 was administered via imaging-guided intratumoral injection using a multi-pronged Quadrafuse injection needle in roughly spherical tumors, or by a 21-gauge PEIT (percutaneous ethanol injection, multi-pore; HAKKO Medicals; Tokyo, Japan) needle in irregularly-shaped tumors. Starting on Day 25, patients imitated oral sorafenib therapy (400 mg twice daily p.o.). Patients with viable tumor tissue received a Week 12 IT injection of JX-594 (sorafenib treatment was temporarily discontinued 2-3 days before, during and 4-5 days after this booster injection). Imaging (CT, DECE MIR and/or PET-CT) was performed at baseline, Day 25, Week 6 and/or Week 12 to assess response.

JX-594 Treatment, Patient 11301 (Sutent Patient): Patient 11301 had renal cell carcinoma that had metastasized to the liver. Liver tumors were treated by intratumoral injection using a 21-gauge PEIT needle. The patient received a total of 4 doses of JX-594 ($10^9$ pfu/dose) given three weeks apart (=4 cycles). After every two cycles of treatment, contrast-enhanced CT scanning was performed and week 6 response assessment was performed using RECIST and Choi criteria. Patient experienced stable disease (SD) by RECIST critera and a Choi response (42% decrease in HU) (Park et al., 2008).

Sutent Treatment: Subsequently, Patient 11301 progressed and went on to receive sutent treatment. Patient received 3 courses of 50 mg/daily (4 weeks on, 2 weeks off) then 3 courses of 37.5 mg/daily (4 weeks on, 2 weeks off), and was maintained on a schedule of 25 mg/daily (2 weeks on, 1-2 weeks off).

Tumor vascularity and response assessment: DCE MRI (dynamic contrast-enhanced magnetic resonance imaging) was performed at screening (baseline), on Day 5 (optional) and Week 8. For patients going on to Sorafenib, DCE MRI was performed 4 and/or 8 weeks after the start of Sorafenib treatment. DCE MRI assesses tumor size, vascularity and necrosis. The screening/baseline DCE MRI was used as the reference from which to determine time to progression and response rates. The Day 5 (optional) DCE MRI was used to assess early effects such as acute vascular shutdown. Tumor progression status and tumor response(s) to JX-594 were assessed radiologically by modified RECIST and modified Choi criteria at the Week 8 visit. Independent review of the images was made by radiologist(s) with expertise in evaluating hepatocellular carcinoma on MRI scans. For evaluation of the intra-hepatic tumors, the proportion of subjects with an objective "complete" or "partial" anti-tumor response was determined based on modified RECIST, and a response as measured by Modified Choi criteria (defined as a ≥10% decrease in the sum of the longest diameter and/or ≥15% decrease in the average tumor signal intensity at MRI).

Tumor Response by Modified RECIST: The modifications to RECIST for measurement of tumor response and tumor progression were as follows. New tumor(s) that developed within the liver during or after treatment were measured. Their maximum diameter(s) was included in the sum of the maximum diameter of all intra-hepatic tumors. However, new tumors within the liver were not considered evidence for progression per se. The rationale for this RECIST criteria modification is the following. JX-594 infection of a tumor mass that was originally undetectable radiographically may make that tumor appear to be new and/or progressive due to inflammation and/or necrosis; however, these changes do not represent true tumor progression. In addition, because the treatment goal was to control the intra-hepatic tumor burden, new tumors detected extra-hepatically in the abdomen were be noted (and recorded by location) but were not included in the determination of overall response. Thus tumor response or progression was determined by the sum of the longest diameters of measurable intra-hepatic tumors and determined as follows: Complete Response (CR): Disappearance of all tumor(s). Partial Response (PR): At least a 30% decrease in the sum of the LD of tumor(s), taking as reference the baseline sum LD. Progressive Disease (PD): At least a 20% increase in the sum of the LD of tumor(s), taking as reference the baseline sum LD. Stable Disease (SD): Neither sufficient shrinkage to qualify for PR nor sufficient increase to qualify for PD, taking as reference the baseline sum LD.

Tumor Response by Modified Choi Criteria: The Choi response criteria takes into consideration changes in tumor density in addition to tumor diameter (versus RECIST) and data supporting its utility has been published (Choi et al. 2004). Early studies have shown that liver tumors treated with JX-594 can develop significant internal necrosis without a concomitant decrease in size, as has been described in gastrointestinal stromal tumors by Choi et al. (2004). Therefore, intra-hepatic tumors were also measured and response evaluated using a Modified Choi Criteria. The modification of the criteria is necessary as DCE MRI was the imaging modality employed for measuring tumor response. As MRI does not have a standardized system of contrast density measurements similar to CTs Hounsfield units, a comparison of percent enhancement of tumors at baseline and following treatment was performed using region of interest (ROI) signal intensity (SI) measurements. The screening/baseline DCE MRI was used as the reference from which to determine response. A response by Modified Choi criteria was defined as a ≥0.10% decrease in the sum of the longest diameter of the injected tumor(s) and/or ≥15% decrease in the average injected tumor signal intensity on MRI. The average MRI signal intensity (SI) was measured as a percentage of tumor.

MRI Imaging Protocols: Each patient will undergo MRI of the abdomen, including dynamic contrast-enhanced magnetic resonance imaging (DCE MRI), at time points prescribed by the protocol. Imaging will be performed on a 1.5 T or 3.0 T MR system using a body/torso array coil positioned for complete imaging coverage of the liver with the patient in the supine position. A dielectric pad may be placed over the liver.

Typically imaging parameters are fixed between patient follow-up visits. While the sequences below list a range of acceptable parameters, once a patient has had their initial scan, these parameters should be employed on all subsequent scans. In addition, a patient should be scanned using the same MRI scanner.

An intravenous line will be started prior to the examination with the largest gauge catheter possible placed in a peripheral vein with normal saline running at KVO. Alternatively, for patients with PICC lines or external venous catheter ports which are compatible with automated contrast injectors, these may be used for venous access. Extracellular gadolinium chelate contrast will be administered by intravenous bolus injection at 0.1 mmol/kg dose and at a rate of 2 cc/second via an automated injector, followed by an immediate injection of 20 cc saline. Any variations from the injection rate or dose, or extravasation of contrast, will be noted in the CRF.

Imaging protocol for 1.5 tesla MR systems: The following pulse sequences sill be performed:

Precontrast Imaging: (1) 2D Axial In- and Opposed Phase T1: T1-weighted spoiled gradient echo (SPGR) dual phase axial images (TR: shortest possible; TE: 2.1 and 4.2; flip angle (FA): 80-90 degrees, slice thickness 5-7 mm, slice gap maximum 1 mm; phase encodes 160-192 interpolated to 256×256; field of view optimized to the patient's body habitus, 300-450 mm. (2) 2D FSE T2 Axial: TR: 3500-5000 msec (effective); TE: 60-88 msec; phase encodes: 160-256×256; field of view optimized to the patient's body habitus, 300-450 mm; slice thickness, 5-7 mm; maximum slice gap 1 mm; imaging should be performed with fat suppression. Respiratory trigging or other motion suppression techniques are encouraged.

DCE-MRI: (3) 3D T1 Dynamic imaging: A total of 6 sets of this sequence are performed: one precontrast, 4 immediate postcontrast, and one 5 minute delayed image set. Parameters for the 3D T1-weighted fat-suppressed acquisitions are as follows: TR=2.0-4.5 msec; TE=1.42-2.0 msec; flip angle, 8-12°; phase encodes 160-192 interpolated to 512×512; field of view optimized to the patient's body habitus, 300-450 mm; interpolated section thickness, 1.5-3 mm; slab thickness to ensure complete coverage of the liver.

To determine the timing for the first contrast-enhanced acquisition (hepatic arterial phase), a 1-2 mL test bolus of contrast material will be administered and the circulation time (time to peak arterial enhancement) will be set as the acquisition delay time. Alternatively, if automated timing software is available to determine arterial phase enhancement, this may also be used. The 4 postcontrast dynamic sequences will be performed with a 40 second time gap between each acquisition. An additional delayed sequence will also be acquired at 5 minutes following injection (for a total of 5 post-contrast sequences). All acquisitions will be performed during suspended respiration, either inspiration or expiration based on institutional practices. The system does not undergo any tuning changes between the pre- and post-contrast sequences. Any variations from this imaging protocol will be noted in the CRF.

Imaging protocol for 3.0 tesla MR systems: The following pulse sequences will be performed:

Precontrast Imaging: (1) T1w 2D Axial In-Phase (IP) and Out-of-Phase (OP): dual-phase spoiled gradient echo (SPGR). FOV: optimized to body habitus, 300-450 mm; TR: minimum to cover liver; TE: default in phase and opposed phase TE's; Flip angle: 80-90 degrees; Slice thickness: 5-7 mm; Gap: 0-1 mm (0-mm gap preferred); Frequency matrix: 320; Phase encodes: 160-224, interpolated to 512×512; Fat sat: off; Bandwidth: default setting.

(2) T2w 2D Axial SSFSE. FOV: use same as (1) above; TR: shortest effective TR to image complete liver; TE effective: 60-88 msec; Slice thickness: use same as (1); Gap: use same (1); Frequency matrix: 320; Phase encodes: 160-224, interpolated to 512×512; Fat sat: off.

(3) T2w 2D Axial FSE. Either free breathing with respiratory triggering or breathhold imaging can be used here. However, it will be standardized within a patient's exams. For example, if a patient is scanned at baseline using respiratory triggering, all subsequent MR exams will use respiratory triggering with this sequence. If respiratory triggering is used, an echo train length of 12-20 should be employed, as should be sufficient excitations/acquisitions for optimal signal to noise. If breath-hold T2 imaging is performed, employ an echo train length of 24-32 and 1 acquisition. FOV: use same as (1) above. TR effective: 3500-5000; Slice thickness: use same as (1); Gap: use same as (1); Frequency matrix: 320; Phase encodes: 160-224, interpolated to 512×512; Fat sat: on. DCE MRI (4) T1w 3D Axial spoiled gradient echo (SPGR). FOV: use same as (1) above; TR: 2-5 msec; TE: 1.4-2.5; Flip angle: 8-15; Slice thickness: 1.5-3 mm interpolated; Slab thickness: cover entire liver; Frequency matrix: 288-320; Phase encodes: 160-224, interpolated to 512×512; Fat sat: on. Number of scans: 5 total (1 pre and 4 post-contrast scans, followed by a 5th scan at 5 minutes following contrast injection). All scans performed during suspended respiration, either at end expiration or end inspiration per standard institutional practice.

Figure 7:
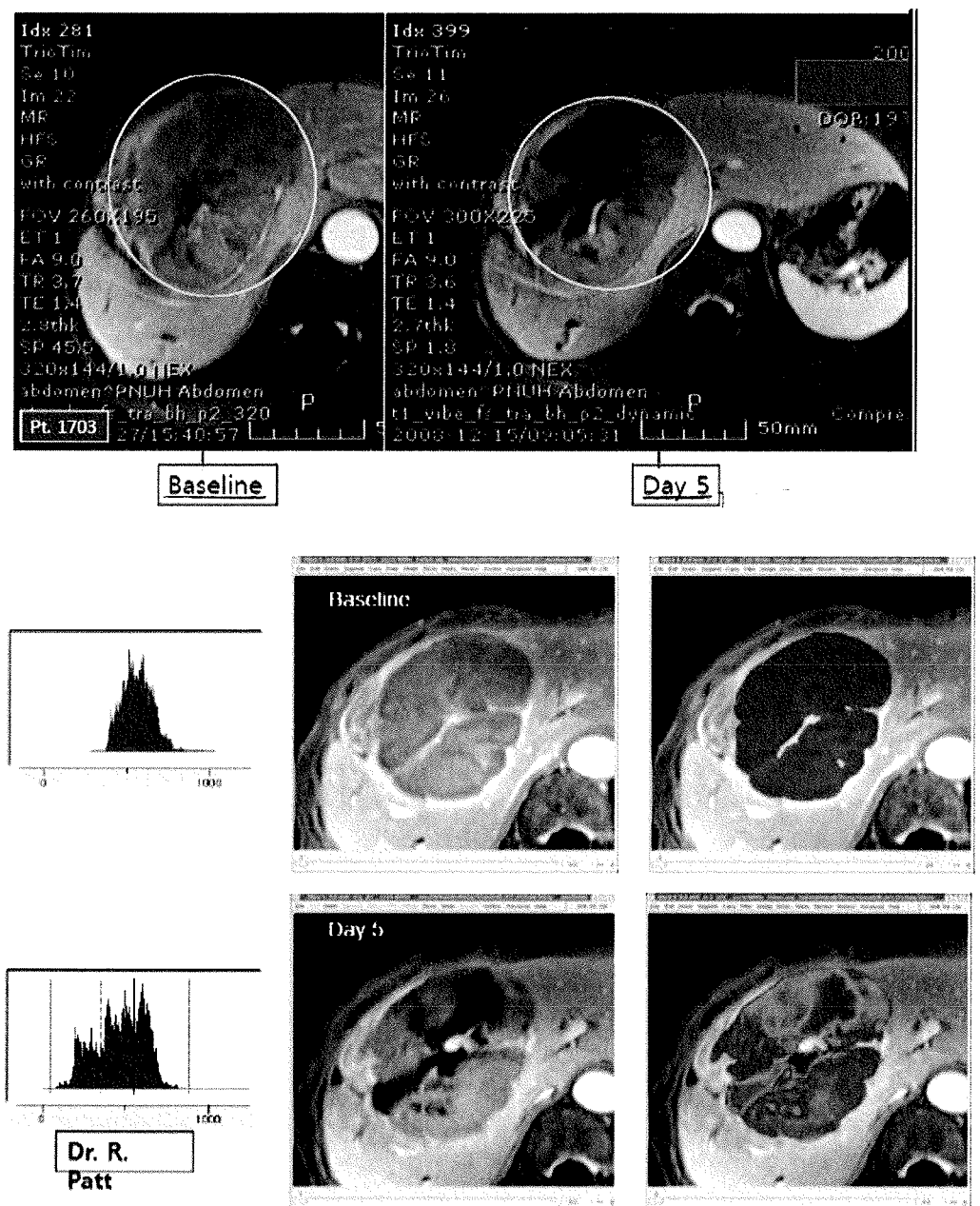
FIG. 7 DCE-MRI scan of HCC patient showing vascular shutdown.

D. Clinical trial data: Day 5 vascular Shutdown in tumors and colorectal carcinoma tumors after JX-594 treatment Acute vascular shutdown as measured by perfusion CT was previously seen in tumors treated directly with JX-594 by intratumoral injection (Liu et al., 2008). The inventors have applied DCE MRI analysis to follow reduction in perfusion of tumors to follow the course of vascular shutdown and tumor necrosis in response to JX-594 treatment. Of the 16 patients enrolled in a new clinical trial with optional DCE-MRI scanning on Day 5, 13 have received such scans, and there are additional examples of vascular shutdown in patients with hepatocellular carcinoma (HCC) (FIG. 7).

Figure 8:
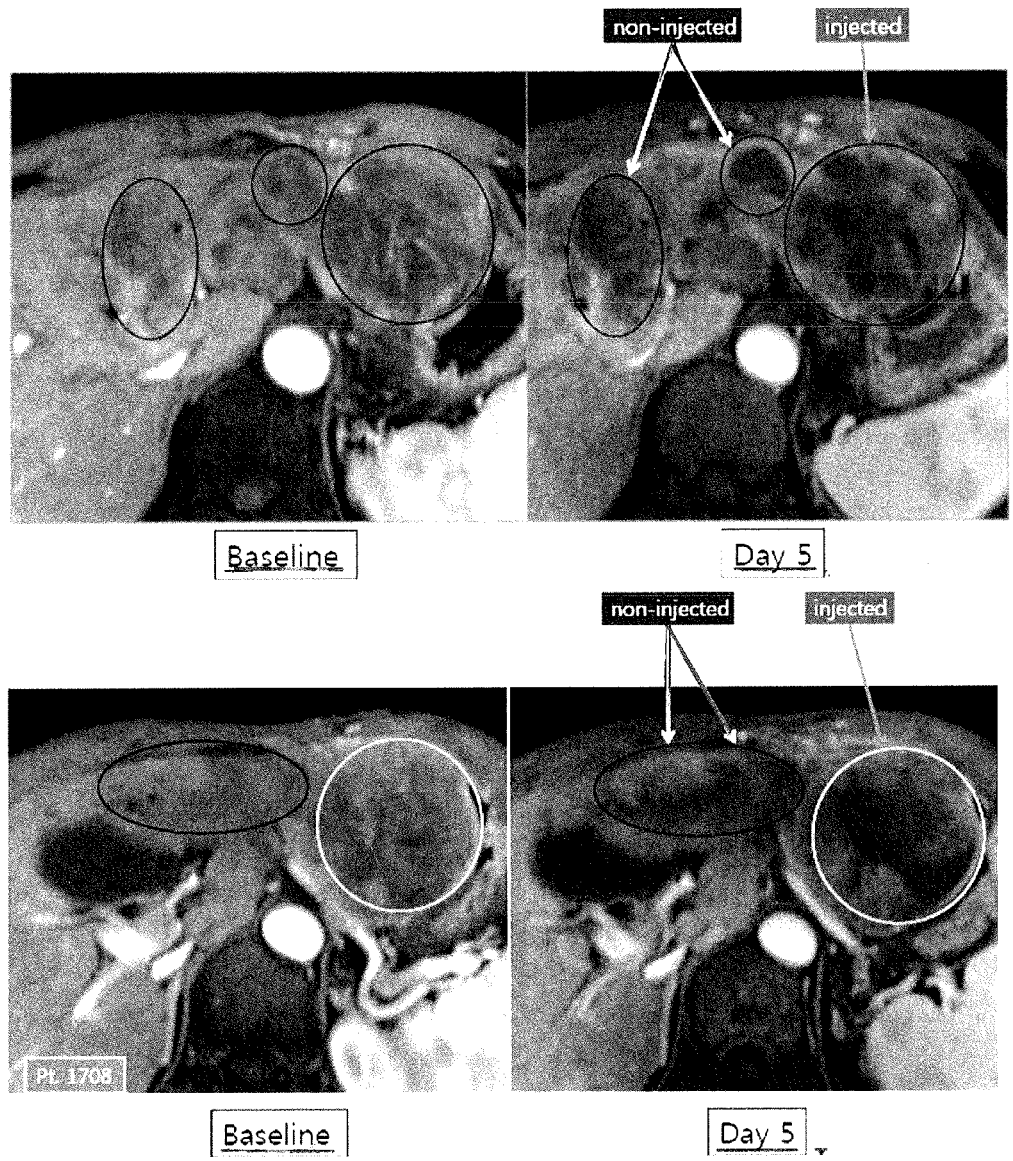
FIG. 8 DCE-MRI scans showing response in sites distant to intratumoral injection cites.
Figure 9:
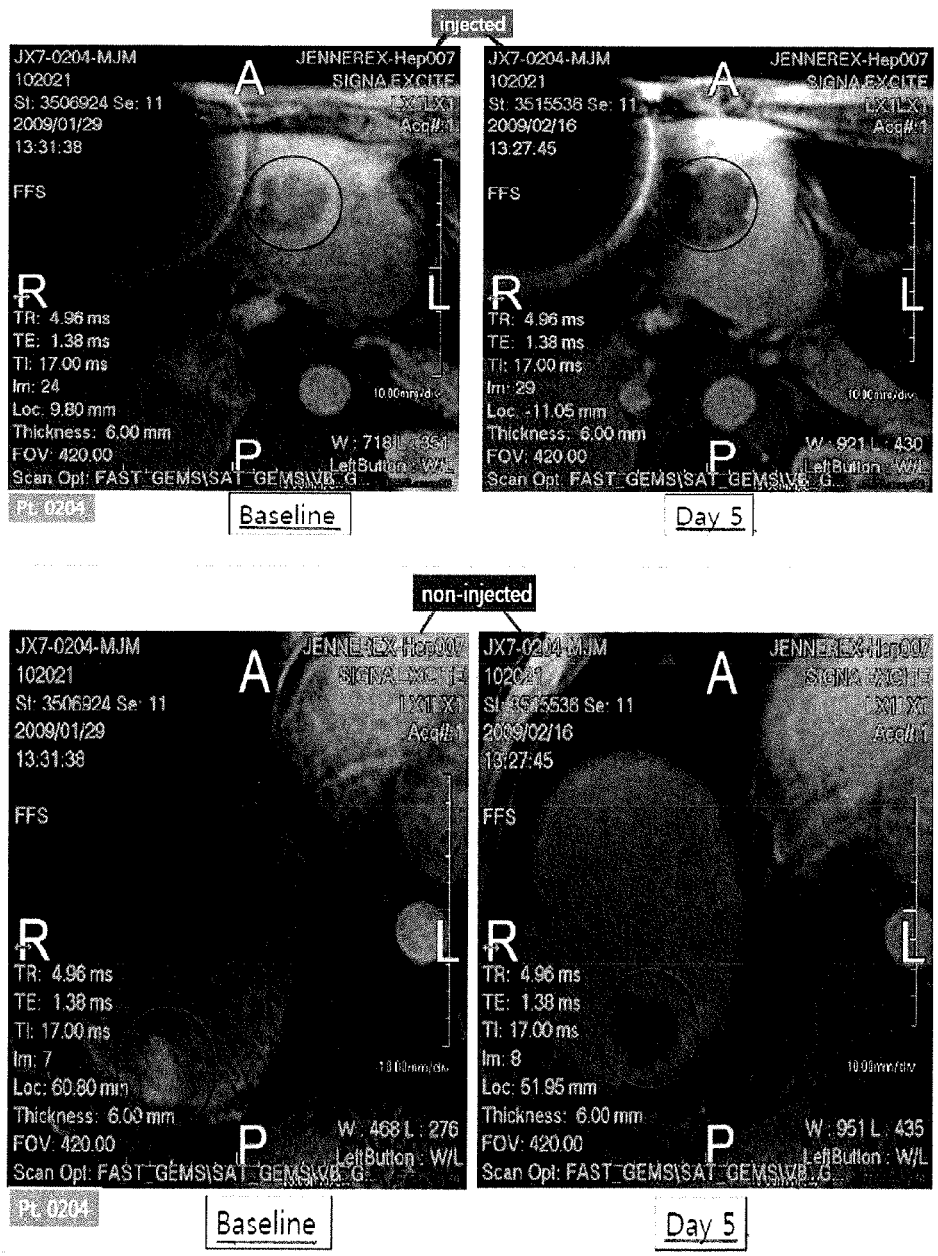
FIG. 9 DCE-MRI scans showing response in sites distant to intratumoral injection cites.

In the HCC examples previously analyzed, it had appeared that direct tumor injection was necessary to cause reduced tumor perfusion (FIG. 1, Liu et al., 2008). From this data, it was not predicted that vascular shutdown would occur in non-injected tumors in response to distant application of JX-594. Now, for the first time, the inventors show that it is not necessary to inject every tumor to have this response, and that distant, non-injected tumors can also show vascular shutdown (FIGS. 8 and 9).

Furthermore, the inventors demonstrate that JX-594 can cause vascular shutdown in non-HCC tumors as evidenced in a patient with liver-based metastases of colorectal carcinoma (CRC), a tumor type considered less well-vascularized than HCC (FIG. 9), and therefore potentially less likely to incur vascular changes.

Example 1703: Patient 1703 had hepatocellular carcinoma and was enrolled in a Phase 2 Clinical Trial of JX-594. JX-594 was injected into a single large tumor ($10^9$ pfu/dose). After five days, DCE MRI showed acute vascular shutdown (top black and white panels)(FIG. 9). Bottom panels show an example of segmentation analysis used to quantify the extent of vascular shutdown/tumor necrosis (bottom panels)(FIG. 7).

Example 1708: Patient 1708 had hepatocellular carcinoma, with multiple tumors present in the liver and was enrolled in a Phase 2 Clinical Trial of JX-594. JX-594 was injected into some but not all of the liver tumors (total dose of $10^8$ pfu/dose). After five days, DCE MRI showed acute necrosis/vascular shutdown in injected and non-injected liver-based tumors. FIG. 8 shows two planes of view, including images both before and after JX-594 treatment.

Example 0204: Patient 0204 had colorectal carcinoma, with metastases present in the liver, lung and lymph nodes and was enrolled in a Phase 2 Clinical Trial of JX-594. JX-594 was injected into some but not all of the liver metastases (total dose of $10^9$ pfu/dose). After five days, DCE MRI showed acute necrosis/vascular shutdown in injected and non-injected liver-based tumors. (FIG. 9)

Figure 11:
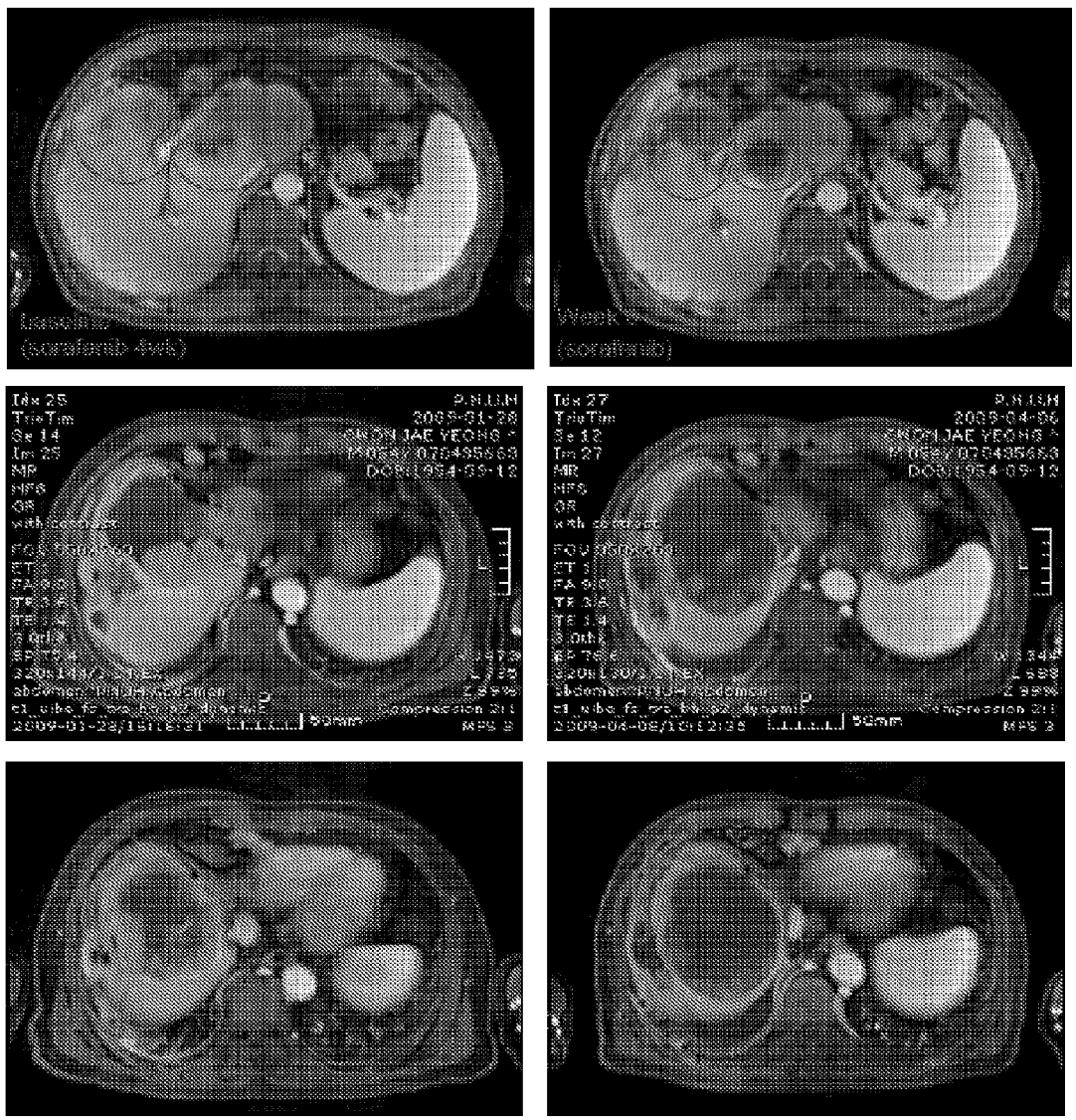
FIG. 11 Patient 1702—DCE-MRI Images 4 weeks and 8 weeks Post-Sorafenib Treatment (3 different planes are shown, with 4 week and 8 week images of each plane).
Figure 13:
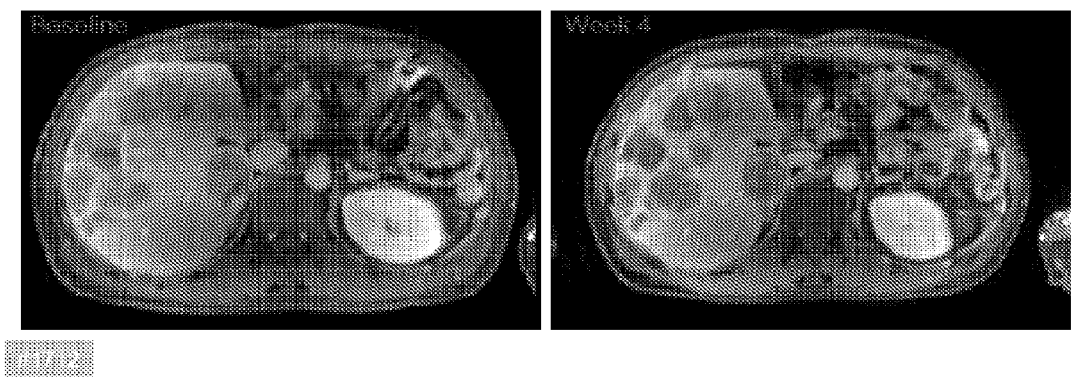
FIG. 13 Patient 1712—DCE-MRI images before and 4 weeks post-Sorafenib treatment.

E. Clinical trial data: JX-594 potentiates sorafenib and sutent anti-VEGF therapy Five patients showing reperfusion on Week 8 after completing JX-594 treatment subsequently received standard sorafenib dosing (400 mg twice daily). Enhanced Choi responses were seen (Table A). These responses were enhanced over any initial Choi response to JX-594 treatment alone (FIGS. 11, 12, and 13)

TABLE A

Enhanced Choi Response in Patients treated with JX-594 followed by sorafenib.

| Patient | Dose Level | RECIST Response to JX-594, Week 8 | CHOI Response to JX-594, Week 8 | CHOI response to sorafenib |
|---|---|---|---|---|
| 1702 | $10^9$ pfu/dose | SD (inj) PD (new) | Not evaluable | Choi+ |
| 1705 | $10^8$ pfu/dose | PD | Choi+ −36% | Choi+ |
| 1002 | $10^9$ pfu/dose | SD (inj) PD (new) | Choi+ −121% | TBD |
| 1712 | $10^9$ pfu/dose | PD | Choi+ −33% | Choi+ |
| 1713 | $10^9$ pfu/dose | PD | Choi− | TBD |

Example Sorafenib Only "Control Group" (Figure Included): Historically, the RECIST response rate to sorafenib alone is 1-2% (Llovet et al., 2008; Cheng et al., 2009). For a local control group assessed by Choi criteria, HCC patients that had not received JX-594, but had received sorafenib, were assessed for Choi response. In the hospital where 4 of the 5 JX-594 patients were treated, 26 other patients had received sorafenib in the same period. 7 patients died prior to response assessment, and 15 patients were assessed for Choi response. Only 2 of sorafenib-only patients showed a Choi+ response (26 total; 15 assessed for Choi response). It should be noted that both of these patients had received radiation therapy in conjunction with sorafenib therapy. In comparison, the two patients who had received JX-594 therapy prior to sorafenib therapy during this period had a Choi+ response (FIG. 10), a surprising and extraordinary improvement in sorafenib effect on tumors.

In a sorafenib-only clinical trial which used MRI scans to assess tumor necrosis, some hepatic masses displayed central tumor necrosis, with moderate increase in mean tumor necrosis from 9.8% at baseline to 27% after several courses of treatment (Abou-Alfa et al., 2006).

Example 1702: Patient 1702 had hepatocellular carcinoma and was enrolled in a Phase 2 clinical trial for JX-594 and received three intratumoral doses of JX-594 ($10^9$ pfu/dose given two weeks apart). This patient was not evaluable for response to JX-594 using modified Choi criteria, however week 8 scans showed stable disease (SD) in injected tumors but progressive disease (PD) due to emergence of new tumors using modified RECIST criteria. Therefore, Patient 1702 went on to receive a standard course of Sorafenib treatment for 8 weeks (200 mg twice daily p.o.). DCE MRI scans taken at 4 and 8 weeks after initiation of Sorafenib treatment showed acute tumor necrosis. FIG. shows three different planes, with images on the left from 4 weeks post-Sorafenib treatment and images on the right from 8 weeks post-Sorafenib treatment. (FIG. 11)

Figure 15:
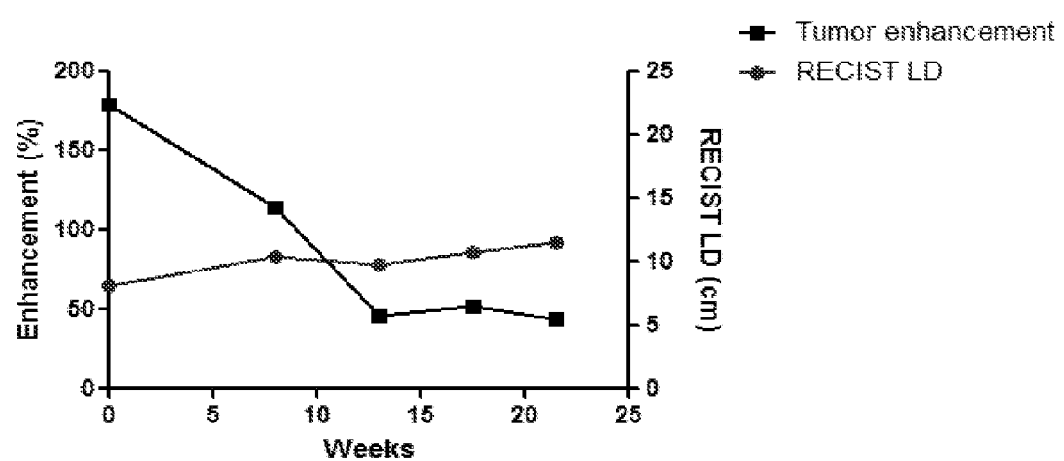
FIG. 15 Illustration of tumor stabilization and decreased enhancement observed with sequential JX-594 and sorafenib (Patient 1705).

Example 1705: Patient 1705 had hepatocellular carcinoma and was enrolled in a Phase 2 Clinical Trial of JX-594. Five days after the first dose of JX-594, a marked reduction in perfusion by DCE MRI confirmed vascular shutdown occurred in the tumors (top panels). After completing JX-594 administration (three intratumoral doses of $10^8$ pfu/dose given two weeks apart), week 8 scans showed a response by modified CHOI criteria (−36%), but progressive disease (PD) by modified RECIST criteria. Therefore, Patient 1705 went on to receive a standard course of Sorafenib treatment for 4 weeks (400 mg twice daily p.o.). DCE MRI scans taken at 4 weeks showed acute tumor necrosis (bottom right panel). (FIG. 12, FIG. 15, FIG. 16))

Example 1712: Patient 1712 had hepatocellular carcinoma and was enrolled in a Phase 2 Clinical Trial of JX-594. After completing JX-594 administration (three intratumoral doses of $10^9$ pfu/dose given two weeks apart), week 8 scans showed a response by modified CHOI criteria (−33%), but progressive disease (PD) by modified RECIST criteria. Patient 1712 received a standard course of Sorafenib treatment for 4 weeks (400 mg twice daily p.o.). DCE-MRI scans taken at 4 weeks showed acute tumor necrosis. (FIG. 13)

Figure 14:
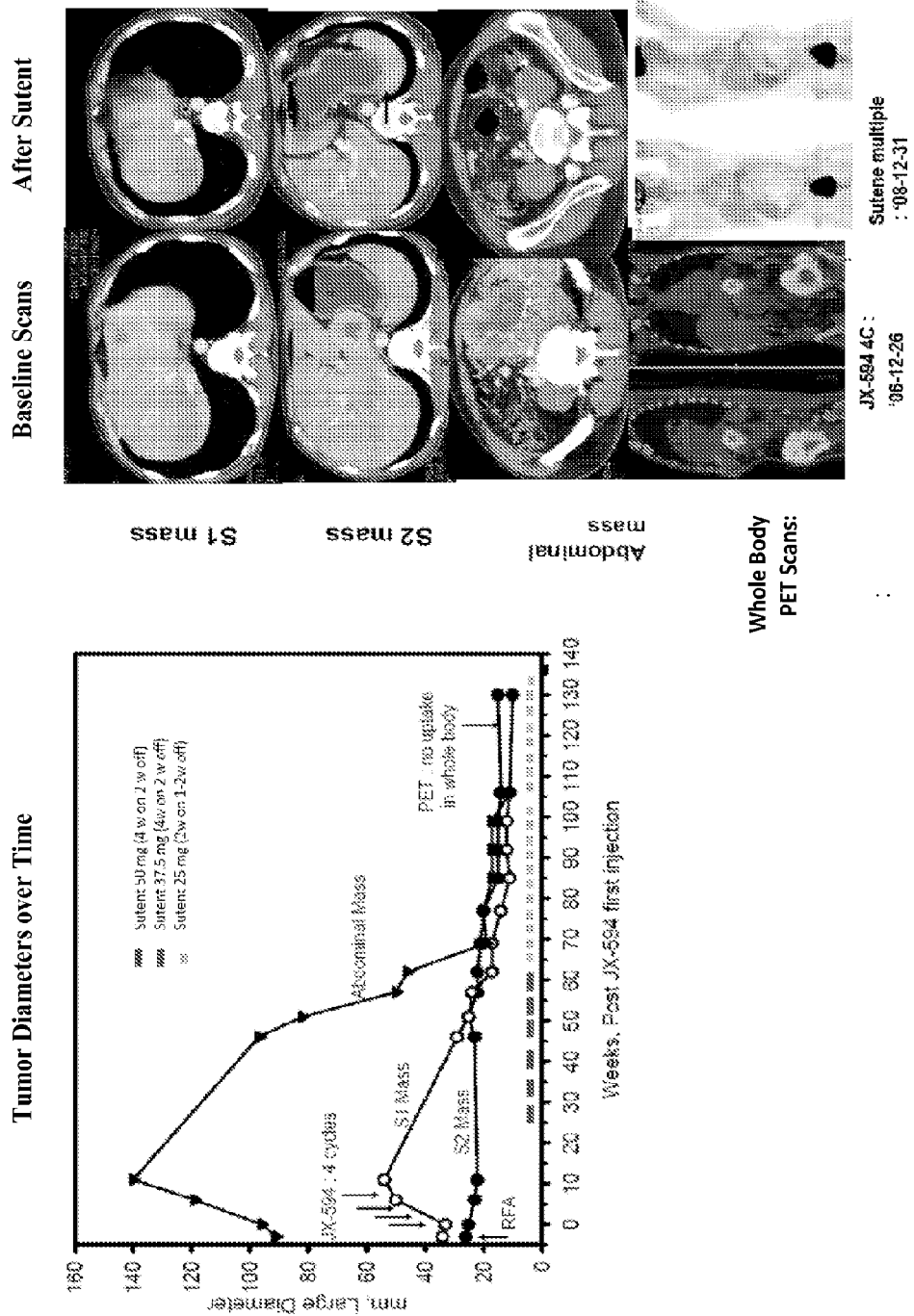
FIG. 14 Patient 11301—assessment of patient with renal cell carcinoma metastasis to liver.

Example 11301: Sutent Patient: Sutent is another targeted cancer therapy approved for renal cell carcinoma (RCC) that inhibits VEGF activity and angiogenesis. Patient 11301 had RCC with metastases to the liver and was enrolled in a Phase 1 Clinical Trial of JX-594 for treatment of liver-based tumors. After completing 2 courses of JX-594 administration (intratumoral doses of $10^9$ pfu/dose given three weeks apart), week 6 assessment showed stable disease by RECIST. The patient received two more courses of JX-594 treatment yet one liver mass and a large (14 cm) abdominal mass progressed. Therefore, Patient 1705 went on to receive sutent therapy. Prognosis for the patient was poor based on low hemoglobin and extent of liver metastases (Motzer et al., 2006). Surprisingly, a complete response in all of the patient's tumors followed (FIG. 14). Whole body PET scanning showed no signal. Survival post-JX-594 treatment is 3 years+(patient is still alive). In comparison, historical RCC complete response rate to sutent alone in tumors greater than 10 cm is 0%. Less than 5% of RCC patients with poor prognosis have survival of 3 years.

Figure 18:
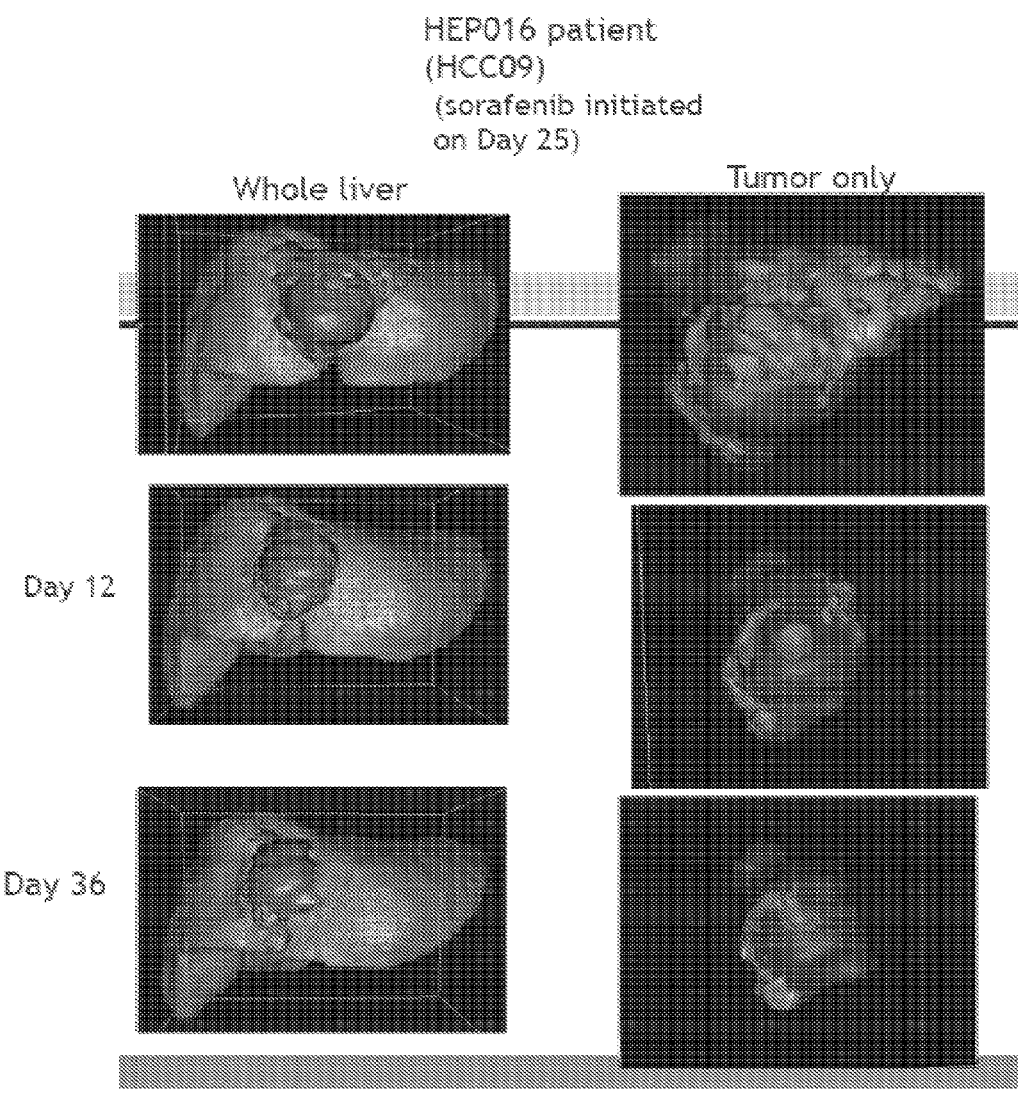
FIG. 18 DCE-MRI scans of Patient having hepatocellular carcinoma and was enrolled in a Phase 2 Clinical Trial of JX-594 showed loss of perfusion 10 days after sorafenib initiation in a non-injected extahepatic tumor. After completing JX-594 administration (one intravenous and two intratumoral doses) patient received sorafenib.

Example JX16-HCC-03, IV+IT+IT+Sorafenib Patient: Patient JX16-HCC-03 had hepatocellular carcinoma and was enrolled in a Phase 2 Clinical Trial of JX-594. After completing JX-594 administration (one intravenous and two intratumoral doses) patient received sorafenib. DCE-MRI scans showed loss of perfusion 10 days after sorafenib initiation in a non-injected extahepatic tumor (FIG. 18)

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,683,202
U.S. Pat. No. 4,684,611
U.S. Pat. No. 4,952,500
U.S. Pat. No. 5,073,627
U.S. Pat. No. 5,302,523
U.S. Pat. No. 5,322,783
U.S. Pat. No. 5,384,253

U.S. Pat. No. 5,399,363
U.S. Pat. No. 5,464,765
U.S. Pat. No. 5,466,468
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,633,016
U.S. Pat. No. 5,641,515
U.S. Pat. No. 5,656,610
U.S. Pat. No. 5,702,932
U.S. Pat. No. 5,736,524
U.S. Pat. No. 5,739,169
U.S. Pat. No. 5,780,448
U.S. Pat. No. 5,789,215
U.S. Pat. No. 5,798,339
U.S. Pat. No. 5,801,005
U.S. Pat. No. 5,824,311
U.S. Pat. No. 5,824,348
U.S. Pat. No. 5,830,880
U.S. Pat. No. 5,846,225
U.S. Pat. No. 5,846,233
U.S. Pat. No. 5,846,945
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
Abou-Alfa G K, Schwartz L, Ricci S, Amadori D, Santoro A, Figer A, De Greve J, Douillard J Y, Lathia C, Schwartz B, Taylor I, Moscovici M, Saltz L B. (2006) Phase II study of sorafenib in patients with advanced hepatocellular carcinoma. J Clin Oncol 24(26):4293-300.
Alcami and Smith, Cell., 71(1):153-167, 1992.
Alcami et al., J. Gen. Virol., 80:949-959, 1999.
Alcami et al., Sem. Virol., 5:419-427, 1998.
Alcami et al., Virology, 74(23):11230-11239, 2000.
Almendro et al., J. Immunol., 157(12):5411-5421, 1996.
Arap et al., Cancer Res., 55(6):1351-1354, 1995.
Arness et al., Am. J. Epidemiol., 160:642-51, 2004.
Austin-Ward and Villaseca, Revista Medica de Chile, 126(7): 838-845, 1998.
Ausubel et al., In: Current Protocols in Molecular Biology, John, Wiley & Sons, Inc, NY, 16.15.1-16.18.10, 1996.
Bajorin et al., J. Clin. Oncol., 6(5):786-792, 1988.
Bakhshi et al., Cell, 41(3):899-906, 1985.
Blasco and Moss, J. Virology, 66(7): 4170-4179, 1992.
Blasco et al., J. Virology, 67(6):3319-3325, 1993.
Boyd et al., Cell, 79:341-351, 1994.
Bretibach, C. J., Paterson, J. M., Lemay, C. G., et al. (2007) Targeted Inflammation During Oncolytic Virus Therapy Serverely Compromises Tumor Blood Flow. Mol Ther 15(9):1686-1693.
Brizel, Semin. Radiat. Oncol., 8(4):237-246, 1998.
Bukowski et al., Clinical Cancer Res., 4(10):2337-2347, 1998.
Caldas et al., Cancer Res., 54:3568-3573, 1994.
Carbonelli et al., FEMS Microbiol. Lett., 177(1):75-82, 1999.
Cebon et al., Br. J. Haematol., 80(2):144-150, 1992.
Chandler et al., Proc. Natl. Acad. Sci. USA, 94(8):3596-601, 1997.
Chen and Okayama, Mol. Cell Biol., 7(8):2745-2752, 1987.
Cheng A L, Kang Y K, Chen Z, Tsao C J, Qin S, Kim J S, Luo R, Feng J, Ye S, Yang T S, Xu J, Sun Y, Liang H, Liu J, Wang J, Talc W Y, Pan H, Burock K, Zou J, Voliotis D, Guan Z. (2009) Efficacy and safety of sorafenib in patients in the Asia-Pacific region with advanced hepatocellular carcinoma: a phase III randomised, double-blind, placebo-controlled trial. Lancet Oncol. 10(1):25-34.
Cheng et al., Cancer Res., 54(21):5547-5551, 1994.
Choi et al., J. Clin. Oncol., 25(13):1753-1759, 2007.
Choi H, Charnsangavej C, de Castro Faria S et al. (2004) CT evaluation of the response of gastrointestinal stromal tumors after imatinib mesylate treatment: a quantitative analysis correlated with FDG PET findings. American Journal of Roentgenology 183:1619-1628.
Christodoulides et al., Microbiology, 144(Pt 10:3027-3037, 1998.
Cleary and Sklar, Proc. Natl. Acad. Sci. USA, 82(21):7439-7443, 1985.
Cleary et al., J. Exp. Med., 164(1):315-320, 1986.
Cocea, Biotechniques, 23(5):814-816, 1997.
Colamonici et al., J. Biol. Chem., 270:15974-15978, 1995.
Culver et al., Science, 256(5063):1550-1552, 1992.
Curran, Seminars Radiation Oncol., 8(4 Suppl):2-4, 1998.
Davidson et al., J. Immunother., 21(5):389-398, 1998.
Dillman, Cancer Biother. Radiopharm., 14(1):5-10, 1999.
Dobbelstein and Shenk, J. Virology, 70:6479-6485, 1996.
Durrant and Spendlove, Curr. Opin. Investig. Drugs, 2(7): 959-66, 2001.
Eliopoulos et al., Oncogene, 11(7):1217-28, 1995.
Erlandsson, Cancer Genet. Cytogenet., 104(1):1-18, 1998.
Escudier B, Eisen T, Stadler W M, Szczylik C, Oudard S, Siebels M, Negrier S, Chevreau C, Solska E, Desai A A, Rolland F, Demkow T, Hutson T E, Gore M, Freeman S, Schwartz B, Shan M, Simantov R, Bukowski R M (2007) Sorafenib in advanced clear-cell renal-cell carcinoma. N Engl J Med. 2007 Jan. 11; 356(2):125-34
Fechheimer et al., Proc Natl. Acad. Sci. USA, 84:8463-8467, 1987.
Fraley et al., Proc. Natl. Acad. Sci. USA, 76:3348-3352, 1979.
GenBank Accession Number NC001559
Gnant et al., Ann Surg, 230(3):352-360, 1999.
Gnant et al., Cancer Res., 59(14):3396-403, 1999.
Gnant et al., J. Natl. Cancer Inst., 91(20):1744-1750, 1999.
Goebel et al., Virology, 179(1):247-266, 517-563, 1990.
Gopal, Mol. Cell Biol., 5:1188-1190, 1985.
Graham and Van Der Eb, Virology, 52:456-467, 1973.
Graham et al., Virology, 229(1):12-24, 1997.
Gross et al., Genes Dev., 13(15):1899-911, 1999.
Gross et al., J. Biol. Chem., 274:1156-1163, 1999.
Hanibuchi et al., Int. J. Cancer, 78(4):480-485, 1998.
Harland and Weintraub, J. Cell Biol., 101(3):1094-1099, 1985.
Heise et al., Cancer Gene Ther., 6(6):499-504, 1999.
Heise et al., Cancer Res., 59(11):2623-2628, 1999.
Hellstrand et al., Acta Oncologica, 37(4):347-353, 1998.
Hengstschlager, M., et al. 1994. Different regulation of thymidine kinase during the cell cycle of normal versus DNA tumor virus-transformed cells. J. Biol. Chem. 269:13836-13842.
Hermiston, J. Clin. Invest., 105:1169-1172, 2000.
Ho et al., J. Biol. Chem., 27:7765-7769, 1998.
Homey et al., Nature. Rev. Immunol., 2:175-184, 2002.
Hui and Hashimoto, Infection Immun., 66(11):5329-5336, 1998.
Hussussian et al., Nat. Genet., 8(1):15-21, 1994.
Ikeda et al., Nat. Med., 5(8):881-7, 1999.

Inouye and Inouye, *Nucleic Acids Res.*, 13:3101-3109, 1985.
Irie and Morton, *Proc. Natl. Acad. Sci. USA,* 83(22):8694-8698, 1986.
Irie et al., *Lancet.*, 1(8641):786-787, 1989.
Isaacs et al., *Proc. Natl. Acad. Sci. USA,* 89(2):628-32, 1992.
Johnson and Hamdy, *Oncol. Rep.,* 5(3):553-557, 1998.
Ju et al., *Gene Ther.,* 7(19):1672-1679, 2000.
Ju et al., *J. Neuropathol. Exp. Neurol.,* 59(3):241-250, 2000.
Kaeppler et al., *Plant Cell Reports,* 9:415-418, 1990.
Kamb et al., *Nat. Genet.,* 8(1):23-26, 1994.
Kamb et al., *Science,* 2674:436-440, 1994.
Kaneda et al., *Science,* 243:375-378, 1989.
Kato et al, *J. Biol. Chem.,* 266:3361-3364, 1991.
Kay et al., *Proc. Natl. Acad. Sci. USA,* 94(9):4686-4691, 1997.
Kerr et al., *Br. J. Cancer,* 26(4):239-257, 1972.
Kettle et al., *J. Gen. Virology,* 78:677-685, 1997.
Kim et al., *Nat. Med.,* 7:781-787, 2001.
Kolmel, *J. Neurooncol.,* 38(2-3):121-125, 1998.
Kraus et al. *FEBS Lett.,* 428(3):165-170, 1998.
Kulesh et al., *J. Clin. Microbiol.,* 42(2):601-609, 2004.
Kyte and Doolittle, *J. Mol. Biol.,* 157(1):105-132, 1982.
Lareyre et al., *J. Biol. Chem.,* 274(12):8282-8290, 1999.
Lee et al., *Biochem. Biophys. Res. Commun.,* 238(2):462-467, 1997.
Levenson et al., *Hum. Gene Ther.,* 9(8):1233-1236, 1998.
Liebeimann, *Oncogene,* 17(10):1189-94, 1998.
Liu, T. C., Hwang, T. H., Park, B. H., Bell, J. and Kim, D. H. (2008) The targeted oncolytic poxvirus JX-594 demonstrates antitumoral, antivascular, and anti-HBV activities in patients with hepatocellular carcinoma. Mol Ther 16(9): 1637-42.
Llovet J, Ricci S, Mazzaferro V, Hilgard P, Gane E, Blanc J-F, Cosme de Oliveira A, Santoro A, Raoul J-L, Forner A, Schwartz M, Porta C, Aeuzem S, Bolondi L, Greten T F, Galle P R, Seitz J-F, Borbath I, Haussinger D, Giannaris T, Shan M, Moscovici M, Voliotis D, Bruix J. (2008) Sorafenib in advanced Hepatocellular Carcinoma (HCC). N Engl J Med 359:378-90.
Macejak and Sarnow, *Nature,* 353:90-94, 1991.
Magi-Galluzzi et al., *Anal. Quant. Cytol. Histol.,* 20(5):343-350, 1998.
Mangray and King, *Front Biosci.,* 3:D1148-1160, 1998.
Marsters et al., *Recent Prog. Horm. Res.,* 54:225-234, 1999.
Mastrangelo et al., *Cancer Gene Ther.,* 6(5):409-422, 1999.
Mastrangelo et al., *Cancer Treat Res.,* 94:35-50, 1998.
Mayer et al., *Radiat. Oncol. Investig.,* 6(6):281-288, 1998.
McCart et al., *Gene Ther.,* 7(14):1217-23, 2000.
Mitchell et al., *Ann. NY Acad. Sci.,* 690:153-166, 1993.
Mitchell et al., *J. Clin. Oncol.,* 8(5):856-869, 1990.
Mori et al., *Cancer Res.,* 54(13):3396-3397, 1994.
Morton et al., *Arch. Surg.,* 127:392-399, 1992.
Moss, In: *Fields Virology.,* Fields (Ed.), Lippincott-Raven Publishers: Philadelphia, 2637-2672, 1996.
Mossman et al., *Virology,* 215(1):17-30, 1996.
Motzer R J, Rini B I, Bukowski R M, Curti B D, George D J, Hudes G R, Redman B G, Margolin K A, Merchan J R, Wilding G, Ginsberg M S, Bacik J, Kim S T, Baum C M, Michaelson M D. (2006) Sunitinib in patients with metastatic renal cell carcinoma. JAMA. 295(21):2516-24
Mougin et al., *Ann. Biol. Clin.*, (Paris) 56(1): 21-8, 1998.
Mumby and Walter, *Cell Regul.,* 2(8):589-98, 1991.
Natoli et al., *Biochem. Pharmacol.,* 56(8):915-20, 1998.
Nicolau and Sene Nobori et al., 1994
Nomoto et al., *Gene,* 236(2):259-271, 1999.
Ochi et al., *Am. J. Gastroenterol.,* 93(8):1366-1368, 1998.
Ohara, *Gan To Kagaku Ryoho,* 25(6): 823-828, 1998.

Okamoto et al., *Proc. Natl. Acad. Sci. USA,* 91(23):11045-11049, 1994.
Omirulleh et al., *Plant Mol. Biol.,* 21(3):415-428, 1993.
Orlow et al., *Cancer Res,* 54(11):2848-2851, 1994.
Park B H, Hwang T H, et al. (2008) Use of a targeted oncolytic poxvirus, JX-594, in patients with refractory primary or metastatic liver cancer: a phase I trial. Lancet Oncology 9: 533-42.
PCT Appln. WO 94/09699
PCT Appln. WO 95/06128
Pelletier and Sonenberg, *Nature,* 334(6180):320-325, 1988.
Pietras et al., *Oncogene,* 17(17):2235-2249, 1998.
Puhlmann et al., *Cancer Gene Ther.,* 7:66-73, 2000.
Qin et al., *Proc. Natl. Acad. Sci. USA,* 95(24):14411-14416, 1998.
Ravindranath and Morton, *Intern. Rev. Immunol.,* 7: 303-329, 1991.
Remington's Pharmaceutical Sciences" 15$^{th}$ Ed., 1035-1038 and 1570-1580, 1990.
Rippe, et al., *Mol. Cell Biol.,* 10:689-695, 1990.
Rosel et al., *J. Virol.,* 60(2):436-449, 1986.
Rosenberg et al., *Ann. Surg.* 210(4):474-548, 1989.
Rosenberg et al., *N. Engl. J. Med.,* 319:1676, 1988.
Sambrook et al., In: *Molecular cloning: a laboratory manual,* 2$^{nd}$ Ed., Cold Spring Harbor Laboratory Press, Cold Spring Harbor, N.Y., 1989.
Saraiva and Alcami, *J. Virology,* 75(1):226-33, 2001.
Serrano et al., *Nature,* 366:704-707, 1993.
Serrano et al., *Science,* 267(5195):249-252, 1995.
Sinkovics and Horvath, *J. Clin. Viro.,* 16:1-15, 2000.
Smith et al., *Immunol. Rev.,* 159:137-154, 1997.
Smith et al., *J. Clin. Oncol.,* 18:2046-2052, 2000.
Smith et al., *Neuron.,* 20:1093-1102, 1998.
Solyanik et al., *Cell. Prolif.,* 28(5):263-278, 1995.
Spriggs et al., *Cell.,* 71(1):145-52, 1992.
Stokke et al., *Cell. Prolif.,* 30(5):197-218, 1997.
Symons et al., *Cell,* 81:551-560, 1995.
Todo et al., *Cancer Res.,* 61:153-161, 2001.
Tsujimoto and Croce, *Proc. Natl. Acad. Sci. USA,* 83(14): 5214-5218, 1986.
Tsujimoto et al., *Nature,* 315:340-343, 1985.
Tsujimoto et al., *Science,* 228(4706):1440-1443, 1985.
Tsumaki et al., *J. Biol. Chem.,* 273(36):22861-22864, 1998.
Upton et al., *Science,* 258(5086):1369-1372, 1992.
Upton et al., *Virology,* 184(1):370-82, 1991.
Vanderplasschen et al., *Proc. Natl. Acad. Sci. USA,* 95(13): 7544-7549, 1998.
Vicari and Caus, *Cytokine Growth Factor Rev.,* 13:143-154, 2002.
Vogelstein and Kinzler, *Cell,* 70(4):523-6, 1992.
Wallach et al., *Annu. Rev. Immunol.,* 17:331-367, 1999.
Wold et al., *J. Virol.* 52:307-313, 1984.
Wold et al., *Trends Microbiol.,* 2:437-443, 1994.
Wong et al., *Gene,* 10:87-94, 1980.
Wu et al., *Biochem. Biophys. Res. Commun.,* 233(1):221-226, 1997.
Zhao-Emonet et al., *Biochim. Biophys. Acta,* 1442(2-3):109-119, 1998.

The invention claimed is:

1. A method for treating cancer in a human subject previously administered a vaccinia virus lacking a thymidine kinase gene and expressing GM-CSF comprising administering to the subject an effective amount of an anti-angiogenic agent that inhibits VEGF-R tyrosine kinase, wherein the inhibitor of VEGF-R tyrosine kinase is administered up to 13 weeks after the vaccinia virus therapy.

2. The method of claim 1, wherein the inhibitor of VEGF-R tyrosine kinase is administered after determining whether a tumor is undergoing re-vascularization.

3. The method of claim 2, wherein determining tumor re-vascularization is by non-invasive imaging of the tumor.

4. The method of claim 3, wherein the non-invasive imaging is magnetic resonance imaging (MRI).

5. The method of claim 4, wherein the magnetic resonance imaging is dynamic contrast-enhanced MRI (dce-MRI).

6. The method of claim 1, wherein the inhibitor of VEGF-R tyrosine kinase is administered at least 1 week after the vaccinia virus administration.

7. The method of claim 1, wherein the cancer is a brain tumor, a head & neck cancer tumor, an esophageal tumor, a skin tumor, a lung tumor, a thymic tumor, a stomach tumor, a colon tumor, a liver tumor, an ovarian tumor, a uterine tumor, a bladder tumor, a testicular tumor, a rectal tumor, a breast tumor, a kidney tumor, a pancreatic tumor, hepatocellular carcinoma or a renal carcinoma.

8. The method of claim 7, wherein the tumor is a pancreatic tumor, a hepatocellular carcinoma or a renal carcinoma.

9. The method of claim 7 wherein the tumor is a metastasis.

10. The method of claim 9, wherein the metastasis is colon or renal metastasis.

11. The method of claim 1, further comprising first administering to the subject the vaccinia virus therapy.

12. The method of claim 11, wherein the vaccinia virus is administered intratumorally, intravascularly, or both intravascularly and intratumorally.

13. The method of claim 1, wherein the vaccinia virus is a Wyeth strain.

14. The method of claim 13, wherein the vaccinia virus is JX-594.

15. The method of claim 1, wherein the inhibitor of VEGF-R tyrosine kinase is administered at least 2 weeks after the vaccinia virus administration.

16. The method of claim 1, wherein the inhibitor of VEGF-R tyrosine kinase is selected from the group consisting of: SU5416, SU6668, vatalanib, AEE788, ZD6474, ZD4190, AZD2171, GW786034, CP-547,632, AG013736, and YM-359445.

17. The method of claim 3, wherein the non-invasive imaging is contrast enhanced CT scanning.

18. The method of claim 1, wherein the cancer has failed to respond favorably to or is resistant to treatment with one or more chemotherapeutic agents.

19. The method of claim 18, wherein the treatment with one or more chemotherapeutic agents comprises administering one or more anti-angiogenic agents.

20. The method of claim 1, wherein the vaccinia virus is administered by intratumoral injection every two weeks.

21. A method for treating cancer in a human subject previously administered a vaccinia virus lacking a thymidine kinase gene and expressing GM-CSF comprising administering to the subject an effective amount of sorafenib, sutent or AG013736 up to 13 weeks after the vaccinia virus therapy.

22. The method of claim 21, wherein the cancer is a pancreatic tumor, a hepatocellular carcinoma or a renal carcinoma.

* * * * *